(12) United States Patent
Clarke et al.

(10) Patent No.: US 11,008,336 B2
(45) Date of Patent: *May 18, 2021

(54) COMPOUNDS USEFUL FOR INHIBITING RORγT

(71) Applicant: Eli Lilly and Company, Indianapolis, IN (US)

(72) Inventors: Christian Alexander Clarke, Fishers, IN (US); Charles Willis Lugar, III, McCordsville, IN (US); John Richard Morphy, Surrey (GB); Timothy Ivo Richardson, Zionsville, IN (US); Helene Rudyk, Surrey (GB); Selma Sapmaz, Basingstoke (GB); Ryan Edward Stites, Indianapolis, IN (US); Grant Mathews Vaught, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/482,577

(22) PCT Filed: Feb. 27, 2018

(86) PCT No.: PCT/US2018/019920
§ 371 (c)(1),
(2) Date: Jul. 31, 2019

(87) PCT Pub. No.: WO2018/160550
PCT Pub. Date: Sep. 7, 2018

(65) Prior Publication Data
US 2020/0048279 A1 Feb. 13, 2020

Related U.S. Application Data

(60) Provisional application No. 62/466,117, filed on Mar. 2, 2017.

(51) Int. Cl.
C07D 495/20 (2006.01)
A61K 45/06 (2006.01)
A61P 29/00 (2006.01)

(52) U.S. Cl.
CPC ............ *C07D 495/20* (2013.01); *A61P 29/00* (2018.01); *A61K 45/06* (2013.01)

(58) Field of Classification Search
CPC ........ C07D 495/20; A61P 29/00; A61K 45/06

USPC .......................................................... 546/18
See application file for complete search history.

(56) References Cited

U.S. PATENT DOCUMENTS

| 9,598,431 | B1* | 3/2017 | Morphy ................. A61P 37/00 |
| 9,868,748 | B2 | 1/2018 | Claremon et al. |
| 10,603,320 | B2* | 3/2020 | Lugar, III ............ C07D 495/14 |
| 2011/0118251 | A1 | 5/2011 | Benito Collado |
| 2012/0214784 | A1 | 8/2012 | Benito Collado |
| 2014/0309251 | A1 | 10/2014 | Kehn |
| 2017/0066781 | A1 | 3/2017 | Morphy |

FOREIGN PATENT DOCUMENTS

| WO | 2015/101928 A1 | 7/2015 |
| WO | 2017/044410 A1 | 3/2017 |

OTHER PUBLICATIONS

Sherlock, et al., 18 Nature Medicine, 1069-1077 (2012).
Raychaudhuri, et al., 35 Clinical Rheumatol., 1437-1441 (2016).
Venken, et al., 17 Curr Rheumatol Rep, 1-8 (2015).

* cited by examiner

*Primary Examiner* — Rita J Desai
(74) *Attorney, Agent, or Firm* — Nelsen L Lentz

(57) ABSTRACT

The present invention provides novel ROR gamma-t inhibitors and pharmaceutical compositions thereof, formula (A).

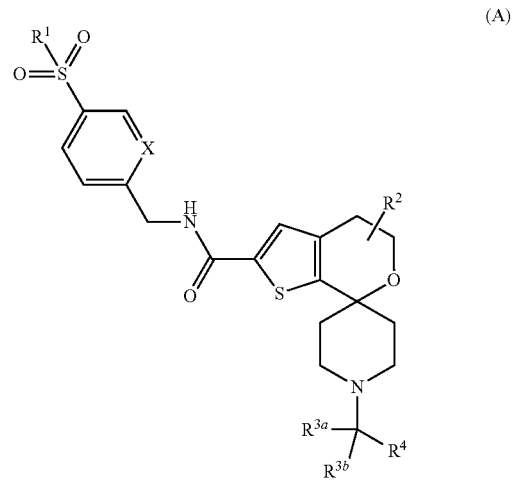

16 Claims, No Drawings

COMPOUNDS USEFUL FOR INHIBITING RORγT

The present invention relates to compounds useful for inhibiting retinoic acid receptor-related orphan receptor gamma-t (RORγt), pharmaceutical compositions, and methods for treating diseases related to RORγ activity.

The retinoic acid receptor-related orphan receptors (RORs) are members of the nuclear receptor (NR) superfamily identified as important pathological regulators in many diseases. The ROR subfamily consists of RORα, RORβ, and RORγ. The mouse and human RORγ gene generates two isoforms, γ1 and γ2, the latter most commonly referred to as γt. RORγt signaling, often in response to IL-23/IL-23 receptor signaling, is required for the differentiation of naive CD4+ T-cells into a subset of T-cells designated Th17, which are distinct from the classical Th1 and Th2 cells, and supports their maintenance. Th17 cells produce interleukin-17A (IL-17) and IL-17F. In addition, Th17 cells produce a range of other factors known to drive inflammatory responses, including tumor necrosis factor-alpha (TNF-α), interleukin-6 (IL-6), GM-CSF, CXCL1 and CCL20. NK cells and innate lymphoid cells such as lymphoid tissue inducer (LTi)-like cells express IL-23 receptor and RORγt and produce IL-17 in response to stimulation and IL-23. There is substantial evidence that IL-23-responsive, RORγt, and IL-17-expressing cells are associated with autoimmune diseases (AI), inflammatory diseases, and cancer. Thus, targeted inhibition of RORγt may be important to reducing the pathogenesis of those diseases.

AI diseases are chronic conditions for which no cure currently exists. Treatment of AI diseases typically involves an attempt to control the process of the disease and decrease the symptoms by administering anti-inflammatory, anti-pain, or immunosuppressant medications. Unfortunately, the use of anti-inflammatory and anti-pain medications is sometimes ineffective and the use of immunosuppressants often leads to devastating long-term side effects. The most significant side effects of immunosuppressant drugs are an increased risk of infection and a higher risk of cancer.

Natural and synthetic ligands to RORγt have been identified. Small molecule inhibitors against RORγt have been reported in the literature for AI. See WO 2015/017335 and WO 2014/179564. However, the prevalence of AI diseases coupled with the ineffectiveness or devastating side effects of current treatments necessitate that more treatment choices be available to patients. Targeting RORγt may present an advantage over current AI therapies by maximizing the therapeutic benefit by targeting pathogenic immune cells while minimizing the risk of suppression of host defenses.

The present invention provides novel compounds that are RORγt inhibitors. Such new compounds could address the need for potent, effective treatment of uveitis, multiple sclerosis, rheumatoid arthritis, graft versus host disease, Crohn's disease, other inflammatory bowel diseases, cancer, psoriasis, and seronegative spondylarthropathies, such as axial spondyloarthritis, ankylosing spondylitis, and psoriatic arthritis.

The present invention provides a compound of formula

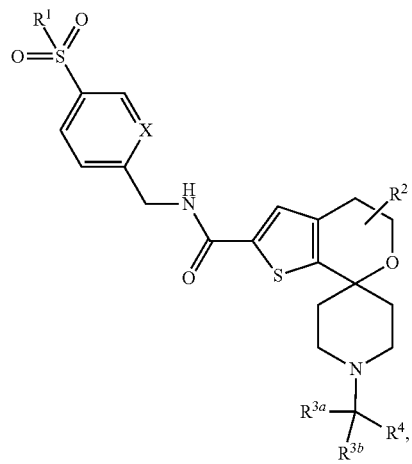

wherein
n is 0, 1, or 2;
X is independently —N— or —CH—;
$R^1$ is —$C_{1-3}$ alkyl;
$R^2$ is —H or —$CH_3$;
$R^{3a}$ and $R^{3b}$ are independently —H, —$CH_3$, or —$CH_2CH_3$;
$R^4$ is

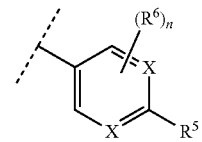

or thiazolyl optionally substituted with —$CF_3$;
$R^5$ is halo, —CN, —$CF_3$, oxadiazolyl, or oxadiazolyl optionally substituted with $CH_3$,
$R_6$ is —H, —OMe, halo, —$CH_3$, or —$CF_3$;
provided that when n is 0, X is —N, —$R^1$ is —$CH_2CH_3$, $R^2$ is —$CH_3$ in the position adjacent to the —O—, $R^{3a}$ and $R^{3b}$ are —H and —$CH_3$, then $R^5$ cannot be —$CF_3$;
or a pharmaceutically acceptable salt thereof.

The present invention also provides a method for the treatment of psoriasis in a patient comprising administering to a patient in need thereof a compound of the present invention, or a pharmaceutically acceptable salt thereof. Further, the present invention provides a method for the treatment of seronegative spondylarthropathies in a patient comprising administering to a patient in need thereof a compound of the present invention, or a pharmaceutically acceptable salt thereof. In said embodiment, seronegative spondylarthropathies are axial spondyloarthritis, ankylosing spondylitis, or psoriatic arthritis.

The present invention provides a pharmaceutical composition comprising a compound of the invention, or a pharmaceutically acceptable salt thereof, in combination with one or more pharmaceutically acceptable carriers, diluents, or excipients. In a further embodiment, the composition further comprises one or more other therapeutic agents. In a further embodiment, the present invention provides a pharmaceutical composition for the treatment of psoriasis comprising a compound of the invention, or a pharmaceutically acceptable salt thereof, in combination with one or more pharmaceutically acceptable carriers, diluents, or excipients. In yet a further embodiment, the present invention provides a pharmaceutical composition for the treatment of seronegative spondylarthropathies comprising a compound of the invention, or a pharmaceutically acceptable salt thereof, in combination with one or more pharmaceutically acceptable carriers, diluents, or excipients. In said embodiment, seronegative spondylarthropathies are axial spondyloarthritis, ankylosing spondylitis, or psoriatic arthritis.

Further, the present invention provides a compound of the invention, or a pharmaceutically acceptable salt thereof, for use in therapy, in particular for the treatment of psoriasis. Even further, the present invention provides a compound of the invention, or a pharmaceutically acceptable salt thereof, for use in the treatment of psoriasis. In a further embodiment, the present invention provides the use of a compound of the invention, or a pharmaceutically acceptable salt thereof, for the manufacture of a medicament for the treatment of psoriasis.

Further, the present invention provides a compound of the invention, or a pharmaceutically acceptable salt thereof, for use in therapy, in particular for the treatment of seronegative spondylarthropathies. Even further, the present invention provides a compound of the invention, or a pharmaceutically acceptable salt thereof, for use in the treatment of seronegative spondylarthropathies. In a further embodiment, the present invention provides the use of a compound of the invention, or a pharmaceutically acceptable salt thereof, for the manufacture of a medicament for the treatment of seronegative spondylarthropathies. In said embodiments, seronegative spondylarthropathies are of axial spondyloarthritis, ankylosing spondylitis, or psoriatic arthritis.

The present invention also encompasses intermediates and processes useful for the synthesis of a compound of the present invention.

The term "treating" (or "treat" or "treatment") as used herein refers to restraining, slowing, stopping, or reversing the progression or severity of an existing symptom, condition or disorder.

The term "spondylarthropathies" refers to a number of chronic joint diseases that generally involve the vertebral column and the areas where ligaments and tendons attach to bone. Spondylarthropathies are sometimes also called spondyloarthropathies or spondyloarthritis.

The term "seronegative" refers to a disease which is negative for reheumatoid factor.

A compound of the present invention may react to form pharmaceutically acceptable salts. Pharmaceutically acceptable salts and common methodology for preparing them are well known in the art. See, e.g., P. Stahl, et al. *Handbook of Pharmaceutical Salts: Properties, Selection and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977.

The skilled artisan will appreciate that a compound of the invention, as shown in (I), or pharmaceutically acceptable salt thereof, is comprised of a core that contains at least two chiral centers, as represented by * below:

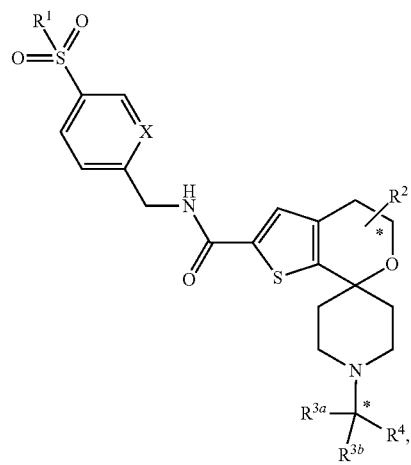

Although the present invention contemplates all individual enantiomers, as well as mixtures of the enantiomers of said compounds including racemates, the preferred compounds of the invention are represented by (II) below:

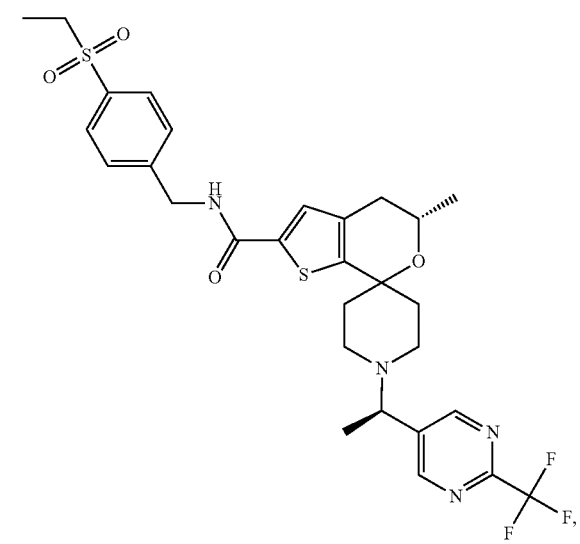

or pharmaceutically acceptable salts thereof.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers of compounds of the invention are a preferred embodiment of the invention.

A compound of the present invention is preferably formulated as pharmaceutical compositions administered by a variety of routes. Such pharmaceutical compositions and processes for preparing the same are well known in the art. See, e.g., *Remington: The Science and Practice of Pharmacy* (A. Gennaro, et al., eds., 22$^{nd}$ ed., Pharmaceutical Press, 2012). More particularly preferred, is a pharmaceutical composition comprising a compound of the formula,

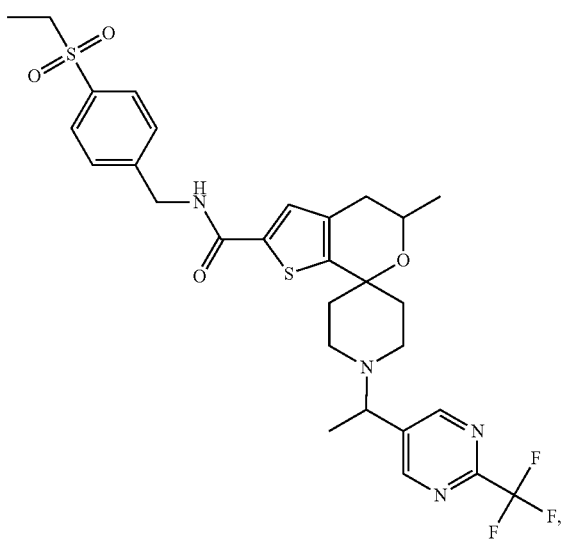 [SMILES: CCS(=O)(=O)c1ccc(CNC(=O)c2cc3c(s2)C2(CCN(C(C)c4cnc(C(F)(F)F)nc4)CC2)OC(C)C3)cc1]

or a pharmaceutically acceptable salt thereof and one or more pharmaceutically acceptable carriers or diluents.

Although all of the compounds of the present invention are useful inhibitors of RORγt, certain classes of compounds are preferred. The following paragraphs describe such preferred classes:

a) $R^1$ is ethyl;
b) $R^1$ is methyl;
c) $R^2$ is —$CH_3$;
d) $R^2$ is —$CH_3$ on the carbon adjacent to the oxygen;
e) $R^{3a}$ and $R^{3b}$ are independently —H or —$CH_3$;
f) $R^{3a}$ and $R^{3b}$ are —H and —H;
g) $R^{3a}$ and $R^{3b}$ are —H and —$CH_3$;
h) n is 0;
i) n is 1;
j) $R^4$ is

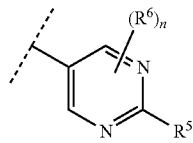

wherein $R^5$ is —$CH_3$ or —$CF_3$;
k) $R^4$ is

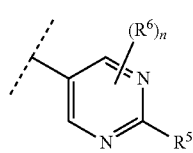

wherein $R^5$ is —$CH_3$ or —$CF_3$, n is 1, and $R^6$ is —$CH_3$;
l) $R^4$ is

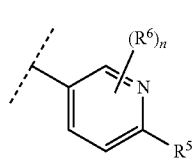

wherein $R^5$ is —$CF_3$;

m) $R^4$ is

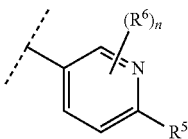

wherein $R^5$ is —$CF_3$, n is 1, and $R^6$ is halo or —$CH_3$;
n) $R^4$ is

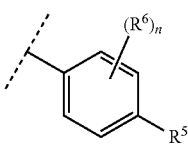

wherein $R^5$ is halo, cyano, —$CF_3$, oxadiazolyl, or oxadiazolyl optionally substituted with —$CH_3$;
o) $R^4$ is

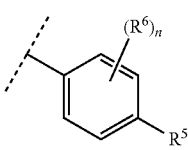

wherein $R^5$ is halo, cyano, —$CF_3$, oxadiazolyl, or oxadiazolyl optionally substituted with —$CH_3$, n is 1, and $R^6$ is —H, —$OCH_3$, halo, —$CH_3$, or —$CF_3$;
p) $R^4$ is

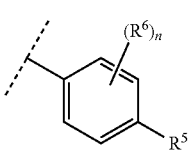

wherein $R^5$ is halo, cyano, —$CF_3$, oxadiazolyl, or oxadiazolyl optionally substituted with —$CH_3$, n is 2, and $R^6$ is —H, —$OCH_3$, halo, —$CH_3$, or —$CF_3$;
q) R4 is thiazolyl optionally substituted with —$CF_3$;

A preferred embodiment of the compounds of the present invention relates compounds of the following formula,

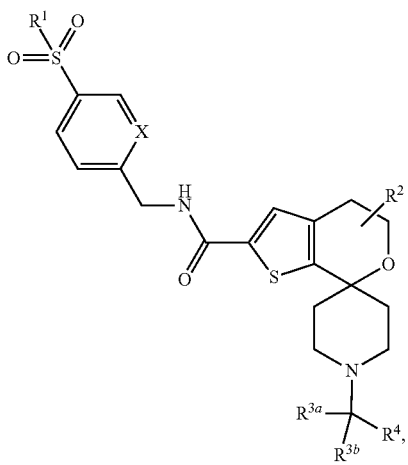

wherein
n is 0, 1, or 2;
X is independently —N— or —CH—;
$R^1$ is —$C_{1-3}$ alkyl;
$R^2$ is —H or —$CH_3$;
$R^{3a}$ and $R^{3b}$ are independently —H, —$CH_3$, or —$CH_2CH_3$;
$R^4$ is

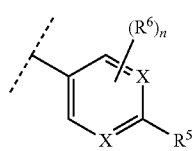

or thiazolyl optionally substituted with —$CF_3$;
$R^5$ is halo, —CN, —$CF_3$, oxadiazolyl, or oxadiazolyl optionally substituted with $CH_3$,
$R_6$ is —H, —OMe, halo, —$CH_3$, or —$CF_3$;
provided that when n is 0, X is —N, —$R^1$ is —$CH_2CH_3$, $R^2$ is —$CH_3$ in the position adjacent to the —O—, $R^{3a}$ and $R^{3b}$ are —H and —$CH_3$, then $R^5$ cannot be —$CF_3$;
or a pharmaceutically acceptable salt thereof.

Another preferred embodiment of the compounds of the present invention relates compounds of the following formula,

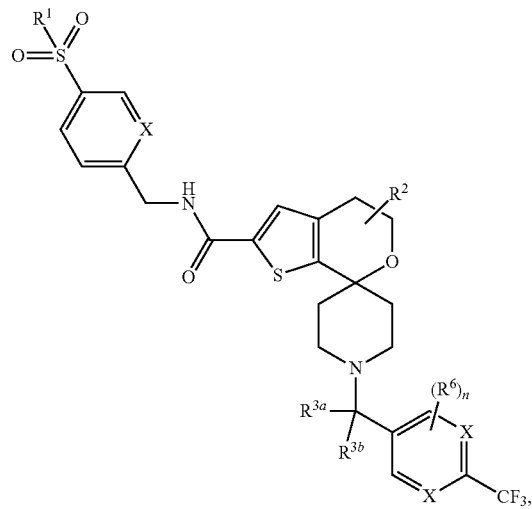

wherein
n is 0 or 1;
X is independently —N— or —CH—;
$R^1$ is —$C_{1-3}$ alkyl;
$R^2$ is —H or —$CH_3$;
$R^{3a}$ and $R^{3b}$ are independently —H, —$CH_3$, or —$CH_2CH_3$;
$R_6$ is halo, or —$CH_3$;
provided that when n is 0, X is —N, —$R^1$ is —$CH_2CH_3$, $R^2$ is —$CH_3$ in the position adjacent to the —O— then $R^{3a}$ and $R^{3b}$ cannot be —H and —$CH_3$;
or a pharmaceutically acceptable salt thereof.

Another preferred embodiment of the compounds of the present invention relates compounds of the following formula,

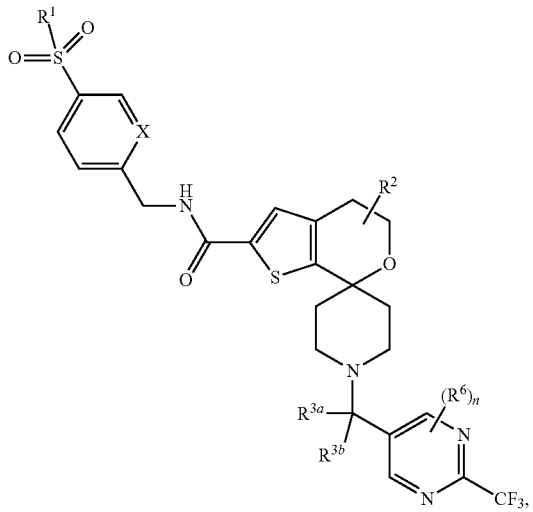

wherein
n is 0 or 1;
X is —N— or —CH—;
$R^1$ is —$C_{1-3}$ alkyl;
$R^2$ is —H or —$CH_3$;
$R^{3a}$ and $R^{3b}$ are independently —H or —$CH_3$;
$R_6$ is —$CH_3$;
provided that when n is 0, X is —N, —$R^1$ is —$CH_2CH_3$, $R^2$ is —$CH_3$ in the position adjacent to the —O— then $R^{3a}$ and $R^{3b}$ cannot be —H and —$CH_3$;
or a pharmaceutically acceptable salt thereof.

Yet another preferred embodiment of the compounds of the present invention relates compounds of the following formula,

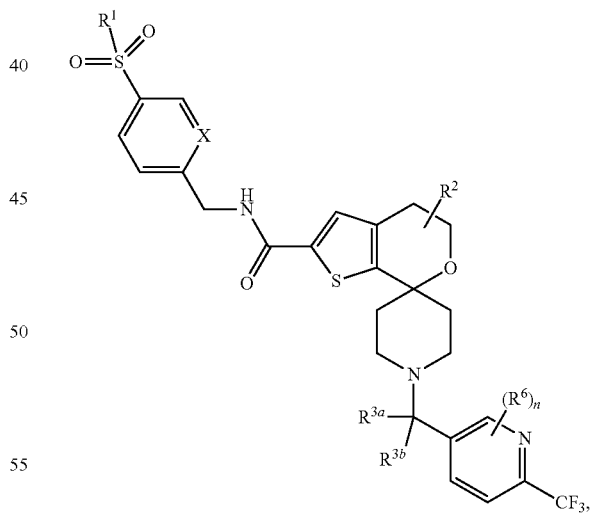

wherein
n is 0 or 1;
X is —N— or —CH—;
$R^1$ is —$C_{1-3}$ alkyl;
$R^2$ is —H or —$CH_3$;
$R^{3a}$ and $R^{3b}$ are independently —H, —$CH_3$, or —$CH_2CH_3$;
$R_6$ is halo or —$CH_3$;
or a pharmaceutically acceptable salt thereof.

Another preferred embodiment of the compounds of the present invention relates compounds of the following formula,

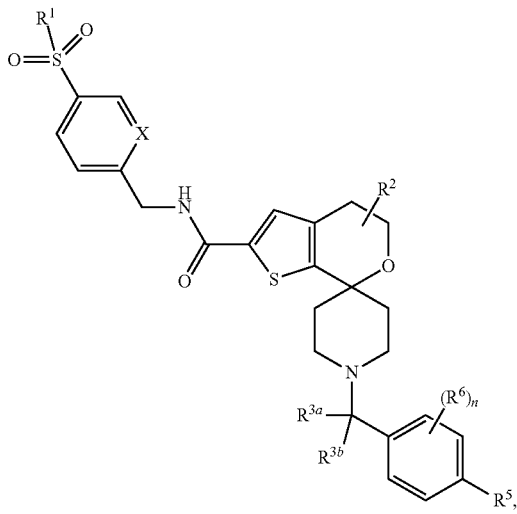

wherein
n is 0, 1, or 2;
X is —N— or —CH—;
$R^1$ is —$C_{1-3}$ alkyl;
$R^2$ is —H or —$CH_3$;
$R^{3a}$ and $R^{3b}$ are independently —H or —$CH_3$;
$R^5$ is halo, —CN, —$CF_3$, oxadiazolyl, or oxadiazolyl optionally substituted with $CH_3$,
$R_6$ is —OMe, halo, —$CH_3$, or —$CF_3$;
or a pharmaceutically acceptable salt thereof.

Another preferred embodiment of the compounds of the present invention relates compounds of the following formula,

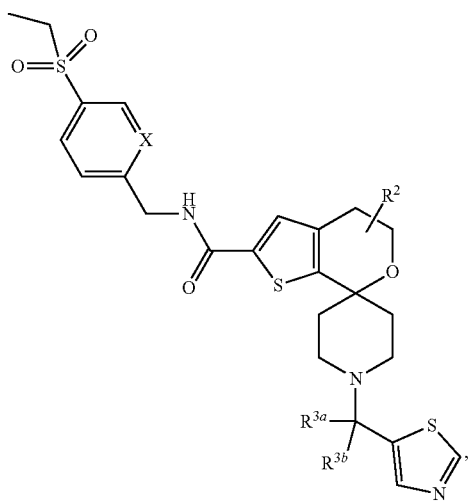

wherein
X is —N— or —CH—;
$R^2$ is —H or —$CH_3$;
$R^{3a}$ and $R^{3b}$ are independently —H or —$CH_3$;
or a pharmaceutically acceptable salt thereof.

Another preferred embodiment of the compounds of the present invention relates compounds of the following formula,

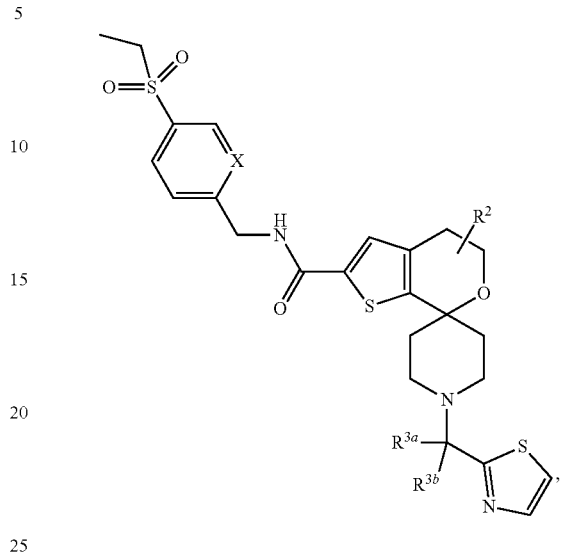

wherein
X is —N— or —CH—;
$R^2$ is —H or —$CH_3$;
$R^{3a}$ and $R^{3b}$ are independently —H or —$CH_3$;
or a pharmaceutically acceptable salt thereof.

An especially preferred embodiment of the present invention relates to the compound, (5'S)—N-[4-(ethylsulfonyl)benzyl]-5'-methyl-1-{(1R)-1-[2-(trifluoromethyl)pyrimidin-5-yl]ethyl}-4',5'-dihydrospiro[piperidine-4,7'-thieno[2,3-c]pyran]-2'-carboxamide:

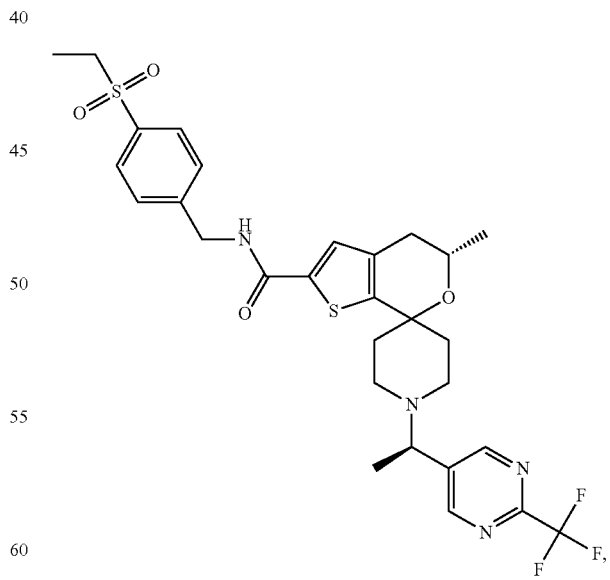

or a pharmaceutically acceptable salt thereof.

Another especially preferred embodiment of the present invention relates to the compound,

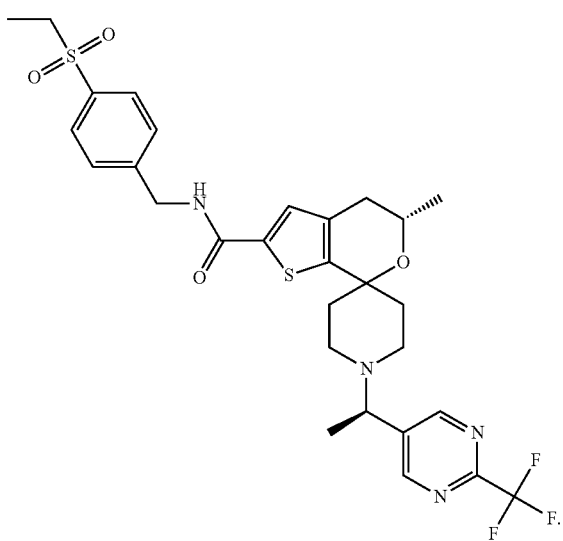 [SMILES: CCS(=O)(=O)c1ccc(CNC(=O)c2cc3c(s2)C2(CCN([C@H](C)c4cnc(C(F)(F)F)nc4)CC2)O[C@@H](C)C3)cc1]

Another especially preferred embodiment of the present invention relates to the compound, (5'S)—N-{[5-(Ethyl-sulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide:

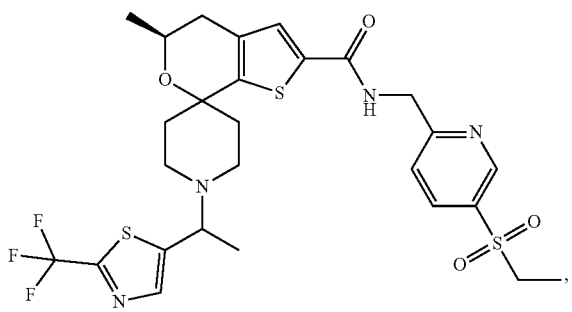 [SMILES: CCS(=O)(=O)c1ccc(CNC(=O)c2cc3c(s2)C2(CCN(C(C)c4cnc(C(F)(F)F)s4)CC2)O[C@@H](C)C3)nc1]

or a pharmaceutically acceptable salt thereof.

Another especially preferred embodiment of the present invention relates to the compound,

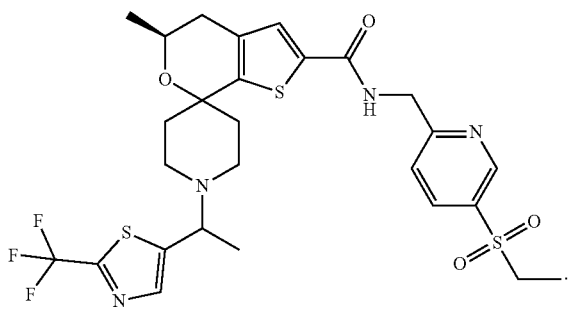 [SMILES: CCS(=O)(=O)c1ccc(CNC(=O)c2cc3c(s2)C2(CCN(C(C)c4cnc(C(F)(F)F)s4)CC2)O[C@@H](C)C3)nc1]

The compounds of the present invention are generally effective over a wide dosage range. For example, dosages per day fall within the range of about 1 mg to 1 g. In some instances, dosage levels below the lower limit of the aforesaid range may be more than adequate, while in other cases still larger doses may be employed while maintaining a favorable benefit/risk profile, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds or salts of the present invention. The products of each step in the Schemes below can be recovered by conventional methods well known in the art, including extraction, evaporation, precipitation, chromatography, filtration, trituration, and crystallization. In the Schemes below, all substituents unless otherwise indicated, are as previously defined. The reagents and starting materials are readily available to one of ordinary skill in the art.

Additionally, certain intermediates described in the following schemes may contain one or more nitrogen or oxygen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain stereochemical centers have been left unspecified and certain substituents have been eliminated in the following schemes for the sake of clarity and are not intended to limit the teaching of the schemes in any way. Single enantiomers or diastereomers may be prepared beginning with chiral reagents or by stereoselective or stereospecific synthetic techniques. Alternatively, the single enantiomers or racemates may be isolated from mixtures by standard chiral chromatographic or crystallization techniques at any convenient point in the synthesis of compounds of the invention by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

Some intermediates or compounds of the present invention may have one or more chiral centers. The present invention contemplates all individual enantiomers or diastereomers, as well as mixtures of the enantiomers and diastereomers of said compounds including racemates. It is preferred that compounds of the present invention containing at least one chiral center exist as a single enantiomer or diastereomer. The single enantiomer or diastereomer may be prepared beginning with chiral reagents or by stereoselective or stereospecific synthetic techniques. Alternatively, the single enantiomer or diastereomer may be isolated from mixtures by standard chiral chromatographic or crystallization techniques. The skilled artisan will appreciate that in some circumstances the elution order of enantiomers or diastereomers may be different due to different chromatographic columns and mobile phases. The designations "isomer 1" and "isomer 2" refer to the compounds that elute from chiral chromatography first and second, respectively, and if chiral chromatography is initiated early in the synthesis, the same designation is applied to subsequent intermediates and examples.

Certain abbreviations are defined as follows: "ACN" refers to acetonitrile; "AUC" refers to area under the curve; "BPR" refers to back pressure regulator; "BSA" refers to Bovine Serum Albumin; "DBA" refers to dilute brown non-Agouti; "DCC" refers to 1,3-dicyclohexylcarbodiimide; "DCM" refers to dichloromethane; "de" refers to diasteriometric excess; "DFT" refers to density functional theory; "DIC" refers to diisopropylcarbodiimide; "DIPEA" refers to diisopropylethylamine, N-ethyl-N-isopropyl-propan-2-amine, or N,N-diisopropylethylamine; "DMAP" refers to 4-dimethylaminopyridine; "DMEM" refers to Dulbecco's Modified Eagle's Medium; "DMF" refers to dimethylformamide; "DMSO" refers to dimethylsulfoxide; "DNA" refers to deoxyribonucleic acid; "DPBS" refers to Dulbecco's phosphate buffered saline; "EDCI" refers to 1-(3-dimethylaminopropyl)-3-ethylcarbodiimide hydrochloride; "$EC_{50}$" refers to effective concentration at half the maximal response; "ee" refers to enantiomeric excess; "ELISA" refers to enzyme-linked immuno assay; "EtOAc" refers to ethyl acetate; "EtOH" refers to ethanol or ethyl alcohol; "$Et_2O$" refers to ethyl ether; "Ex" refers to example; "FBS" refers to Fetal Bovine Serum; "G" refers to gravitational force; "GAL" refers to beta-galactosidase DNA binding domain; "GPI" refers to glucose-6-phosphate isomerase; "HBTU" refers to (2-(1H-benzotriazol-1-yl)-1,1,3, 3-tetramethyluronium hexafluorophosphate); "HEC" refers to hydroxy ethyl cellulose; "HEK" refers to human embryonic kidney; "HEPES" refers to 4-(2-hydroxyethyl)-1-piperazineethanesulfonic acid; "HOAt" refers to 1-hydroxy-7-azobenzotriazole; "HOBt" refers to 1-hydroxylbenzotriazole hydrate; "$IC_{50}$" refers to the concentration of an agent that produces 50% of the maximal inhibitory response possible for that agent; "IL" refers to interleukin; "ion exchange chromatography" refers to purification using ISOLUTE® Flash SCX-2 ion exchange chromatography eluting with 2 M $NH_3$ in MeOH; "IPA" refers to isopropyl alcohol or isopropanol; "IPAm" refers to isopropylamine; "Kd" refers to constant of dissociation; "Ki" refers to inhibition constant; "min" refers to minute or minutes; "MEM" refers to Minimum Essential Medium; "MeOH" refers to methanol or methyl alcohol; "MS" refers to Mass Spectrometry; "MTBE" refers to methyl t-butyl ether; "NBS" refers to N-bromosuccinimide; "PBMC" refers to peripheral blood mononuclear cell; "PBS" refers to phosphate buffered saline, "PEM" refers to photo-elastic modulator; "Prep" refers to preparation; "RAR refers to retinoic acid receptor; "RPMI" refers to Roswell Park Memorial Institute; "RT" refers to room temperature; "$R_t$" refers to retention time; "SCX" refers to strong cation exchange; "SFC" refers to supercritical fluid chromatography; "T3P®" refers to 1-propanephosphonic anhydride solution, 2,4,6-tripropyl-1,3,5,2, 4,6-trioxatriphosphorinane-2,4,6-trioxide solution or PPACA; "TEA" refers to triethylamine; "THF" refers to tetrahydrofuran; "VCD" refers to vibrational circular dichroism and "XRD": refers to X-ray powder diffraction.

In the Schemes below, all substituents unless otherwise indicated, are as previously defined. The reagents and starting materials are readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

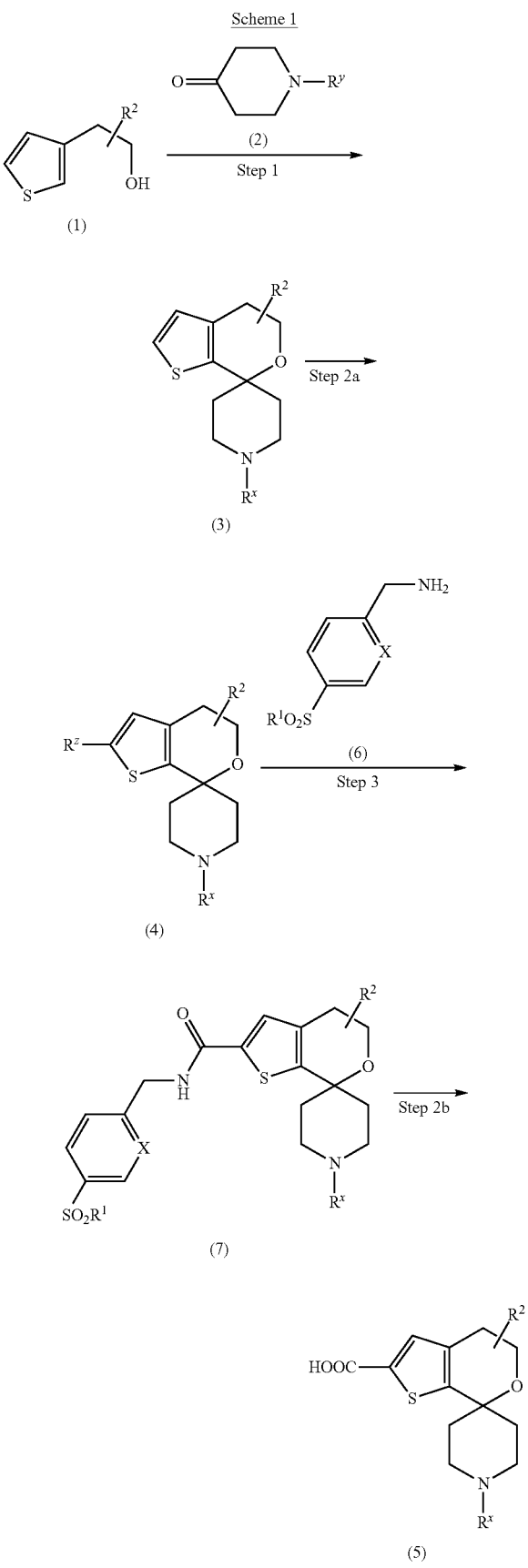

-continued

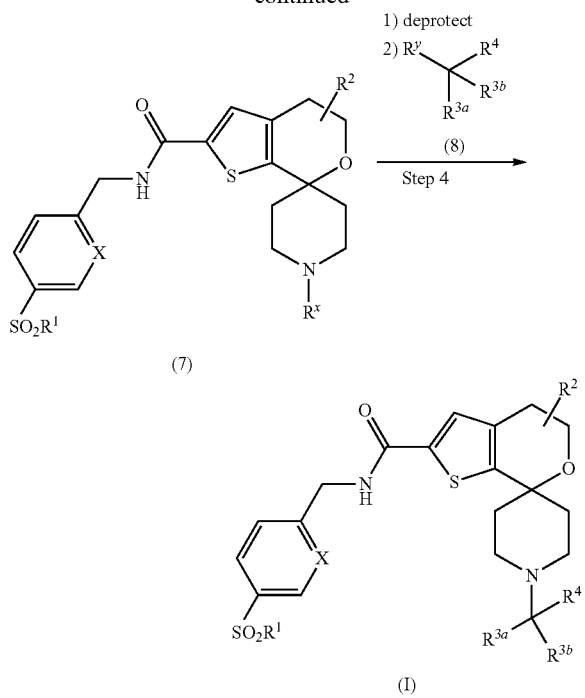

In scheme 1, $R^x$ is an appropriate amine protecting group and $R^y$ is either an appropriate amine protecting group or hydrogen. Amine protecting groups are well known and appreciated in the art, and may include carbamates and amides. One skilled in the art will recognize alternative reagents and procedures to add and remove said protecting groups. $R^z$ is a halogen, such as bromine or chlorine. The skilled artisan will recognize that there are alternative reagents and procedures to introduce halogens.

A person skilled in the art will recognize that there are a variety of methods to prepare substituted hydroxyethyl thiophenes. For example, compound (1) may be prepared from 3-bromo thiophene by displacement of the bromide with a substituted epoxide in the presence of a strong base such as sec-butyllithium or n-butyllithium at a temperature such as −78 to −60° C., followed by ring opening by a Lewis acid such as boron trifluoride diethyl etherate. In Step 1, the substituted hydroxyethyl thiophene (1) and the protected or unprotected 4-keto piperidine (2) may be combined in the presence of an acid such as trifluoroacetic acid to yield the spirothienylpyrano piperidine (3). In the event that the protecting group $R^x$ is removed during step 1, or in the event that $R^y$ is hydrogen, the amine in compound (3) may be protected using a standard amine protecting group such as tert-butyloxycarbonyl. In Step 2a, compound (3) may be halogenated; for example, compound (3) may be brominated with NBS and a catalyst such as dimethylamino pyridine to give compound (4). Alternatively, in step 2b, compound (3) may be carboxylated by carbon dioxide in the presence of a strong base such as butyllithium to provide compound (5).

In step 3, compound (4) may be reacted with carbon monoxide and the amine (6) in the presence of an organometallic ligand, such as 4,5-bis-(diphenylphosphino)-9,9-dimethylxanthene, a catalyst, such as palladium (II) acetate, and a base, such as DIPEA, to provide compound (7). The skilled artisan will appreciate that there are alternative ligands and catalysts. Alternatively, in step 3, compound (5) may be converted to the amide (7) under standard coupling conditions. The coupling of carboxylic acid (5) with amine (6) can be affected in the presence of a suitable coupling reagent, such as T3P® and a suitable amine base, such as DIPEA. Alternative coupling reagents include HOBt, HBTU, and HOAt and carbodiimides, such as DCC, DIC, EDCI. Alternative bases include trimethylamine and TEA. One skilled in the art will recognize that there are a number of other methods and reagents for amide formation resulting from the reaction of carboxylic acids and amines. Additives such as DMAP may be used to enhance the reactions. Alternatively, compound (6) can be acylated using a substituted acyl chloride of compound (5) in the presence of a base, such as TEA or pyridine.

In step 4, compound (7) may be deprotected following appropriate conditions known in the art. For example, a tert-butyloxycarbonyl protecting group may be removed with HCl. The free amine may be alkylated with an appropriately substituted group of $R^4$, where $R^y$ is a leaving group such as a halogen or a sulfonate, in the presence of an organic base such as DIPEA or an inorganic base such as potassium carbonate to provide a compound of Formula (I).

A pharmaceutically acceptable salt of the compounds of the invention, such as a hydrochloride salt, can be formed, for example, by reaction of an appropriate free base of a compound of the invention, an appropriate pharmaceutically acceptable acid such as hydrochloric acid in a suitable solvent such as $Et_2O$ under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The compounds of the present invention, or salts thereof, may be prepared by a variety of procedures known in the art, some of which are illustrated in the Preparations and Examples below. The specific synthetic steps for each of the routes described may be combined in different ways to prepare compounds of the invention, or salts thereof. The products of each step below can be recovered by conventional methods well known in the art, including extraction, evaporation, precipitation, chromatography, filtration, trituration, and crystallization. The reagents and starting materials are readily available to one of ordinary skill in the art.

The following preparations and examples further illustrate the invention and represent typical synthesis of the compounds of the present invention

PREPARATIONS AND EXAMPLES

Preparation 1

1-(3-Thienyl)propan-2-one

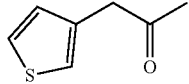

Suspend 2-(3-thienyl)acetic acid (26.5 g, 146.5 mmol) in acetic anhydride (87.9 mL, 913 mmol,) and add 1-methylimidazole (7.57 g, 91.3 mmol). Stir the reaction mixture for 4 hours at room temperature under nitrogen. Cool the reaction mixture to 0° C., add water (150 mL), and stir for 1 hour. Dilute the solution with EtOAc (300 mL) and wash successively with 2 M NaOH (2×200 ml), water (200 mL) and brine (200 mL). Dry the organic extract over sodium sulfate, filter, and concentrate to dryness to obtain the title compound (28.16 g, 77%) as a yellow oil. $^1$H NMR (400.13 MHz, CDCl$_3$) δ 2.14 (s 3H), 3.7 (s, 2H), 6.94 (d, J=5.1 Hz, 1H), 7.08 (bs, 1H), 7.29-7.26 (m, 1H).

Preparation 2

1-(3-Thienyl)propan-2-ol

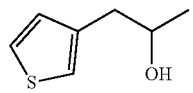

Add sodium borohydride (1.61 g, 41.67 mmol) and dry MeOH (63 mL) together and cool the reaction mixture to −10° C. while adding the MeOH. Cool further to −20° C. and add a solution of 1-(3-thienyl)propan-2-one (4.92 g, 33.34 mmol) in dry MeOH (26.7 mL) dropwise over 40 minutes and stir for 1.5 hours at −20° C. then at room temperature for 17 hours. Cool the solution to −5° C. (internal temperature) and quench with a saturated solution of ammonium chloride (15 ml) then with 1 N HCl (15 mL). Add water (30 mL) and EtOAc (100 mL). Concentrate the mixture under reduced pressure to ⅓ of total volume. Extract the mixture with EtOAc (2×100 mL). Combine the organic extracts and dry over magnesium sulfate, filter, and concentrate to dryness to give the title compound (4.74 g, 100%). Mass spectrum (m/z): 125 (M−OH+H), 164.8 (M+Na).

Alternate Preparation 2a

Add sodium borohydride (7.06 g, 182.8 mmol) portion wise over 30 minutes at 0° C. to a solution of 1-(3-thienyl) propan-2-one (28.16 g, 140.6 mmol) in MeOH (282 mL) and stir at room temperature overnight. Concentrate to dryness, dilute with EtOAc (200 mL) and wash with a saturated solution of ammonium chloride (150 mL). Extract the aqueous layer with EtOAc (2×200 mL). Combine the organic extracts, dry over sodium sulfate, filter, and concentrate under reduced pressure. Purify the residue by silica gel flash chromatography eluting with MeOH: DCM (0:100 to 5:95) to give the title compound (12.85 g, 64%) as a pale red oil. Mass spectrum (m/z): 125 (M−OH+H).

Preparation 3

(2S)-1-(3-Thienyl)propan-2-ol

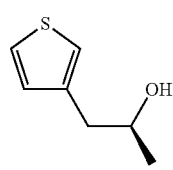

Dissolve 3-bromothiophene (6.88 g, 42.2 mmol) in anhydrous THF (10 mL) and toluene (100 mL). Cool to −78° C. To this add via syringe sec-butyllithium (1.3 mol/L in cyclohexane, 34 mL, 44 mmol) over 15 minutes. Maintain the temperature at <−60° C., stir 10 minutes, then add (2S)-2-methyloxirane (4.9 g, 84.4 mmol) dropwise. After 5 minutes, add boron trifluoride diethyl etherate (5.3 mL, 42 mmol) over 15 minutes via dropping funnel. Maintain the temperature at <−55° C. After the addition is complete, stir at −78° C. for 2 hours. Quench at −78° C. with saturated sodium bicarbonate, add Et$_2$O, and warm to ambient temperature. Wash with saturated sodium bicarbonate (2×) followed by saturated brine. Dry the organic layer over sodium sulfate, filter, and concentrate under reduced pressure. Purify by silica gel flash chromatography eluting with 15% EtOAc/hexanes to give the title compound (3.85 g, 64.2%). Re-purify the mixed fractions to give a total amount of the title compound (4.29 g, 71.5%) as a colorless liquid. $^1$H NMR (400.13 MHz, CDCl$_3$) δ 7.28-7.26 (dd, J=2.9, 5.0, 1H), 7.03-7.01 (m, 1H), 6.96 (dd, J=1.2, 4.9, 1H), 4.04-3.95 (m, 1H), 2.83-2.68 (m, 2H), 1.63 (s, 1H), 1.22 (d, J=6.2, 3H), OR [α]$^{20}$D+25.50 (c 1.00, CHCl$_3$).

Prepare the following compound essentially by the method of Preparation 3.

TABLE 1

| Prep No. | Chemical Name | Structure | $^1$H NMR (400.13 MHz, CDCl$_3$) δ |
|---|---|---|---|
| 4 | (2R)-1-(3-Thienyl)propan-2-ol | 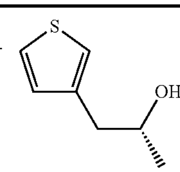 | 7.28-7.26 (dd, J = 2.9, 5.0, 1H), 7.03-7.01 (m, 1H), 6.96 (dd, J = 1.2, 4.9, 1H), 4.04-3.95 (m, 1H), 2.83-2.68 (m, 2H), 1.63 (s, 1H), 1.22 (d, J = 6.2, 3H) |

Preparation 5

(4S)-4-Benzyl-3-[(2S)-2-(3-Thienyl)Propanoyl]Oxazolidin-2-One

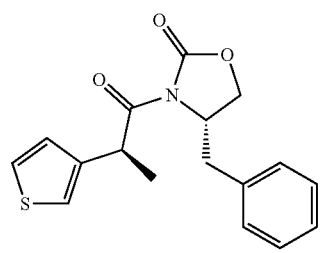 [SMILES: C[C@H](C(=O)N1C(=O)OC[C@@H]1Cc1ccccc1)c1ccsc1]

Add sodium bis(trimethylsilyl)amide in THF (1 mol/L, 40 mL, 40.0 mmol) to a solution of (4S)-4-benzyl-3-[2-(3-thienyl)acetyl]oxazolidin-2-one (10.20 g, 33.86 mmol) in THF (75 mL) at −78° C. under a nitrogen atmosphere and stir for 1 hour. Add neat iodomethane (2.5 mL, 40 mmol) to the reaction mixture, and stir for 1.5 hours at −78° C. then allow to warm to room temperature. After one hour, quench with saturated aqueous ammonium chloride (75 mL) and

Preparation 6

(5'S)-5'-Methyl-4',5'-dihydrospiro[piperidine-4,7'-thieno[2,3-c]pyran]

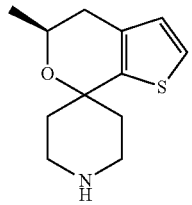

Dissolve tert-butyl 4-oxopiperidine-1-carboxylate (6.50 g, 32.6 mmol) and (2S)-1-(3-thienyl)propan-2-ol (4.64 g, 32.6 mmol) in DCM (100 mL). Add trifluoroacetic acid (20 mL, 264.5 mmol). Stir the mixture at ambient temperature 18 hours. Concentrate the mixture under reduced pressure, and then add water and Et$_2$O. Wash the organic layer with water, combine the aqueous washes, and adjust the pH to basic with solid sodium carbonate. Saturate the aqueous layer with solid sodium chloride, then wash the aqueous layer with EtOAc (5×). Combine the EtOAc layers, wash with brine, dry with sodium sulfate, filter, and concentrate under reduced pressure to give the title compound (4.61 g, 63%) as a pale yellow oil. Mass spectrum (m/z): 224.2 (M+H).

Prepare the following compound essentially by the method of Preparation 6.

TABLE 2

| Prep No. | Chemical Name | Structure | ES/MS (m/z) (M + 1) |
|---|---|---|---|
| 7 | (5'R)-5'-Methyl-4',5'-dihydrospiro[piperidine-4,7'-thieno[2,3-c]pyran] | 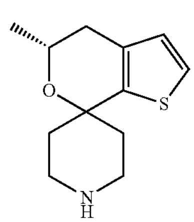 | 224.2 (M + H) |

Preparation 8 tert-Butyl (5'S)-5'-methyl-4',5'-dihydro-1H-spiro[piperidine-4,7'-thieno[2,3-c]pyran]-1-carboxylate

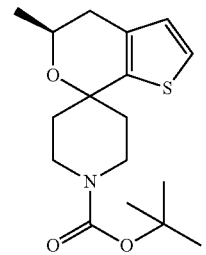 [SMILES: C[C@H]1Cc2ccsc2C2(CCN(C(=O)OC(C)(C)C)CC2)O1]

Dissolve (5'S)-5'-methyl-4',5'-dihydrospiro[piperidine-4,7'-thieno[2,3-c]pyran] (10.39 g, 46.53 mmol) in DCM (100 mL). Add di-tert-butyl dicarbonate (11.52 mL, 51.18 mmol) dropwise and stir the mixture at ambient temperature for 1.5 hours. Add additional di-tert-butyl dicarbonate (2.00 mL, 9.17 mmol) and stir 30 minutes, then concentrate under reduced pressure. Add imidazole (2.21 g, 32.5 mmol) to destroy excess di-tert-butyl dicarbonate (Synthesis, 2001, No. 4, 550). Add Et$_2$O and wash with brine. Dry the organic layer over sodium sulfate, filter, and concentrate under reduced pressure. Purify by silica gel flash chromatography eluting with 10% EtOAc/hexanes. Re-purify by silica gel flash chromatography eluting with 15% EtOAc/hexanes to give the title compound (12.92 g, 86%) as a colorless oil. $^1$H NMR (400.13 MHz, d$_6$-DMSO) δ 7.33 (d, J=5.1, 1H), 6.77 (d, J=5.1, 1H), 3.92-3.72 (m, 3H), 3.15-2.91 (s, 2H), 2.62 (dd, J=15.8, 3.0, 1H), 2.30 (dd, J=15.8, 10.6, 1H), 2.1 (m, 1H), 1.76-1.63 (m, 2H), 1.51-1.40 (m, 1H), 1.38 (s, 9H), 1.24 (d, J=6.2, 3H), 100% ee based on SFC chromatography, Lux Amylose-2, 5 mL/minute, 225 nm, R$_t$=1.75 min, OR [α]$^{20}_D$+82.1 (c 1.00, CHCl$_3$).

Prepare the following compounds essentially by the method of Preparation 8.

TABLE 3

| Prep No. | Chemical Name | Structure | ES/MS (m/z) (M + 1) |
|---|---|---|---|
| 9 | tert-Butyl (5'R)-5'-methyl-4',5'-dihydro-1H-spiro[piperidine-4,7'-thieno[2,3-c]pyran]-1-carboxylate | 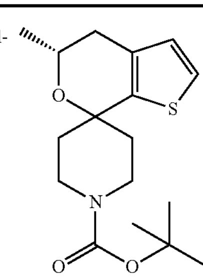 | 224 (M − BOC + H) |

(top of page, continued from previous)

concentrate to dryness. Dissolve the residue in EtOAc and wash the organic phase successively with aqueous 0.5 N HCl, saturated aqueous NaHCO$_3$, water, and brine. Re-extract the basic layer with EtOAc, collect the organic extract and combine with the brine wash. Separate the organic layer and combine all the organic extracts. Dry the material over magnesium sulfate, filter, and concentrate to dryness. Purify the crude material by silica gel flash chromatography eluting with a gradient of EtOAc/iso-hexane (0:100 to 50:50) to give the title compound (8.62 g, 69%). Mass spectrum (m/z): 316 (M+H), 338 (M+Na).

Preparation 10 tert-Butyl-5'-methyl-4',5'-dihydro-1H-spiro[piperidine-4,7'-thieno[2,3-c]pyran]-1-carboxylate

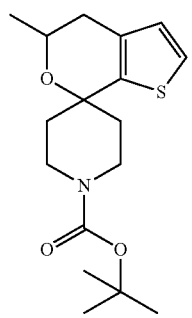 [SMILES: CC1Cc2ccsc2C2(CCN(C(=O)OC(C)(C)C)CC2)O1]

Add trifluoroacetic acid (34.16 mL, 451.8 mmol) dropwise at 0° C. to a solution of 1-(3-thienyl)propan-2-ol (12.85 g, 90.35 mmol) and tert-butyl 4-oxopiperidine-1-carboxylate (23.40 g, 117.5 mmol) in dry DCM (135 mL) and maintain stirring at room temperature for 17 hours. Concentrate the mixture to dryness, dilute the residue with MeOH, and then remove the solvent under reduced pressure. Take up the residue in MeOH and purify by ion exchange chromatography. Combine the fractions containing the desired product and concentrate under reduced pressure co-evaporating with toluene (3×) to give a pale orange solid of crude 5-methylspiro[4,5-dihydrothieno[2,3-c]pyran-7,4'-piperidine]. Add DMAP (2.23 g, 18.07 mmol) and TEA (37.8 mL, 271.1 mmol) dropwise to a solution of 5-methylspiro[4,5-dihydrothieno[2,3-c]pyran-7,4'-piperidine] (20.18 g, 90.35 mmol) in dry DCM (90.35 mL) cooled to 0° C. To this add dropwise a solution of di-tert-butyl dicarbonate (30.49 g, 135.5 mmol,) in dry DCM (27.1 mL). Stir at room temperature overnight. Add water (100 mL), extract the aqueous layer with DCM (3×100 mL), wash with brine (100 mL), and concentrate under reduced pressure. Purify by silica gel flash chromatography eluting with EtOAc: iso-hexanes (0:100 to 20:80). Co-evaporate the residue with DCM (3×) to give the title compound (27.64 g, 92.7%) as a white solid. Mass spectrum (m/z): 346 (M+Na).

Alternate Preparation 10a tert-Butyl-5'-methyl-4',5'-dihydro-1H-spiro[piperidine-4,7'-thieno[2,3-c]pyran]-1-carboxylate Add trifluoroacetic acid (20.17 mL, 266.72 mmol) dropwise at 0° C. to a solution of 1-(3-thienyl)propan-2-ol (4.74 g, 33.34 mmol) and tert-butyl 4-oxopiperidine-1-carboxylate (7.80 g, 38.34 mmol) in dry DCM (100 mL) and stir at room temperature overnight. Concentrate the mixture to dryness and dilute the residue with MeOH. Purify the crude material by ion exchange chromatography. Combine the layers containing the desired product and concentrate under reduced pressure co-evaporating with DCM (3×) to give crude 5-methylspiro[4,5-dihydrothieno[2,3-c]pyran-7,4'-piperidine] (8.17 g). Add DMAP (0.831 g, 6.67 mmol) and TEA (9.29 mL, 66.68 mmol) to a solution of 5-methylspiro[4,5-dihydrothieno[2,3-c]pyran-7,4'-piperidine] (8.17 g) in dry DCM (66.7 mL) cooled to 0° C. To this add dropwise a solution of di-tert-butyl dicarbonate (18.19 g, 83.35 mmol,) in dry DCM (16.7 mL). Stir at room temperature for 3 days. Add water (60 mL), extract the aqueous layer with DCM (3×50 mL), wash with brine (20 mL), filter through a phase separator, and concentrate under reduced pressure. Purify the residue by silica gel flash chromatography eluting with EtOAc: iso-hexanes (0:100 to 20:80). Co-evaporate the residue with DCM (2×) to give the title compound (9.41 g, 80%). Mass spectrum (m/z): 346 (M+Na).

Prepare the following compounds essentially by the method of Alternate Preparation 10a.

TABLE 4

| Prep No. | Chemical Name | Structure | ES/MS (m/z) |
|---|---|---|---|
| 11 | tert-Butyl 4'-methyl-4',5'-dihydro-1H-spiro[piperidine-4,7'-thieno[2,3-c]pyran]-1-carboxylate | 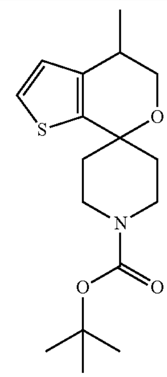 [SMILES: CC1COC2(CCN(C(=O)OC(C)(C)C)CC2)c2sccc21] | 346 (M + Na). |
| 12 | tert-Butyl (4'S)-4'-methyl-4',5'-dihydro-1H-spiro[piperidine-4,7'-thieno[2,3-c]pyran]-1-carboxylate | 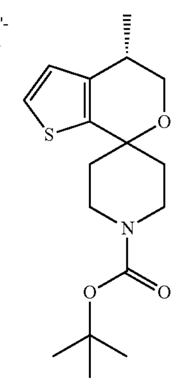 | 346 (M + Na) |

Preparation 13 tert-Butyl 2-bromo-4-methyl-spiro[4,5-dihydrothieno[2,3-c]pyran-7,4'-piperidine]-1'-carboxylate

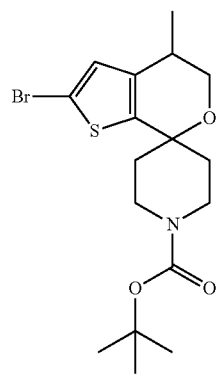

Cool a solution of tert-butyl 4'-methyl-4',5'-dihydro-1H-spiro[piperidine-4,7'-thieno[2,3-c]pyran]-1-carboxylate (4.73 g, 13.2 mmol) in ACN (112 mL) to 0° C. then add DMAP (0.162 g, 1.32 mmol) and NBS (2.60 g, 14.5 mmol) portion wise maintaining stirring for 2.5 hours. Add a mixture of MTBE/iso-hexane (1:1, 100 mL) to the reaction mixture and stir for 50 minutes then concentrate to dryness. Take up the residue in DCM (100 mL), wash with saturated aqueous $Na_2S_2O_3$ (45 mL) followed by brine (25 mL). Filter through a phase separator cartridge and concentrate to dryness to obtain the title compound (5.69 g, 88.1%) as a yellow oil. Mass spectrum (m/z): 424/426 (M+Na).

Prepare the following compounds essentially by the method of Preparation 13.

TABLE 5

| Prep No. | Chemical Name | Structure | ES/MS (m/z) (M + H) |
|---|---|---|---|
| 14 | tert-Butyl (5'S)-2'-bromo-5'-methyl-4',5'-dihydro-1H-spiro[piperidine-4,7'-thieno[2,3-c]pyran]-1-carboxylate | 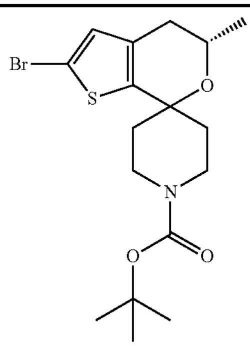 | 302/304 M – BOC |

Preparation 15

1-(tert-Butoxycarbonyl)-5'-methyl-4',5'-dihydrospiro[piperidine-4,7'-thieno[2,3-c]pyran]-2'-carboxylic acid

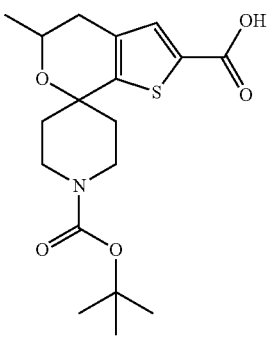 [SMILES: CC1Cc2cc(C(=O)O)sc2C2(CCN(C(=O)OC(C)(C)C)CC2)O1]

Dissolve tert-butyl-5'-methyl-4',5'-dihydro-1H-spiro[piperidine-4,7'-thieno[2,3-c]pyran]-1-carboxylate (7.16 g, 21.71 mmol) in THF (108.5 mL) and cool to −78° C. To this add butyllithium (2.5 M in hexanes, 13 mL, 32.56 mmol) dropwise over 20 minutes and stir the mixture an additional 30 minutes after addition is complete. Bubble in $CO_2$ via cannula and maintain stirring at this temperature for with continuous addition of $CO_2$. Allow the reaction to warm to 0° C. over 2 hours with continuous addition of $CO_2$ and quench carefully with water (80 mL). Pour the reaction mixture into water and extract the aqueous layer with $Et_2O$ (100 mL). Wash the organic phase with 2 N NaOH (3×15 mL) and water (50 mL). Acidify the aqueous layer with 2 N HCl (3×) to pH=6, and extract with EtOAc. Combine the organic extracts, wash with brine (50 mL), dry over magnesium sulfate, filter, and concentrate under reduced pressure to obtain the title compound (7.89 g, 97%) as an off-white solid. Mass spectrum (m/z): 390 (M+Na).

Preparation 16

1-(tert-Butoxycarbonyl)-4',5'-dihydrospiro[piperidine-4,7'-thieno[2,3-c]pyran]-2'-carboxylic acid

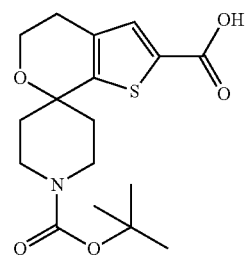 [SMILES: CC(C)(C)OC(=O)N1CCC2(CC1)OCCc1cc(C(=O)O)sc12]

Dissolve tert-butyl-4',5'-dihydro-1H-spiro[piperidine-4,7'-thieno[2,3-c]pyran]-1-carboxylate (prepared as described in J. Med. Chem., 2011, 54, (8), pp 2687-2700 and WO2011060035) (10 g, 32.32 mmol) in THF (100 mL) and cool to −78° C. To this add butyllithium (22.22 mL, 35.55 mmol) dropwise over 15 minutes and stir the mixture an additional 15 minutes after addition is complete. Bubble in $CO_2$ via cannula and allow the mixture to warm to room temperature with continuous addition of $CO_2$. After 2 hours, cool the mixture to 0° C., and add water followed by $Et_2O$. Adjust the pH of the aqueous layer with 1 N NaOH to basic pH and wash the organic layer with 1 N NaOH (3×). Combine the base washes and acidify to pH 2 with 5 N HCl. Extract the aqueous layer with EtOAc (3×), combine the organic extracts, and wash with brine. Dry over sodium sulfate, filter, and concentrate under reduced pressure to give the title compound (11.11 g, 97.27%) as a white solid. Mass spectrum (m/z): 352.2 (M−H).

Prepare the following compound essentially by the method of Preparation 16.

TABLE 6

| Prep No. | Chemical Name | Structure | ES/MS (m/z) (M − 1) |
|---|---|---|---|
| 17 | (5'R)-1-(tert-Butoxycarbonyl)-5'-methyl-4',5'-dihydrospiro[piperidine-4,7'-thieno[2,3-c]pyran]-2'-carboxylic acid | 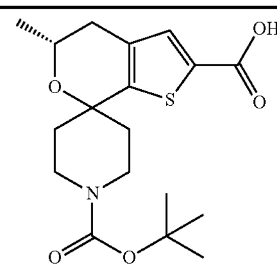 | 366 (M − H) |

Preparation 18

(5'S)-1-tert-Butoxycarbonyl-5'-methyl-4',5'-dihydrospiro[piperidine-4,7'-thieno[2,3-c]pyran]-2'-carboxylic acid

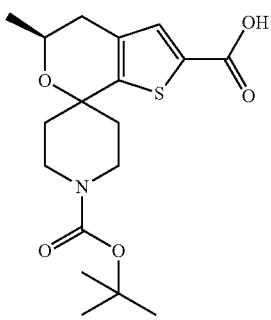 [SMILES: C[C@H]1Cc2cc(C(=O)O)sc2C2(CCN(C(=O)OC(C)(C)C)CC2)O1]

Dissolve tert-butyl (5'S)-5'-methyl-4',5'-dihydro-1H-spiro[piperidine-4,7'-thieno[2,3-c]pyran]-1-carboxylate (11.19 g, 34.60 mmol) in anhydrous THF (200 mL) and cool to −78° C. Add n-butyllithium (21 mL, 34.64 mmol) dropwise over 20 minutes. After addition is complete, stir at −78° C. for 20 minutes, then bubble in $CO_2$ gas via cannula for 60 minutes. Warm the mixture to room temperature with continuous addition of $CO_2$. After stirring 1 hour at room temperature, quench with water (3 mL) and concentrate under reduced pressure to 25% volume. Add $Et_2O$ and water. Wash with water (2×) and combine the aqueous washes. Adjust the pH to acidic pH with 1 N HCl. Saturate the aqueous layer with sodium chloride and extract with EtOAc (2×). Combine the EtOAc extracts, wash with brine, dry over sodium sulfate, filter, and concentrate under reduced pressure to give the title compound (13.40 g, 100%) as a white foam. Mass spectrum (m/z): 366 (M−H).

Preparation 19

O1'-tert-Butyl O2-methyl spiro[4,5-dihydrothieno[2,3-c]pyran-7,4'-piperidine]-1',2-dicarboxylate

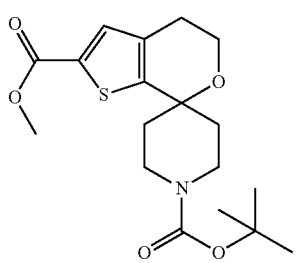 [SMILES: COC(=O)c1cc2c(s1)C1(CCN(C(=O)OC(C)(C)C)CC1)OCC2]

Dissolve 1-(tert-butoxycarbonyl)-4',5'-dihydrospiro[piperidine-4,7'-thieno[2,3-c]pyran]-2'-carboxylic acid (40.0 g, 129.27 mL) in THF (750 mL) and cool to −78° C. Add n-butyllithium (1.6 M in hexanes, 88.8 mL, 142.2 mmol) dropwise over 45 minutes such that T<−60° C. After addition, stir 15 minutes and cool to −78° C. Add methyl chloroformate (15.0 mL, 193.9 mmol) dropwise over 15 minutes such that T<−50° C. After addition, stir 60 minutes and cool to −78° C. Quench slowly with saturated aqueous sodium bicarbonate (100 mL) and warm to ambient temperature. Concentrate under reduced pressure to about 25% volume and add $Et_2O$ and water. Separate the layers and wash the organic layer with saturated aqueous sodium bicarbonate followed by brine. Dry the organic layer over sodium sulfate, filter, and concentrate under reduced pressure. Purify the residue by silica gel flash chromatography eluting with 0-100% EtOAc in hexanes to give the title compound (37.39 g, 79%) as a colorless foam. $^1$H NMR (400.13 MHz, $CDCl_3$) δ 7.46 (s, 1H), 3.97 (m, 2H), 3.91 (t, J=5.5 Hz, 2H), 3.84 (s, 3H), 3.12 (m, 2H), 2.69 (t, J=5.5 Hz, 2H), 1.97 (m, 2H), 1.76 (m, 2H), 1.46 (s, 9H).

Preparation 20

Methyl 4',5'-dihydrospiro[piperidine-4,7'-thieno[2,3-c]pyran]-2'-carboxylate hydrochloride

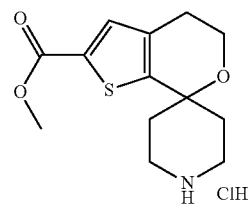 [SMILES: COC(=O)c1cc2c(s1)C1(CCNCC1)OCC2 ; Cl]

Combine O1'-tert-Butyl O2-methyl spiro[4,5-dihydrothieno[2,3-c]pyran-7,4'-piperidine]-1',2-dicarboxylate (5.0 g, 13 mmol), 1,4-dioxane (50 mL), MeOH (70 mL) and HCl (4 mol/L) in 1,4-dioxane (70 mL, 280 mmol). Stir for 45 minutes. Concentrate the reaction under reduced pressure to give the title compound as an off-white solid (4.25 g, 100% crude) which is used without further purification. Mass spectrum (m/z): 268 (M−HCl+H).

Preparation 21

Methyl 1-(2,4-dichlorobenzyl)-4',5'-dihydrobenzyl)-4',5'-dihydrospiro[piperidine-4,7'-thieno[2,3-c]pyran]-2'-carboxylate

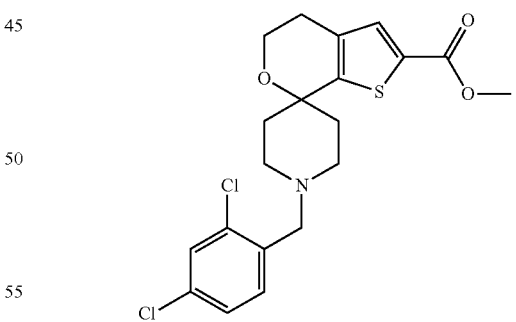

Combine methyl 4',5'-dihydrospiro[piperidine-4,7'-thieno[2,3-c]pyran]-2'-carboxylate hydrochloride (4.25 g, 14.0 mmol), acetonitrile (70 mL), 2,4-dichlorobenzyl chloride (2.2 mL, 16 mmol) and DIPEA (10 mL, 57.3 mmol). Warm the reaction to 75° C. and stir for 1.75 hours. Cool the reaction to ambient temperature and concentrate under reduced pressure. Purify via silica gel chromatography eluting with 0-35% EtOAc in hexanes to give the title compound (5.5 g, 92%) as a tan foam. Mass spectrum (m/z): 426/428/430 (M+H).

Preparation 22

1'-[(2,4-Dichlorophenyl)methyl]spiro[4,5-dihydrothieno[2,3-c]pyran-7,4'-piperidine]-2-carboxylic acid

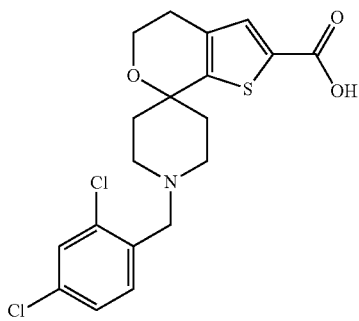 [SMILES: O=C(O)c1cc2c(s1)C1(CCN(Cc3ccc(Cl)cc3Cl)CC1)OCC2]

Combine methyl 1-(2,4-dichlorobenzyl)-4',5'-dihydrobenzyl)-4',5'-dihydrospiro[piperidine-4,7'-thieno[2,3-c]pyran]-2'-carboxylate (5.5 g, 13 mmol), MeOH (22 mL), THF (45 mL) and water (13 mL). Add lithium hydroxide (1 g, 41.76 mmol) to the reaction and stir at ambient temperature for 6 hours. Adjust the pH to 4 with 1 N HCl. Add water and EtOAc and filter off a white solid. Dry in a vacuum oven at 50° C. over 2 days to give the title product (5.25 g, 99%) as a white solid. Mass spectrum (m/z): 412/414/416 (M+H).

Preparation 23

5-(Ethylsulfanyl)pyridine-2-carbonitrile

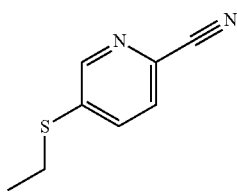

Dissolve 5-bromopyridine-2-carbonitrile (49.42 g, 270.1 mmol) and potassium carbonate (113.5 g, 821.2 mmol) in 1-methyl-2-pyrrolidinone (280 mL) and add ethanethiol (26.4 mL, 356 mmol) in portions over 30 minutes such that the temperature stays below 50° C. Cool the reaction to room temperature and stir overnight. Dilute with EtOAc (1200 mL) and water (2200 mL). Collect the organic layer and wash with brine (3×300 mL), dry the organic layer over sodium sulfate, filter, and concentrate under reduced pressure to give the title compound (44.87 g, 100%) as an off white solid. $^1$H NMR (400.13 MHz, $d_6$-DMSO) δ 8.63 (s, 1H), 7.93 (s, 2H), 3.17 (q, J=7.3, 2H), 1.29 (t, J=7.3, 3H).

Preparation 24

5-(Ethylsulfonyl)pyridine-2-carbonitrile

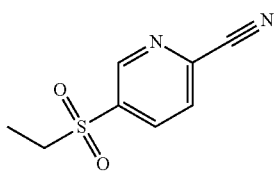

Dissolve 5-(ethylsulfanyl)pyridine-2-carbonitrile (44.36 g, 270.1 mmol) in anhydrous DCM (540 mL) and cool to −20° C. Add 3-chloroperoxybenzoic acid (130 g, 565.0 mmol) in 10-12 gram portions over 1 hour maintaining an internal temperature between 0° C. and −10° C. Stir the reaction mixture in a cold bath allowing to warm to room temperature overnight. Wash with 1 N NaOH (1 L), water, 1 N NaOH (2×500 mL), and brine. Dry the organic layer over sodium sulfate, filter, and concentrate under reduced pressure to give the title compound (49.52 g, 93%) as a white solid. $^1$H NMR (400.13 MHz, $d_6$-DMSO) δ 9.20 (d, J=1.9, 1H), 8.56 (dd, J=2.0, 8.1, 1H), 8.36 (d, J=8.1, 1H), 3.52 (q, J=7.3, 2H), 1.16 (t, J=7.5, 3H).

Preparation 24

1-[5-(Ethylsulfonyl)pyridin-2-yl]methanamine hydrochloride

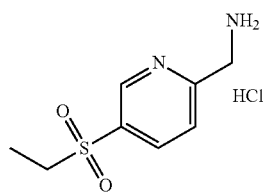

Divide 5-(ethylsulfonyl)pyridine-2-carbonitrile (49.52 g, 252.4 mmol) into three 16.5 g portions. Under $N_2$ in a 2250 mL Parr bottle, add 10% Pd/C (1.65 g, 15.5 mmol) to the vessel and wet with MeOH (750 mL). Add 5-(ethylsulfonyl)pyridine-2-carbonitrile (16.5 g, 84.09 mmol) dissolved in MeOH (750 mL). Add HCl (6 N aqueous, 17.1 ml, 102.6 mmol). Seal the bottle, purge with N2, purge with H2, and pressurize under hydrogen to 68.9 kPa at room temperature for 3 hours. Purge with $N_2$, and then filter the mixture. Repeat on the remaining portions of 5-(ethylsulfonyl)pyridine-2-carbonitrile. Combine all filtrates and concentrate under reduced pressure to give the title compound (59.61 g, 99%) as a beige solid. Mass spectrum (m/z): 201 (M+H−HCl).

Preparation 25

1-[2-(Trifluoromethyl)pyrimidin-5-yl]ethanol

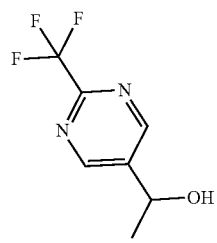

Dissolve 2-(trifluoromethyl)pyrimidine-5-carbaldehyde (11.31 mmol, 1.992 g) in THF (56.56 mL), cool to 0° C., and slowly add methylmagnesium bromide (3 M in $Et_2O$) (33.94 mmol, 11.31 mL). Allow the reaction to warm to room temperature and stir for 2.5 hours. Quench the reaction with 1 N HCl. Add EtOAc and wash with 1 N HCl. Dry the organics over sodium sulfate, filter, and concentrate under Preparation 26

5-(1-Bromoethyl)-2-(trifluoromethyl)pyrimidine

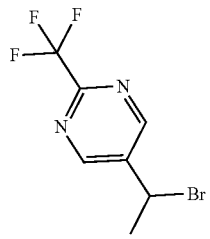

Dissolve 1-[2-(trifluoromethyl)pyrimidin-5-yl]ethanol (1.663 g, 8.655 mmol) and triphenylphosphine (3.405 g, 12.98 mmol) in DCM (86.55 mL) and add NBS (12.98 mmol, 2.311 g) at room temperature. After 3 hours, concentrate the reaction under reduced pressure. Purify the resulting residue via silica gel chromatography eluting with 10% EtOAc/hexanes to give the title compound (1.641 g, 74.34%). $^1$H NMR (400.13 MHz, d$_6$-DMSO) δ 9.26 (s, 2H), 5.63 (q, J=7.0 Hz, 1H), 2.09 (d, J=7.0 Hz, 3H).

Preparation 27

3-(1-Bromopropyl)-2-methyl-6-(trifluoromethyl)pyridine

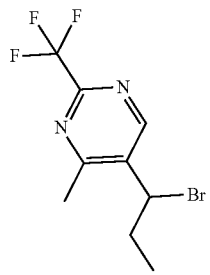

Dissolve 2-methyl-6-(trifluoromethyl)pyridine-3-carbaldehyde (0.25 g, 1.32 mmol) in THF (6 mL) and cool to 0° C. Add ethylmagnesium bromide (3.0 M in Et$_2$O, 1.32 mL, 3.96 mmol) slowly. Stir the mixture for 90 minutes at 0° C. and warm to ambient temperature. Wash the mixture with 1 N HCl, dry the organics over sodium sulfate, filter, and concentrate under reduced pressure. Purify the resulting residue via silica gel chromatography eluting with 30% EtOAc/hexanes to give an intermediate of 1-[6-(trifluoromethyl)-3-pyridyl]propan-1-ol (0.13 g, 0.61 mmol). Dissolve 1-[6-(trifluoromethyl)-3-pyridyl]propan-1-ol (0.13 g, 0.61 mmol) and triphenylphosphine (0.27 g, 1.03 mmol) in DCM (6 mL), then add N-bromosuccinamide (0.18 g, 0.18 mmol). Stir 16 hours at ambient temperature. Concentrate under reduced pressure and purify the resulting residue via silica gel chromatography eluting with 30% EtOAc/hexanes to give the title compound (0.13 g, 76%). $^1$H NMR (400.13 MHz, CDCl$_3$) δ 7.96 (d, J=8.2 Hz, 1H), 7.58 (d, J=8.2 Hz, 1H), 5.09 (m, 1H), 2.70 (s, 3H), 2.34 (m, 1H), 2.21 (m, 1H), 1.09 (t, J=7.3, 3H).

Preparation 28

1-[2-(Tri fluoromethyl)thiazol-5-yl]ethanol

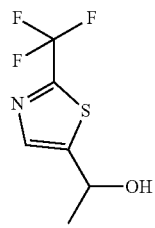

Dissolve 2-(trifluoromethyl)thiazole-5-carbaldehyde (2.00 g, 11.0 mmol) in THF (55 mL) and cool to 0° C., then add methylmagnesium bromide (3.0 M in Et$_2$O, 5.50 mL, 17.0 mmol) slowly. Allow to warm to ambient temperature and stir 2 hours. Quench with 1 N HCl. Add EtOAc and wash with 1 N HCl. Dry the organic extract over sodium sulfate, and filter to give the title compound (2.24 g, 100%) as an oil. $^1$H NMR (400.13 MHz, d$_6$-DMSO) δ 7.97 (s, 1H), 6.08 (d, J=4.8 Hz, 1H), 5.12 (m, 1H), 1.48 (d, J=6.4, 3H).

Preparation 29

5-[1-Bromoethyl]-2-(trifluoromethyl)-1,3-thiazole

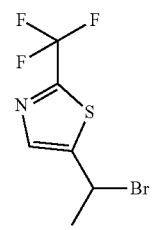

Dissolve 1-[2-(trifluoromethyl)thiazol-5-yl]ethanol (2.24 g, 11.39 mmol) and triphenylphosphine (4.79 g, 17.08 mmol) in DCM (113 mL) then add N-bromosuccinamide (3.04 g, 17.08 mmol). Stir 18 hours at ambient temperature. Concentrate under reduced pressure and purify the resulting residue via silica gel chromatography eluting with 0-20% EtOAc/hexanes to give the title compound (2.35 g, 79%) as a yellow oil. $^1$H NMR (400.13 MHz, d$_6$-DMSO) δ 8.26 (s, 1H), 5.98 (q, J=6.8 Hz, 1H), 2.10 (d, J=6.8, 3H).

Preparation 30

[4-Methyl-2-(trifluoromethyl)pyrimidin-5-yl]methanol

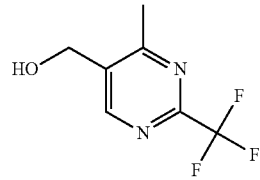

Dissolve ethyl 4-methyl-2-(trifluoromethyl)pyrimidine-5-carboxylate (4.05 g, 17.32 mmol) in dry toluene (87 mL).

Cool the mixture to −10° C. and add diisobutylaluminum hydride (1.0 M in hexanes, 39.8 mL) dropwise. Stir the mixture overnight allowing the mixture to warm to room temperature. Cool the reaction to 0° C. and add sodium sulfate decahydrate (17.75 g, 121.2 mmol) in portions. Warm the mixture to room temperature, stir 3 hours, and filter the mixture through diatomaceous earth rinsing with toluene. Concentrate the combined filtrates under reduced pressure to give the title compound (2.55 g, 69%) as a yellow oil. $^1$H NMR (400.13 MHz, CDCl$_3$) δ 8.82 (s, 1H), 4.83 (s, 2H), 2.62 (s, 3H).

Preparation 31

[4-Methyl-2-(trifluoromethyl)pyrimidin-5-yl]methyl methanesulfonate

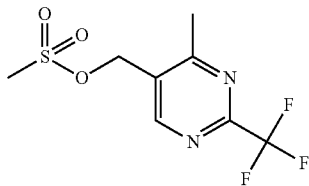 [SMILES: Cc1nc(C(F)(F)F)ncc1COS(C)(=O)=O]

Dissolve [4-methyl-2-(trifluoromethyl)pyrimidin-5-yl] methanol (1.25 g, 5.86 mmol) in DCM (12.5 mL) and add methanesulfonyl chloride (0.2 mL, 3 mmol) followed by trimethylamine (1 mL, 7.10 mmol). After 2.5 hours, add additional methanesulfonyl chloride (0.2 mL, 3 mmol) and trimethylamine (1 mL, 7.10 mmol), then stir for 30 minutes. Dilute with DCM (30 mL) and wash with water followed by brine. Dry the organic layer and concentrate under reduced pressure to give the title compound (1.76 g, 100%). Mass spectrum (m/z): 271 (M+H).

Preparation 32

4-(Hydroxymethyl)-2-methoxy-5-methyl-benzonitrile

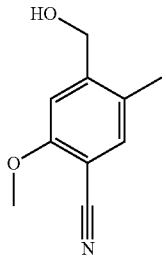

Dissolve 4-formyl-2-methoxy-5-methyl-benzonitrile (204 mg, 1.16 mmol) in EtOH (6 mL) and add sodium borohydride in portions (135 mg, 3.49 mmol). Stir at ambient temperature for 1 hour and concentrate under reduced pressure. Add EtOAc and wash with saturated aqueous ammonium chloride. Wash the aqueous layer with EtOAc, combine the organic layer, dry over sodium sulfate, and concentrate under reduced pressure to give the title compound (186 mg, 1.05 mmol). Mass spectrum (m/z): 178 (M+H).

Preparation 33

(4-Cyano-5-methoxy-2-methyl-phenyl)methyl methanesulfonate

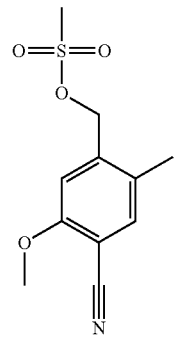 [SMILES: COc1cc(COS(C)(=O)=O)c(C)cc1C#N]

Dissolve 4-(hydroxymethyl)-2-methoxy-5-methyl-benzonitrile (0.19 g, 1.05 mmol) and trimethylamine (0.4 mL, 3.0 mmol) in THF (3.5 mL) and add methanesulfonyl chloride (0.1 mL, 1.0 mmol) and stir at ambient temperature for 2 hours. Concentrate the mixture under reduced pressure and redissolve in EtOAc. Wash with water, dry the organic layer over sodium sulfate, filter, and concentrate under reduced pressure to give the title compound (0.25 g, 78%) which is used without further purification. Mass spectrum (m/z): 271 (M+H+H$_2$O).

Preparation 34

[2-Methyl-6-(trifluoromethyl)-3-pyridyl]methyl methanesulfonate

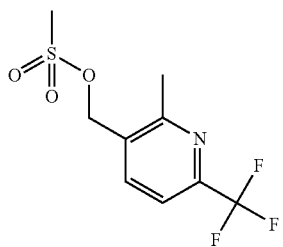 [SMILES: Cc1nc(C(F)(F)F)ccc1COS(C)(=O)=O]

Dissolve [2-methyl-6-(trifluoromethyl)-3-pyridyl]methanol (170 mg, 0.82 mmol) in DCM (2.5 mL) and cool to 0° C. Add trimethylamine (0.23 mL, 1.64 mmol) dropwise followed by methanesulfonylchloride (0.076 mL, 0.98 mmol), warm to ambient temperature, and stir 30 minutes. Add water and DCM. Wash the organic layer with water, dry over sodium sulfate, filter, and concentrate under reduced pressure to give the title compound (0.17 g, 77%) which is used without further purification. The material is a mixture of the title compound and 3-(chloromethyl)-2-methyl-6-(trifluoromethyl)pyridine. Mass spectrum (m/z): 270 (M+H).

Preparation 35

1-[5-Fluoro-6-(trifluoromethyl)-3-pyridyl]ethanone

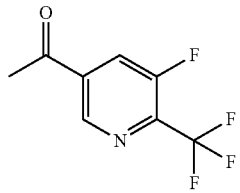

Dissolve 5-bromo-3-fluoro-2-(trifluoromethyl)pyridine (0.84 mL, 6.1 mmol) in 1,4-dioxane (31 mL) and add tetrakis(triphenylphosphine)palladium(0) (0.36 g, 0.31 mmol) followed by trimethylamine (1.3 mL, 9.3 mmol). Degas the mixture by bubbling in $N_2$ for 10 minutes, then add tributyl(1-ethoxyvinyl)stannane (2.7 mL, 8.0 mmol) and heat to 100° C. for 4 hours. Cool the reaction to ambient temperature, add 1 N HCl (25 mL, 25 mmol), and stir overnight. Quench the mixture with aqueous saturated sodium bicarbonate, then extract with EtOAc, dry over sodium sulfate, filter, and concentrate under reduced pressure. Purify using silica gel flash chromatography eluting with EtOAc and hexanes. Redissolve the material in DCM, add saturated aqueous potassium fluoride (25 mL), and stir 1 hour. Separate the layers and wash the organic layer with brine, dry over sodium sulfate, filter, and concentrate under reduced pressure to give the title compound (1.3 g, 100%). $^1$H NMR (400.13 MHz, $d_6$-DMSO) δ 9.05 (s, 1H), 8.49 (d, J=10.8 Hz, 1H), 2.69 (s, 3H).

Preparation 36

1-[5-Fluoro-6-(trifluoromethyl)-3-pyridyl]ethanol

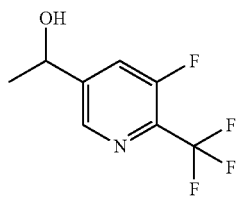

Dissolve 1-[5-fluoro-6-(trifluoromethyl)-3-pyridyl]ethanone (1.4 g, 6.8 mmol) in MeOH (35 mL) and add sodium borohydride (100 mg, 2.6 mmol) in portions over 15 minutes, then stir at ambient temperature for 1 hour. Add saturated ammonium chloride (50 mL) and water (50 mL), then extract with DCM (2×100 mL). Combine the organic layers, dry over sodium sulfate, filter, and concentrate under reduced pressure to give the title compound (1.2 g, 88%). Mass spectrum (m/z): 210 (M+H).

Preparation 37

1-[5-Fluoro-6-(trifluoromethyl)-3-pyridyl]ethyl methanesulfonate

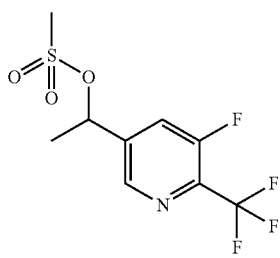 [SMILES: CC(OS(C)(=O)=O)c1cnc(C(F)(F)F)c(F)c1]

Dissolve 1-[5-fluoro-6-(trifluoromethyl)-3-pyridyl]ethanol (1.3 g, 6.2 mmol) in THF (31 mL) and trimethylamine (2.2 mL, 16 mmol). Add a solution of methanesulfonylchloride (0.54 mL, 6.8 mmol) in THF (31 mL) and stir at ambient temperature for 2 hours. Concentrate under reduced pressure to give the title compound (4.4 g, 77%) which still contains trimethylamine salts. Use the material without further purification. Mass spectrum (m/z): 288 (M+H).

Preparation 38

Methyl 5-fluoro-6-(tri fluoromethyl)pyridine-3-carboxylate

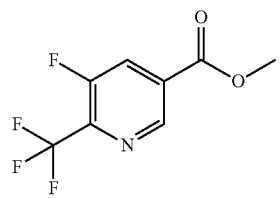

Dissolve 5-bromo-3-fluoro-2-(trifluoromethyl)pyridine (1.00 g, 3.97 mmol) in anhydrous MeOH (12 mL)/ACN (18 mL). Add trimethylamine (1.5 mL, 11 mmol), palladium (II) acetate (93 mg, 0.39 mmol), and 1,1'-bis(diphenylphosphino)ferrocene (276 mg, 0.48 mmol), then seal and purge with CO (gas). Pressurize to 689 kPa with CO and heat to 85° C. for 1.5 hours and cool to ambient temperature. Filter through diatomaceous earth and concentrate the filtrate under reduced pressure. Purify using silica gel flash chromatography eluting with 0-100% EtOAc in hexanes to give the title compound (0.67 g, 73%) as a white solid. $^1$H NMR (400.13 MHz, $d_6$-DMSO) δ 9.05 (s, 1H), 8.50 (d, J=10.5 Hz, 1H), 3.93 (s, 3H).

Preparation 39

[5-Fluoro-6-(trifluoromethyl)-3-pyridyl]methanol

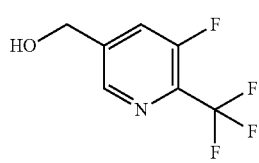 [SMILES: OCc1cnc(C(F)(F)F)c(F)c1]

Dissolve methyl 5-fluoro-6-(trifluoromethyl)pyridine-3-carboxylate (0.60 g 2.69 mmol) in toluene (30 mL), cool to 0° C., and add diisobutylaluminum hydride (1.0 M in hexanes, 5.4 mL, 5.40 mmol). Stir at 0° C. for 2 hours, then allow to warm to ambient temperature and stir 16 hours. Cool to 0° C. and add additional diisobutylaluminum hydride (1.0 M in hexanes, 5.4 mL, 5.40 mmol). After 4 hours, allow the reaction to warm to ambient temperature and add sodium sulfate (300 mg, 2.11 mmol). Stir 1 hour, filter, and concentrate under reduced pressure to give the title compound (0.27 g, 51%) as a white solid. Mass spectrum (m/z): 196 (M+H).

Preparation 40

[5-Fluoro-6-(trifluoromethyl)-3-pyridyl]methyl methanesulfonate

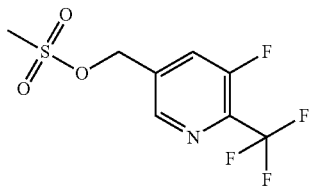 [SMILES: CS(=O)(=O)OCc1cnc(C(F)(F)F)c(F)c1]

Dissolve [5-fluoro-6-(trifluoromethyl)-3-pyridyl]methanol (268 mg, 1.37 mmol) and trimethylamine (0.35 mL, 2.50 mmol) in THF (15 mL) and add methanesulfonyl chloride (0.12 mL, 2.30 mmol). Stir for 2 hours at ambient temperature and concentrate under reduced pressure to give the crude title compound (987 mg, 99%) a white solid. Mass spectrum (m/z): 274 (M+H).

Preparation 41

4-(1-Bromoethyl)-2-fluoro-benzonitrile

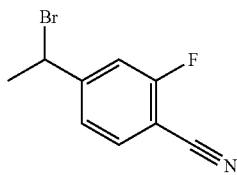

Dissolve 2-fluoro-4-(1-hydroxyethyl)benzonitrile (0.62 g, 3.77 mmol) and triphenylphosphine (1.48 g, 5.66 mmol) in DCM (37 mL) and add NBS (1.01 g, 5.66 mmol). Stir the mixture overnight at ambient temperature, concentrate under reduced pressure, and purify using silica gel flash chromatography eluting with a gradient of 0-40% EtOAc in hexanes to give the title compound (0.63 g, 73%) as a pale yellow oil. $^1$H NMR (400.13 MHz, $d_6$-DMSO) δ 7.95 (m, 1H), 7.73 (d, J=10.6 Hz, 1H), 7.57 (d, J=8.1 Hz, 1H), 5.54 (q, J=6.8 Hz, 1H), 1.99 (d, J=6.8 hz, 3H).

Preparation 42

Methyl 4-[(Z)—N'-hydroxycarbamimidoyl]-2-methyl-benzoate

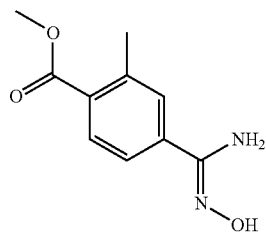

Combine methyl 4-cyano-2-methyl-benzoate (1.00 g, 5.71 mmol) and hydroxylamine hydrochloride (0.59 g, 8.56 mmol) in MeOH (29 mL), add DIPEA (1.6 mL, 9.13 mmol) and heat at 70° C. overnight. Cool to ambient temperature, concentrate under reduced pressure, add water, and adjust the pH to 5 with 1 N HCl. Extract with 10% isopropylalcohol/DCM (2×). Combine the organic layers, dry over sodium sulfate, filter, and concentrate under reduced pressure to give the title compound (1.19 g, 100%). Mass spectrum (m/z): 209 (M+H).

Preparation 43

Methyl 2-methyl-4-(5-methyl-1,2,4-oxadiazol-3-yl)benzoate

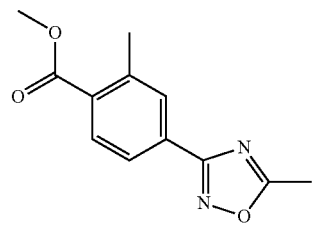 [SMILES: COC(=O)c1ccc(-c2noc(C)n2)cc1C]

Combine methyl 4-[(Z)—N'-hydroxycarbamimidoyl]-2-methyl-benzoate (0.34 g, 1.66 mmol) and acetic anhydride (5.4 g, 51.10 mmol) in a screw cap vial, seal, and heat to 100° C. overnight. Cool to ambient temperature, add Et$_2$O, wash with water, dry over sodium sulfate, filter, and concentrate under reduced pressure. Purify using silica gel flash chromatography eluting with a gradient of 20-50% EtOAc in hexanes to give the title compound (0.37 g, 97%). Mass spectrum (m/z): 233 (M+H).

Preparation 44

[2-Methyl-4-(5-methyl-1,2,4-oxadiazol-3-yl)phenyl]methanol

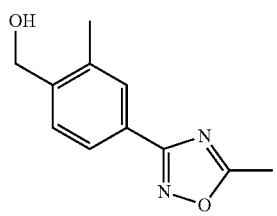

Combine methyl 2-methyl-4-(5-methyl-1,2,4-oxadiazol-3-yl)benzoate (0.37 g, 1.61 mmol) in DCM (16 mL), cool to 0° C., and add diisobutylaluminum hydride (1.0 M in THF, 6.2 mL, 6.2 mmol). Stir 10 minutes at 0° C., warm to ambient temperature, and stir overnight. Quench with saturated ammonium chloride, add 1 N HCl, and extract with EtOAc (2×). Combine the organic extracts, dry over sodium sulfate, and concentrate under reduced pressure to give the title compound (0.13 g, 40%). Mass spectrum (m/z): 205 (M+H).

Preparation 45

[2-Methyl-4-(5-methyl-1,2,4-oxadiazol-3-yl)phenyl]methyl methanesulfonate

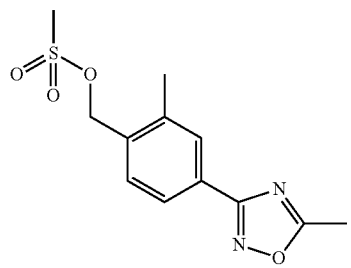 [SMILES: Cc1nc(-c2ccc(COS(C)(=O)=O)c(C)c2)no1]

Combine [2-methyl-4-(5-methyl-1,2,4-oxadiazol-3-yl)phenyl]methanol (0.13 g, 0.64 mmol) and trimethylamine (0.18 mL, 1.28 mmol) in THF (2.5 mL), cool to 0° C., and add methanesulfonic anhydride (0.14 g, 0.77 mmol). Stir overnight allowing the reaction to warm to ambient temperature. Add Et$_2$O, wash with water followed by brine, dry over sodium sulfate, filter, and concentrate under reduced pressure to give the title compound (0.18 g, 51%). Mass spectrum (m/z): 283 (M+H).

Preparation 46

[4-methyl-2-(trifluoromethyl)pyrimidin-5-yl]methanol

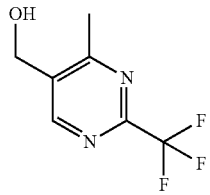

Dissolve 4-methyl-2-(trifluoromethyl)pyrimidine-5-carboxylic acid (1.5 g, 7.3 mmol) in 1,2-dimethoxyethane (36 mL) and cool to −15° C. Add 4-methylmorpholine (0.81 mL, 7.3 mmol) followed by isobutyl chloroformate (0.95 mL, 7.3 mmol) and stir 15 minutes. Filter the solution and cool the filtrate to 0° C. Add a solution of sodium borohydride (0.41 g, 10.8 mmol) in water (5 mL). Stir 5 minutes, add water (35 mL) and EtOAc. Separate and collect the organic layer, wash with brine, dry over sodium sulfate, filter, and concentrate to dryness to give the title compound (1.16 g, 83%) as a yellow oil. Mass spectrum (m/z): 193 (M+H).

Preparation 47

4-Methyl-2-(trifluoromethyl)pyrimidine-5-carbaldehyde

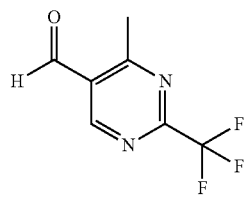

Dissolve [4-methyl-2-(trifluoromethyl)pyrimidin-5-yl]methanol (1.16 g, 6.04 mmol) in DCM (60 mL) and cool to 0° C. Add manganese dioxide (2.67 g, 30.7 mmol), warm to ambient temperature, and stir for 18 hours. Filter the resulting mixture through diatomaceous earth and concentrate the filtrate under reduced pressure. Purify with silica gel chromoatography eluting with a gradient of 0-5% MeOH in DCM to give the title compound (0.26 g, 22%) as a clear oil. $^1$H NMR (400.13 MHz, d$_6$-DMSO) δ 10.32 (s, 1H), 9.31 (s, 1H), 2.87 (s, 3H).

Preparation 48

1-[4-Methyl-2-(trifluoromethyl)pyrimidin-5-yl]ethanol

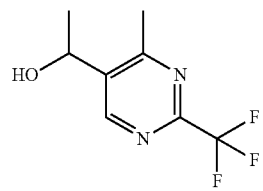

Dissolve 4-methyl-2-(trifluoromethyl)pyrimidine-5-carbaldehyde (700 mg, 3.68 mmol) in Et$_2$O (37 mL) and cool to 0° C. Add drop wise a solution of methylmagnesium bromide (3.0 M in Et$_2$O, 1.2 mL, 3.6 mmol) and stir at 0° C. for 2 hours. Quench with saturated ammonium chloride and add water. Extract the aqueous layer with Et$_2$O (4×), combine the organic extracts, dry over sodium sulfate, filter, and concentrate under reduced pressure to give the title compound (0.68 g, 89%) as a yellow oil. Mass spectrum (m/z): 207 (M+H).

Preparation 49

1-[4-Methyl-2-(trifluoromethyl)pyrimidin-5-yl]ethyl methanesulfonate

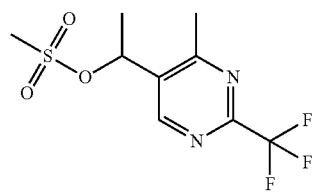 [SMILES: Cc1nc(C(F)(F)F)ncc1C(C)OS(C)(=O)=O]

Dissolve 1-[4-methyl-2-(trifluoromethyl)pyrimidin-5-yl]ethanol (0.68 g, 3.3 mmol) and TEA (1.2 mL, 8.6 mmol) in THF (17 mL). Add methanesulfonyl chloride and stir at ambient temperature 1 hour. Concentrate the mixture under reduced pressure to give the crude title compound (2.2 g, 30% purity, 71% yield) which is used without further purification. Mass spectrum (m/z): 285 (M+H).

Preparation 50 tert-Butyl (5'S)-2'-{[4-(ethylsulfonyl)benzyl]carbamoyl}-5'-methyl-4',5'-dihydro-1H-spiro[piperidine-4,7'-thieno[2,3-c]pyran]-1-carboxylate

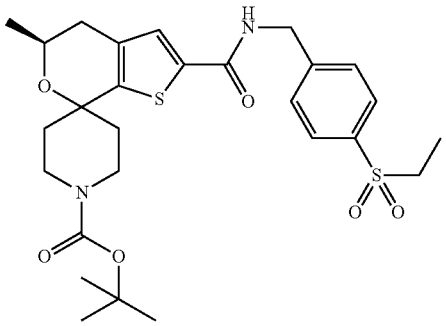 [SMILES: CCS(=O)(=O)c1ccc(CNC(=O)c2cc3c(s2)C2(CCN(C(=O)OC(C)(C)C)CC2)O[C@@H](C)C3)cc1]

Add DIPEA (7.4 mL, 42 mmol), HOBT (1.80 g, 13 mmol), and EDCI (3.13 g, 16.3 mmol) to a slurry of (5'S)-1-(tert-butoxycarbonyl)-5'-methyl-4',5'-dihydrospiro[piperidine-4,7'-thieno[2,3-c]pyran]-2'-carboxylic acid (4.44 g, 12.1 mmol) and 4-(ethylsulfonylphenyl)methanamine (3.42 g, 14.5 mmol) in DCM (100 mL) and stir at ambient temperature for 16 hours. Add water and extract with DCM (3×100 mL). Combine the DCM extracts, dry over sodium sulfate, filter, and concentrate under reduced pressure. Purify the residue by silica gel flash chromatography eluting with 50-100% EtOAc in hexanes to give the title compound (4.24 g, 64%) as a white solid. Mass spectrum (m/z): 548 (M+H), 571 (M+Na).

Prepare the following compounds essentially by the method of Preparation 50 using the appropriate amine.

TABLE 7

| Prep No. | Chemical Name | Structure | ES/MS (m/z) (M + 1) |
|---|---|---|---|
| 51 | tert-Butyl 2'-{[4-(methylsulfonyl)benzyl]carbamoyl}-4',5'-dihydro-1H-spiro[piperidine-4,7'-thieno[2,3-c]pyran]-1-carboxylate | 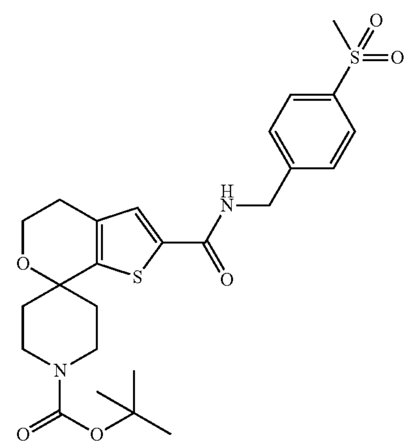 [SMILES: CC(C)(C)OC(=O)N1CCC2(CC1)OCCc1cc(C(=O)NCc3ccc(S(C)(=O)=O)cc3)sc12] | 519.2 (M − H) |
| 52 | tert-Butyl 2'{[4-(ethylsulfonyl)benzyl]carbamoyl}-4',5'-dihydro-1H-spiro[piperidine-4,7'-thieno[2,3-c]pyran]-1-carboxylate | 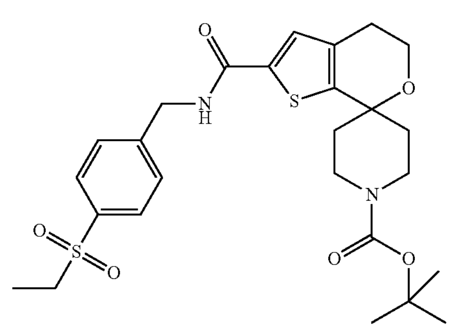 [SMILES: CCS(=O)(=O)c1ccc(CNC(=O)c2cc3c(s2)C2(CCN(C(=O)OC(C)(C)C)CC2)OCC3)cc1] | 535 (M + H) 557 (M + Na) |

TABLE 7-continued

| Prep No. | Chemical Name | Structure | ES/MS (m/z) (M + 1) |
|---|---|---|---|
| 53 | tert-Butyl (5'R)-2'-{[4-(ethylsulfonyl)benzyl]carbamoyl}-5'-methyl-4',5'-dihydro-1H-spiro[piperidin-4,7'-thieno[2,3-c]pyran]-1-carboxylate | 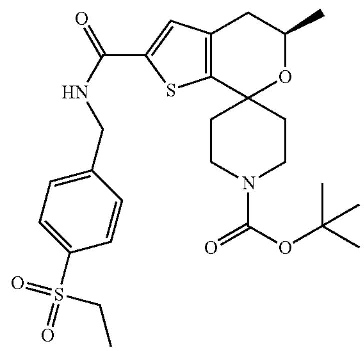 [SMILES: CCS(=O)(=O)c1ccc(CNC(=O)c2cc3c(s2)C2(CCN(C(=O)OC(C)(C)C)CC2)O[C@H](C)C3)cc1] | 549 (M + H) 571 (M + Na) |

Preparation 54 tert-Butyl (5'S)-2'-({[5-(ethylsulfonyl)pyridin-2-yl]methyl}carbamoyl)-5'-methyl-4',5'-dihydro-1H-spiro[piperidine-4,7'-thieno[2,3-c]pyran]-1-carboxylate

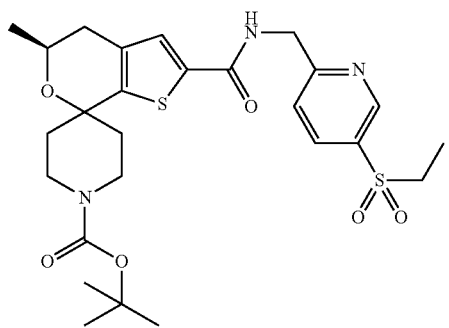 [SMILES: CCS(=O)(=O)c1ccc(CNC(=O)c2cc3c(s2)C2(CCN(C(=O)OC(C)(C)C)CC2)O[C@@H](C)C3)nc1]

Dissolve 1-[5-(ethylsulfonyl)pyridin-2-yl]methanamine hydrochloride (2.86 g, 10.5 mmol), (5'S)-1-tert-butoxycarbonyl)-5'-methyl-4',5'dihydrospiro[piperidine-4,7'-thieno[2,3-c]pyran]-2'-carboxylic acid (3.50 g, 9.52 mmol), and HOBt (1.44 g, 10.5 mmol) in anhydrous THF (100 mL) and DMF (50 mL). Add DIPEA (4.98 mL, 28.6 mmol) followed by EDCI (2.01 g, 10.5 mmol) and allow to stir at room temperature overnight. Concentrate under reduced pressure to ~40% volume, then add EtOAc. Wash with saturated sodium bicarbonate (2x), water (2x), brine (2x), dry the organic layer over sodium sulfate, filter, and concentrate under reduced pressure. Chromatograph on silica gel with 80% EtOAc/hexanes to give the title compound (4.51 g, 86%) as a grey foam. Mass spectrum (m/z): 550 (M+H).

Preparation 55 tert-Butyl 2'-{[4-(ethyl sulfonyl)benzyl)carbamoyl}-5'-methyl-4',5'-dihydro-1H-spiro[piperidine-4,7'-thieno[2,3-c]pyran]-1-carboxylate

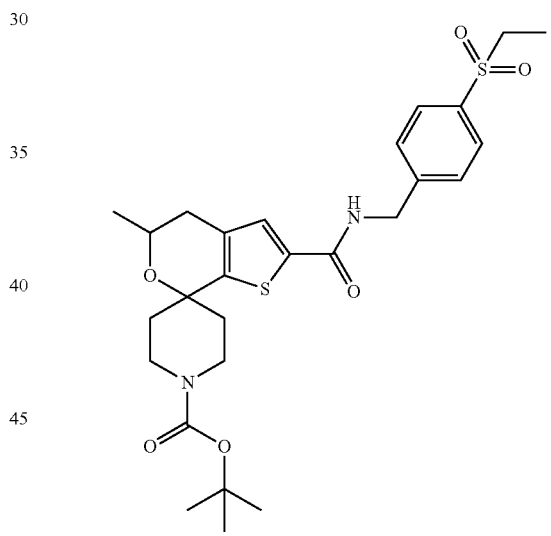

Add T3P® (1.67 mol/L in EtOAc, 15 mL, 26 mmol) to a solution of (4-ethylsulfonylphenyl)methanamine, hydrochloride (4.8 g, 20 mmol), 1-(tert-butoxycarbonyl)-5'-methyl-4',5'-dihydrospiro[piperidine-4,7'-thieno[2,3-c]pyran]-2'-carboxylic acid (6.6 g, 17 mmol) and TEA (9.5 mL, 68 mmol,) in DCM (66 mL) at 0° C. and stir at room temperature for 16 hours. Add excess (4-ethylsulfonylphenyl)methanamine, hydrochloride (0.80 g, 3.4 mmol) and T3P® (1.67 mol/L in EtOAc, 2.0 mL, 3.4 mmol) to the reaction mixture cooled at 0° C. and stir at room temperature for 30 minutes. Dilute with DCM (100 mL) and quench with a saturated solution of NaHCO3 (100 mL). Stir for 15 minutes then filter the organic layer through a phase separator and concentrate under reduced pressure. Purify the residue by silica gel flash chromatography eluting with MeOH: DCM (0:100 to 5:95) to give the title compound (7.45 g, 76%) as an off-white solid. Mass spectrum (m/z): 548 (M+H), 571 (M+Na).

Preparation 56 tert-Butyl 2'-({[5-(ethylsulfonyl)pyridin-2-yl]methyl}carbamoyl)-5'-methyl-4',5'-dihydro-1H-spiro[piperidine-4,7'-thieno[2,3,c]pyran]-1-carboxylate

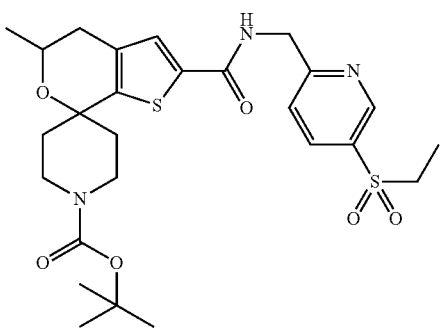 [SMILES: CCS(=O)(=O)c1ccc(CNC(=O)c2cc3c(s2)C2(CCN(C(=O)OC(C)(C)C)CC2)OC(C)C3)nc1]

Dissolve 1-[5-(ethylsulfonyl)pyridin-2-yl]methanamine hydrochloride (3.1 g, 13 mmol), 1-(tert-butoxycarbonyl)-5'-methyl-4',5'-dihydrospiro[piperidine-4,7'-thieno[2,3-c]pyran]-2'-carboxylic acid (3.9 g, 10 mmol) in anhydrous DCM (52 mL). Cool to 0° C. and add trimethylamine (10 mL, 73 mmol) dropwise followed by a 1.67 M solution of T3P® (8.6 g, 14 mmol) in EtOAc. Allow the mixture to warm to room temperature and stir overnight. Carefully add water (50 mL) and stir 10 minutes at room temperature. Extract the aqueous layer with DCM (2×), then combine the organic layers. Wash the organic layers with brine, dry over sodium sulfate, filter, and concentrate under reduced pressure. Purify the crude material with silica gel chromatography eluting with a 50% to 100% EtOAc/hexanes gradient to give the title compound (4.89 g, 83%) as a yellow foam. Mass spectrum (m/z): 550 (M+H).

Preparation 57 tert-Butyl (5'S)-2'-({[5-(ethylsulfonyl)pyridin-2-yl]methyl}carbamoyl)-5'-methyl-4',5'-dihydro-1H-spiro[piperidine-4,7'-thieno[2,3,c]pyran]-1-carboxylate

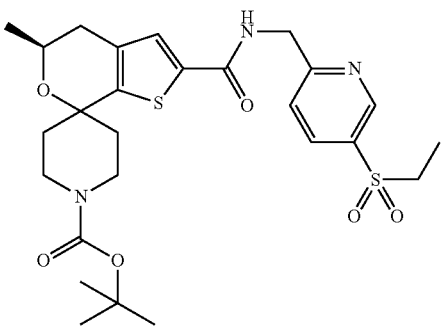 [SMILES: CCS(=O)(=O)c1ccc(CNC(=O)c2cc3c(s2)C2(CCN(C(=O)OC(C)(C)C)CC2)O[C@@H](C)C3)nc1]

Dissolve 1-[5-(ethylsulfonyl)pyridin-2-yl]methanamine hydrochloride (2.86 g, 10.5 mmol), (5'S)-1-tert-butoxycarbonyl)-5'-methyl-4',5'dihydrospiro[piperidine-4,7'-thieno[2,3-c]pyran]-2'-carboxylic acid (3.50 g, 9.52 mmol), and HOBT (1.44 g, 10.5 mmol) in anhydrous THF (100 mL) and dimethylformamide (50 mL). Add DIPEA (4.98 mL, 28.6 mmol) followed by 1-(3-dimethylaminopropy)-3-ethylcarbodiimide hydrochloride and allow to stir at room temperature overnight. Concentrate under reduced pressure to ~40% volume, then add EtOAc. Wash with saturated sodium bicarbonate (2×), water (2×), brine (2×), dry the organic layer over sodium sulfate, filter, and concentrate under reduced pressure. Chromatograph on silica gel with 80% EtOAc/hexanes to give the title compound (4.51 g, 86%) as a grey foam. Mass spectrum (m/z): 550 (M+H).

Preparation 58 tert-Butyl 2-[(5-ethylsulfonyl-2-pyridyl)methylcarbamoyl]-4-methyl-spiro[4,5-dihydrothieno[2,3-c]pyran-7,4'-piperidine]-1'-carboxylate

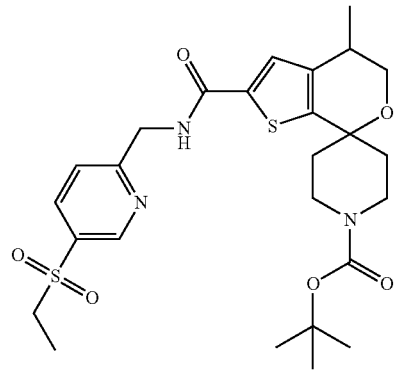 [SMILES: CCS(=O)(=O)c1ccc(CNC(=O)c2cc3c(s2)C2(CCN(C(=O)OC(C)(C)C)CC2)OCC3C)nc1]

Add together tert-butyl 2-bromo-4-methyl-spiro[4,5-dihydrothieno[2,3-c]pyran-7,4'-piperidine]-1'-carboxylate (5.68 g, 11.6 mmol), 1-[5-(ethylsulfonyl)pyridin-2-yl]methanamine hydrochloride (3.29 g, 13.9 mmol) and DIPEA (5.05 mL, 28.9 mmol) in toluene (56.8 mL) followed by palladium (II) acetate (85.8 mg, 0.382 mmol) and 4,5-bis-(diphenylphosphino)-9,9-dimethylxanthene (0.429 g, 0.741 mmol). Degas the reaction and refill with CO (434 kPa) then heat to 90° C. overnight. Filter through a pad of diatomaceous earth, wash with EtOAc (2×120 mL) and concentrate the solvents to give a brown foam. Purify by silica gel flash chromatography eluting with DCM/MeOH (100:0 to 95:5) to give the title product (5.33 g, 71%) as a brown foam. Mass spectrum (m/z): 572 (M+Na).

Prepare the following compound essentially by the method of Preparation 58 using the appropriate amine.

TABLE 8

| Prep No. | Chemical Name | Structure | ES/MS (m/z) (M + 1) |
|---|---|---|---|
| 59 | tert-Butyl (5'S)-5'-methyl-2'-{[4-(methylsulfonyl)benzyl]carbamoyl}-4',5'-dihydro-1H-spiro[piperidine-4,7'-thieno[2,3-c]pyran]-1-carboxylate | 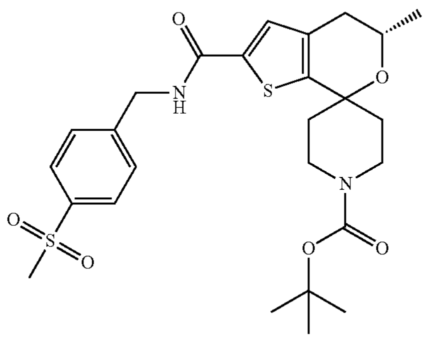 [SMILES: C[C@H]1Cc2cc(C(=O)NCc3ccc(S(C)(=O)=O)cc3)sc2C2(CCN(C(=O)OC(C)(C)C)CC2)O1] | 535 (M + H) |

Preparation 60 tert-Butyl (4'S)-2'-({[5-(ethylsulfonyl)pyridin-2-yl]methyl}carbamoyl)-4'-methyl-4',5'-dihydro-1H-spiro[piperidine-4,7'-thieno[2,3-c]pyran]-1-carboxylate

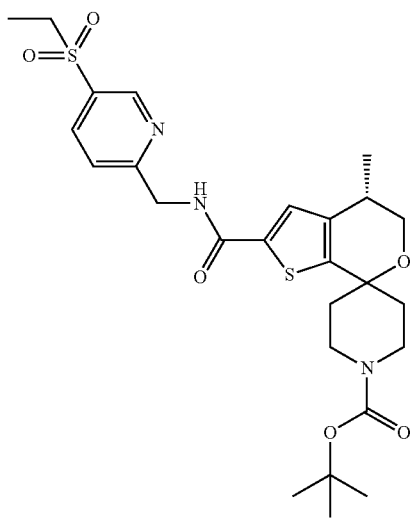 [SMILES: CCS(=O)(=O)c1ccc(CNC(=O)c2cc3c(s2)C2(CCN(C(=O)OC(C)(C)C)CC2)OC[C@H]3C)nc1]

Cool a solution of tert-butyl (4'S)-4'-methyl-4',5'-dihydro-1H-spiro[piperidine-4,7'-thieno[2,3-c]pyran]-1-carboxylate (2.78 g, 8.59 mmol) in ACN (56 mL) to 0° C. then add NBS (2.2 g, 12.35 mmol) and DMAP (107 mg, 0.865 mmol) and stir at room temperature. After 1 hour, concentrate to dryness and take up the residue in DCM. Wash with a saturated aqueous solution of sodium thiosulfate then brine. Collect the organic, dry with sodium sulfate, filter, and concentrate to dryness to give crude tert-butyl (4S)-2-bromo-4-methyl-spiro[4,5-dihydrothieno[2,3-c]pyran-7,4'-piperidine]-1'-carboxylate. Mass spectrum 424/426 (M+Na). Charge a pressure vessel with tert-butyl (4S)-2-bromo-4-methyl-spiro[4,5-dihydrothieno[2,3-c]pyran-7,4'-piperidine]-1'-carboxylate (3.46 g, 8.59 mmol), (5-ethylsulfonyl-2-pyridyl)methanamine;hydrochloride (2.44 g, 10.3 mmol) and DIPEA (3.75 mL, 21.5 mmol) in toluene (34.6 mL) followed by palladium (II) acetate (63.6 mg, 0.283 mmol) and 4,5-bis-(diphenylphosphino)-9,9-dimethylxanthene (0.328 g, 0.55 mmol). Degas the reaction and refill with carbon monoxide (434 kPa) then heat to 85° C. overnight. Filter through a pad of diatomaceous earth, wash with EtOAc (2×120 mL) and concentrate the solvents under reduced pressure. Purify by silica gel flash chromatography eluting with DCM/MeOH (100:0 to 95:5) to give the title product (2.64 g, 56%) as a brown foam. Mass spectrum (m/z): 494 (M-t-butyl), 572 (M+Na).

Preparation 61

N-{[5-(Ethylsulfonyl)pyridin-2-yl]methyl}-5'-methyl-4',5'-dihydrospiro[piperidine-4,7'-thieno[2,3-c]pyran]-2'-carboxamide dihydrochloride

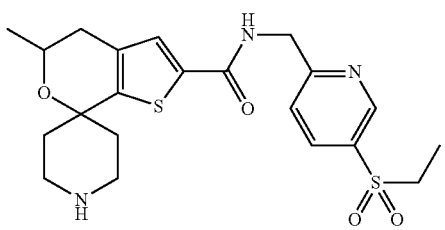

2HCl

Dissolve tert-butyl 2'-({[5-(ethylsulfonyl)pyridin-2-yl]methyl}carbamoyl)-5'-methyl-4',5'-dihydro-1H-spiro[piperidine-4,7'-thieno[2,3,c]pyran]-1-carboxylate (0.95 g, 1.68 mmol) in MeOH (10 mL) and add 4 M HCl in dioxane (4.5 mL, 18 mmol). Stir at room temperature for 1 hour, then concentrate under reduced pressure to give the title compound (0.86 g, 100%) as a white solid. Mass spectrum (m/z): 450 (M+H-2HCl).

Preparation 62

(5'S)—N-{[5-(Ethylsulfonyl)pyridin-2-yl]methyl}-5'-methyl-4',5',dihydrospiro[piperidine-4,7'-thieno[2,3,c]pyran]-2'-carboxamide dihydrochloride

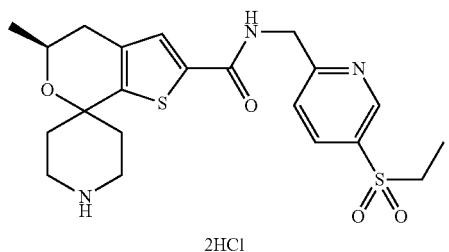 [SMILES: CCS(=O)(=O)c1ccc(CNC(=O)c2cc3c(s2)C2(CCNCC2)O[C@@H](C)C3)nc1]

2HCl

Dissolve tert-butyl (5'S)-2'-({[5-(ethylsulfonyl)pyridin-2-yl]methyl}carbamoyl)-5'-methyl-4',5'-dihydro-1H-spiro[piperidine-4,7'-thieno[2,3,c]pyran]-1-carboxylate (1.14 g, 2.0 mmol) in 1,4 dioxane (10 mL) and MeOH (5 mL). Add 4 M HCl in dioxane (5.0 mL, 20 mmol) and stir at room temperature for 2 hours. Concentrate to about 10 mL, then add Et$_2$O and stir vigorously overnight. Add hexanes, filter, and rinse with hexanes to give the title compound (0.99 g, 91%) as a light yellow solid. Mass spectrum (m/z): 450 (M+H-2HCl).

Preparation 63

(5'S)—N-[4-(Ethylsulfonyl)benzyl]-5'-methyl-4',5'-dihydrospiro[piperidine-4,7'-thieno[2,3-c]pyran]-2'-carboxamide hydrochloride

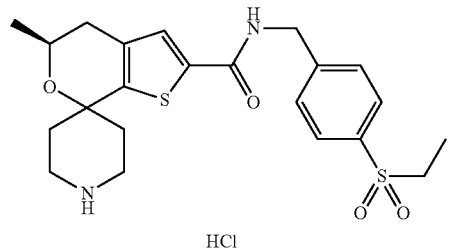 [SMILES: CCS(=O)(=O)c1ccc(CNC(=O)c2cc3c(s2)C2(CCNCC2)O[C@@H](C)C3)cc1 ; Cl]

HCl

Add HCl (4 mol/L in 1,4-dioxane, 15.6 mL, 62.4 mmol) to a solution of tert-butyl (5'S)-2'-{[4-(ethylsulfonyl)benzyl)carbamoyl}-5'-methyl-4',5'-dihydro-1H-spiro[piperidine-4,7'-thieno[2,3-c]pyran]-1-carboxylate (8.54 g, 15.57 mmol) in dry DCM (50 mL) and heat the mixture at ambient temperature for 1.5 hours. Filter the resulting solid and rinse with DCM. Dry the solid under vacuum to give the title compound (6.57 g, 87% crude). Mass spectrum (m/z): 449 (M+H−HCl).

Prepare the following compounds essentially by the method of Preparation 63.

TABLE 9

| Prep. No. | Chemical Name | Structure | ES/MS (m/z) (M + 1) |
|---|---|---|---|
| 64 | N-[4-(Methylsulfonyl)benzyl]-4',5'-dihydrospiro[piperidine-4,7'-thieno[2,3-c]pyran]-2'-carboxamide hydrochloride | 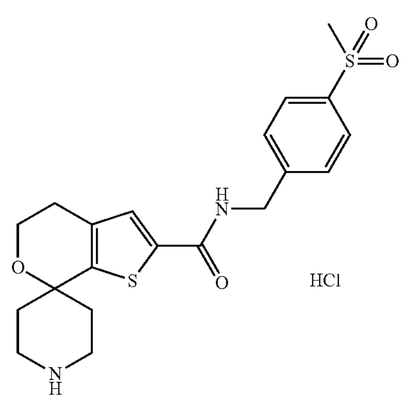 [SMILES: CS(=O)(=O)c1ccc(CNC(=O)c2cc3c(s2)C2(CCNCC2)OCC3)cc1 ; Cl] | 421.0 (M + H − HCl) |
| 65 | N-[4-(Ethylsulfonyl)benzyl]-4',5'-dihydrospiro[piperidine-4,7'-thieno[2,3-c]pyran]-2'-carboxamide hydrochloride | 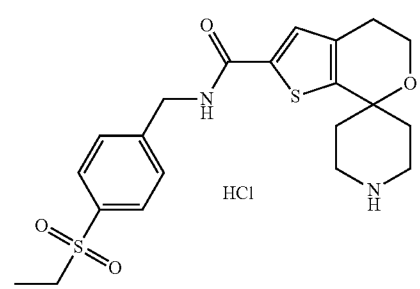 [SMILES: CCS(=O)(=O)c1ccc(CNC(=O)c2cc3c(s2)C2(CCNCC2)OCC3)cc1 ; Cl] | 435 (M + H − HCl) |

TABLE 9-continued

| Prep. No. | Chemical Name | Structure | ES/MS (m/z) (M + 1) |
|---|---|---|---|
| 66 | N-[4-(Ethylsulfonyl)benzyl]-5'-methyl-4',5'-dihydrospiro[piperidine-4,7'-thieno[2,3-c]pyran]-2'-carboxamide hydrochloride | 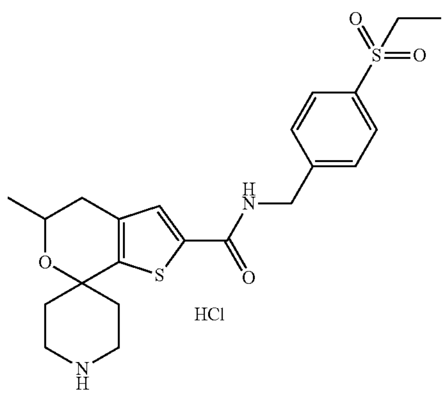 [SMILES: CCS(=O)(=O)c1ccc(CNC(=O)c2cc3c(s2)C2(CCNCC2)OC(C)C3)cc1 ; Cl] | 449 (M + H − HCl) |
| 67 | (5'R)-N-[4-(Ethylsulfonyl)benzyl]-5'-methyl-4',5'-dihydrospiro[piperidine-4,7'-thieno[2,3-c]pyran]-2'-carboxamide hydrochloride | 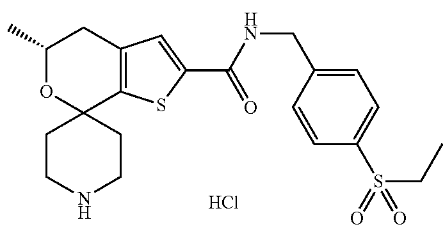 [SMILES: CCS(=O)(=O)c1ccc(CNC(=O)c2cc3c(s2)C2(CCNCC2)O[C@H](C)C3)cc1 ; Cl] | 449 (M + H − HCl) |
| 68 | N-[(5-Ethylsulfonyl-2-pyridyl)methyl]-4-methyl-spiro[4,5-dihydrothieno[2,3-c]pyran-7,4'-piperidine]-2-carboxamide; hydrochloride | 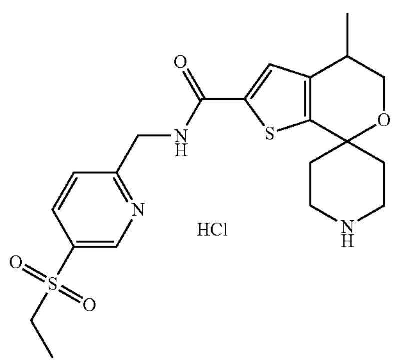 [SMILES: CCS(=O)(=O)c1ccc(CNC(=O)c2cc3c(s2)C2(CCNCC2)OCC3C)nc1 ; Cl] | 450 (M + H − HCl) |
| 69* | (4'S)-N-{[5-(ethylsulfonyl)pyridin-2-yl]methyl}-4'-methyl-4',5'-dihydrospiro[piperidine-4,7'-thieno[2,3-c]pyran]-2'-carboxamide | 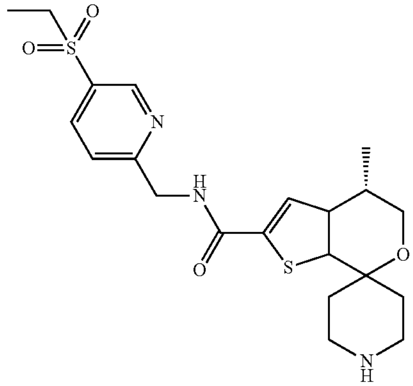 [SMILES: CCS(=O)(=O)c1ccc(CNC(=O)C2=CC3C(S2)C2(CCNCC2)OC[C@H]3C)nc1] | |

TABLE 9-continued

| Prep. No. | Chemical Name | Structure | ES/MS (m/z) (M + 1) |
|---|---|---|---|
| 70* | (5'S)-5'-Methyl-N-[4-(methylsulfonyl)benzyl]-4',5'-dihydrospiro[piperidine-4,7'-thieno[2,3-c]pyran]-2'-carboxamide | 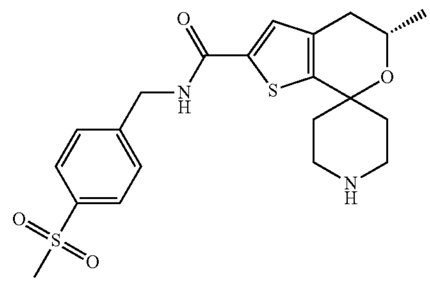 [SMILES: C[C@H]1Cc2cc(C(=O)NCc3ccc(S(C)(=O)=O)cc3)sc2C2(CCNCC2)O1] | |

*Purify the residue with ion exchange chromatography.

Preparation 71

(5S)—N-[(4-Ethylsulfonylphenyl)methyl]-1'-[1-[3-fluoro-4-[(E)-N'-hydroxycarbamimidoyl]phenyl]ethyl]-5-methyl-spiro[4,5-dihydrothieno[2,3-c]pyran-7,4'-piperidine]-2-carboxamide

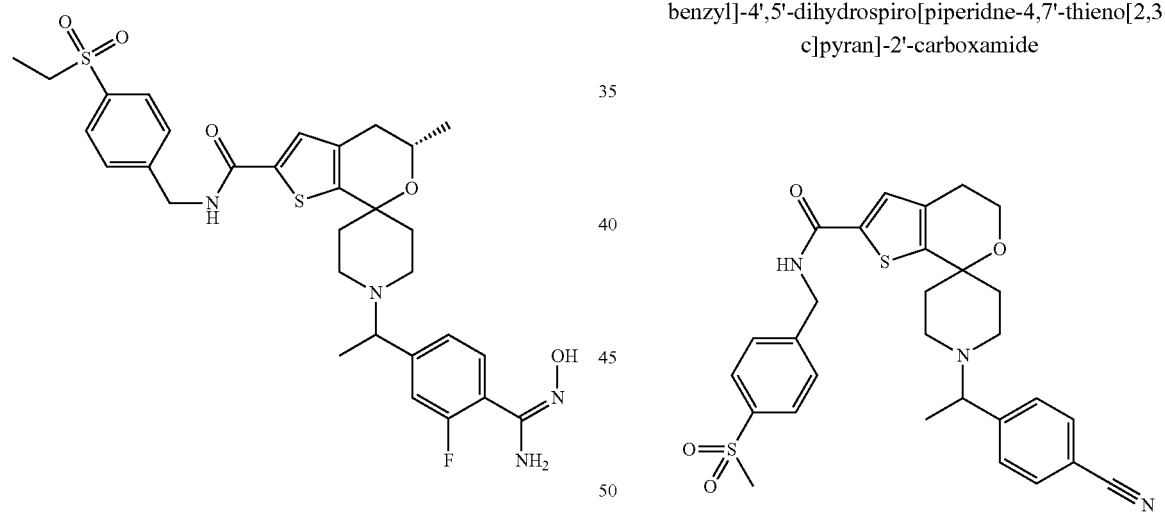

Suspend (5'S)-1-[1-(4-cyano-3-fluorophenyl)ethyl]-N-[4-(ethyl sulfonyl)benzyl]-5'-methyl-4',5'-dihydrospiro[piperidine-4,7'-thieno[2,3-c]pyran]-2'-carboxamide (0.17 g, 0.28 mmol) and hydroxylamine hydrochloride (0.029 g, 0.42 mmol) in MeOH (1.5 mL) and add DIPEA (0.079 mL, 0.45 mmol), then heat to 60° C. 15 hours. Cool to ambient temperature, add additional hydroxylamine hydrochloride (0.029 g, 0.42 mmol) and DIPEA (0.079 mL, 0.45 mmol), then resume heating at 60° C. for 3 hours. Cool to ambient temperature and concentrate under reduced pressure. Redissolve the residue in EtOAc and wash with water. Dissolve the resulting solid with MeOH, then concentrate under reduced pressure to give the title compound (0.25 g, 138%) contaminated with succinamide salts. Use the material without further purification. Mass spectrum (m/z): 629 (M+H).

Preparation 72

1-[1-(4-Cyanophenyl)ethyl]-N-[4-(methylsulfonyl)benzyl]-4',5'-dihydrospiro[piperidne-4,7'-thieno[2,3-c]pyran]-2'-carboxamide Add N-[4-(methylsulfonyl)benzyl]-4',5'-dihydrospiro[piperidine-4,7'-thieno[2,3-c]pyran]-2'-carboxamide hydrochloride (1 g, 2.19 mmol) and DIPEA (0.68 g, 4.81 mmol) together in ACN (25 mL) and add 4-(1-bromoethyl)benzonitrile (0.59 g, 2.41 mmol) and stir the mixture overnight at room temperature. Dilute the solution with EtOAc and wash with water (2×), bicarbonate (2×), brine, dry over sodium sulfate, and concentrate to dryness. Purify the residue with silica gel chromatography eluting with a 0 to 5% MeOH/DCM gradient to give the title compound (1.05 g, 100% crude).

Example 1

(5'S)—N-{[5-(Ethylsulfonyl)pyridin-2-yl]methyl}-5'-methyl-1-{[4-methyl-2-(trifluoromethyl)pyrimidin-5-yl]methyl}-4',5'-dihydrospiro[piperidine-4,7'-thieno[2,3-c]pyran]-2'-carboxamide

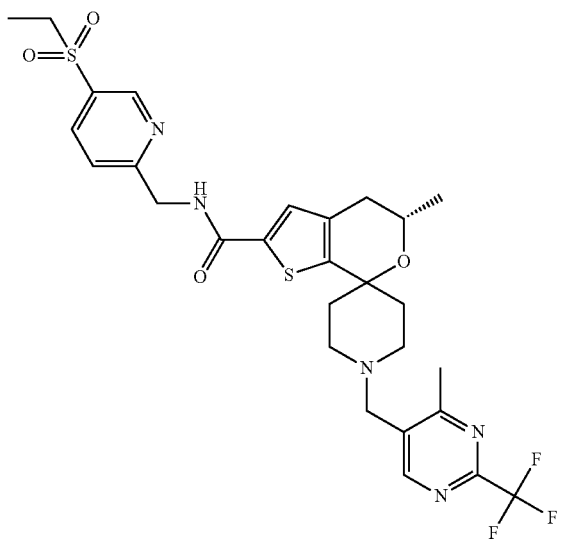 [SMILES: CCS(=O)(=O)c1ccc(CNC(=O)c2cc3c(s2)C2(CCN(Cc4cnc(C(F)(F)F)nc4C)CC2)O[C@@H](C)C3)nc1]

Example 2

(5'R)—N-{[5-(Ethylsulfonyl)pyridin-2-yl]methyl}-5'-methyl-1-{[4-methyl-2-(trifluoromethyl)pyrimidin-5-yl]methyl}-4',5'-dihydrospiro[piperidine-4,7'-thieno[2,3-c]pyran]-2'-carboxamide

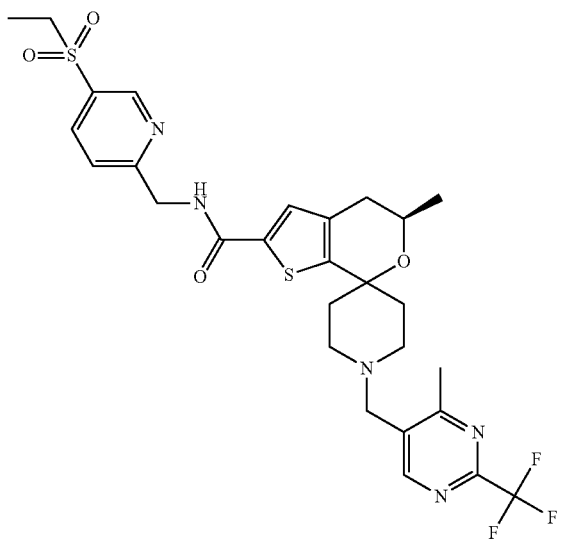 [SMILES: CCS(=O)(=O)c1ccc(CNC(=O)c2cc3c(s2)C2(CCN(Cc4cnc(C(F)(F)F)nc4C)CC2)O[C@H](C)C3)nc1]

Dissolve [4-methyl-2-(trifluoromethyl)pyrimidin-5-yl]methanol (0.53 g, 2.22 mmol) in DCM (5 mL) and add TEA (1.0 mL mL, 7.10 mmol) followed by methanesulfonyl chloride (0.2 mL, 3 mmol). Stir the mixture for 45 minutes. Dilute with DCM and wash with water, then pass the reaction mixture through a phase separator and concentrate under reduced pressure to give an intermediate of [4-methyl-2-(trifluoromethyl)pyrimidin-5-yl]methyl methanesulfonate. To a separation vessel, add ACN (20 mL) to N-{[5-(ethylsulfonyl)pyridin-2-yl]methyl}-5'-methyl-4',5'-dihydrospiro[piperidine-4,7'-thieno[2,3-c]pyran]-2'-carboxamide dihydrochloride (1.08 g, 2.23 mmol) and add DIPEA (2.0 mL, 11.5 mmol) and stir the mixture until all in solution. Add [4-methyl-2-(trifluoromethyl)pyrimidin-5-yl]methyl methanesulfonate and heat the mixture at 50° C. for 1.5 hours, then cool to room temperature, and concentrate under reduced pressure. Add DCM, wash with saturated sodium bicarbonate, then pass the mixture through phase separator. Concentrate the organic layer under reduced pressure and chromatograph on silica gel eluting with a 0% to 10% EtOH/chloroform gradient to give the racemic title compounds. Separate the racemic mixture via chiral chromatography by SFC [AD-IC column (30×250 mm, 5µ) and eluting with 50% IPA (20 mM $NH_3$) at 125 mL/min, injection of 8.5 mL (200 mg) every 16 minutes; temperature=35° C., back pressure=100 bar, UV detection at 260 nm]. Analytical conditions: SFC (220 nm UV), column: AD-IC 30×250 mm, 5µ, mobile phase: 50% IPA (20 mM $NH_3$). Dissolve the separated products in ACN (0.6 mL) then allow to crystallize at room temperature. Remove the excess solvent under a stream of $N_2$ to give the title compound of Example 1, 0.41 g, 44%, >99% ee, $R_t$=1.85 minutes, mass spectrum (m/z): 624 (M+H) and Example 2, 0.41 g, 44%, 97.9% ee, $R_t$=2.59 minutes, mass spectrum (m/z): 624 (M+H)).

Prepare the following compound essentially by the method of Example 1. The reaction temperature can range from about 50° C. to 65° C.

TABLE 10

| Ex No. | Chemical Name | Structure | ES/MS (m/z) (M + H) |
|---|---|---|---|
| 3* | (5'S)-5'-Methyl-N-[4-(methylsulfonyl)benzyl]-1-{[2-methyl-6-(trifluoromethyl)pyridin-3-yl]methyl}-4',5'-dihydrospiro[piperidine-4,7'-thieno[2,3-c]pyran]-2'-carboxamide | 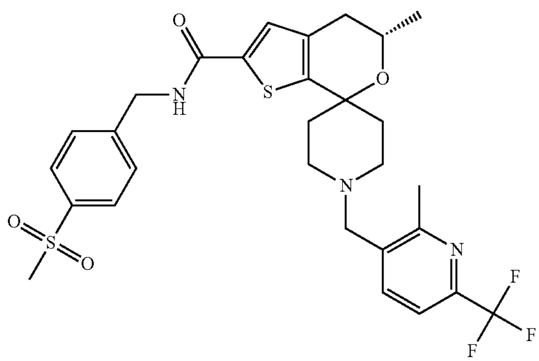 [SMILES: Cc1nc(C(F)(F)F)ccc1CN1CCC2(CC1)O[C@@H](C)Cc1cc(C(=O)NCc3ccc(S(C)(=O)=O)cc3)sc12] | 608.3 |

*Reaction stirred at room temperature overnight using chiral starting material and silica purification.

Alternate Synthesis Example 1

(5'S)—N-{[5-(Ethylsulfonyl)pyridin-2-yl]methyl}-5'-methyl-1-{[4-methyl-2-(trifluoromethyl)pyrimidin-5-yl]methyl}-4',5'-dihydrospiro[piperidine-4,7'-thieno[2,3,c]pyran]-2'-carboxamide

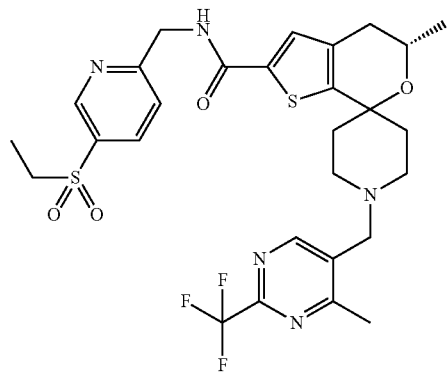 [SMILES: CCS(=O)(=O)c1ccc(CNC(=O)c2cc3c(s2)C2(CCN(Cc4cnc(C(F)(F)F)nc4C)CC2)O[C@@H](C)C3)nc1]

Dissolve (5'S)—N-{[5-(ethylsulfonyl)pyridin-2-yl]methyl}-5'-methyl-4',5',dihydrospiro[piperidine-4,7'-thieno[2,3,c]pyran]-2'-carboxamide dihydrochloride (3.0 g, 4.9 mmol) and [4-methyl-2-(trifluoromethyl)pyrimidin-5-yl]methyl methanesulfonate (1.58 g, 5.86 mmol) in anhydrous ACN (65 mL), then add DIPEA (5.1 mL, 29 mmol) and heat to 65° C. for 1.75 hours. Cool to room temperature and concentrate under reduced pressure. Add DCM, wash with water, followed by brine, then pass the mixture through a phase separator. Concentrate the organic layer under reduced pressure and chromatograph on silica gel eluting with a 0% to 5% MeOH/DCM gradient. Recrystallize the material from ACN, filter, rinse with Et₂O, and dry the resulting solid in a vacuum oven to give the title compound (1.65 g, 54%). Mass spectrum (m/z): 624 (M+H).

Prepare the following compounds essentially by the method of Alternate Example 1. The reaction temperature can vary from room temperature to about 40-70° C. and time of reaction can vary from about 1 hour to 3 days.

TABLE 11

| Ex No. | Chemical Name | Structure | ES/MS (m/z) (M + H) |
|---|---|---|---|
| 4* | 1-(4-Cyano-5-methoxy-2-methylbenzyl)-N-[4-(ethylsulfonyl)benzyl]-4',5'-dihydrospiro[piperidine-4,7'-thieno[2,3-c]pyran]-2'-carboxamide | 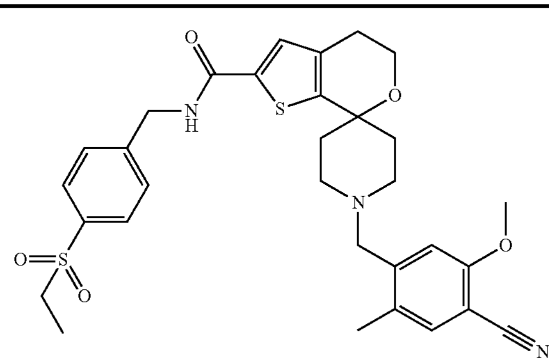 | 594.2 (M + H) |

TABLE 11-continued

| Ex No. | Chemical Name | Structure | ES/MS (m/z) (M + H) |
|---|---|---|---|
| 5* | (5'S)-N-[4-(Ethylsulfonyl)benzyl]-5'-methyl-1-{[2-methyl-6-(trifluoromethyl)pyridin-3-yl]methyl}-4',5'-dihydrospiro[piperidine-4,7'-thieno[2,3-c]pyran]-2'-carboxamide | 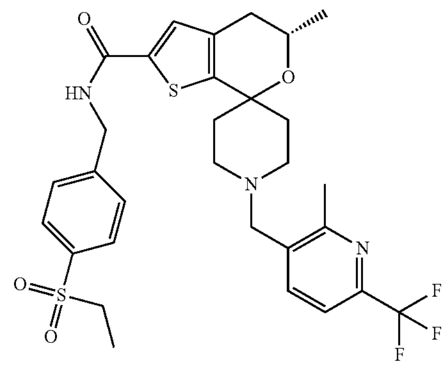 [SMILES: CCS(=O)(=O)c1ccc(CNC(=O)c2cc3c(s2)C2(CCN(Cc4ccc(C(F)(F)F)nc4C)CC2)O[C@@H](C)C3)cc1] | 622.3 (M + H) |
| 6* | (5'S)-N-[4-(Ethylsulfonyl)benzyl]-1-{1-[5-fluoro-6-(trifluoromethyl)pyridin-3-yl]ethyl}-5'-methyl-4',5'-dihydrospiro[piperidine-4,7'-thieno[2,3-c]pyran]-2'-carboxamide | 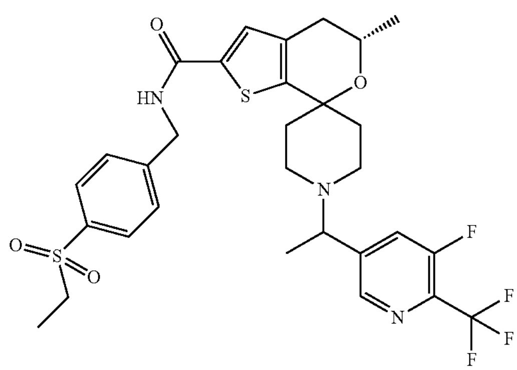 [SMILES: CCS(=O)(=O)c1ccc(CNC(=O)c2cc3c(s2)C2(CCN(C(C)c4cnc(C(F)(F)F)c(F)c4)CC2)O[C@@H](C)C3)cc1] | 640.2 (M + H) |
| 7* | (5'R)-N-[4-(Ethylsulfonyl)benzyl]-1-{1-[5-fluoro-6-(trifluoromethyl)pyridin-3-yl]ethyl}-5'-methyl-4',5'-dihydrospiro[piperidine-4,7'-thieno[2,3-c]pyran]-2'-carboxamide | 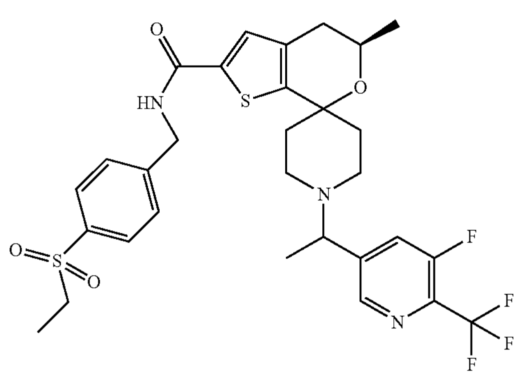 [SMILES: CCS(=O)(=O)c1ccc(CNC(=O)c2cc3c(s2)C2(CCN(C(C)c4cnc(C(F)(F)F)c(F)c4)CC2)O[C@H](C)C3)cc1] | 640.2 (M + H) |

TABLE 11-continued

| Ex No. | Chemical Name | Structure | ES/MS (m/z) (M + H) |
|---|---|---|---|
| 8 | (5'S)-N-[4-(Ethylsulfonyl)benzyl]-5'-methyl-1-[2-methyl-4-(5-methyl-1,2,4-oxadiazol-3-yl)benzyl]-4',5'-dihydrospiro[piperidine-4,7'-thieno[2,3-c]pyran]-2'-carboxamide | 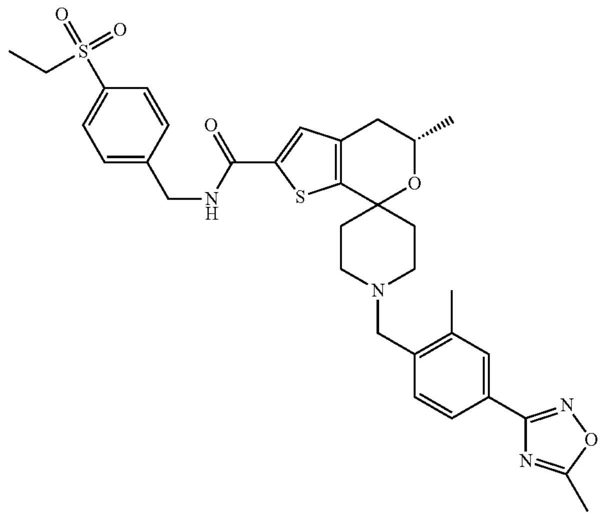 [SMILES: CCS(=O)(=O)c1ccc(CNC(=O)c2cc3c(s2)C2(CCN(Cc4ccc(-c5noc(C)n5)cc4C)CC2)O[C@@H](C)C3)cc1] | 635.2 (M + H) |
| 9* | (5'S)-N-[4-(Ethylsulfonyl)benzyl]-1-{[5-fluoro-6-(trifluoromethyl)pyridin-3-yl]methyl}-5'-methyl-4',5'-dihydrospiro[piperidine-4,7'-thieno[2,3-c]pyran]-2'-carboxamide | 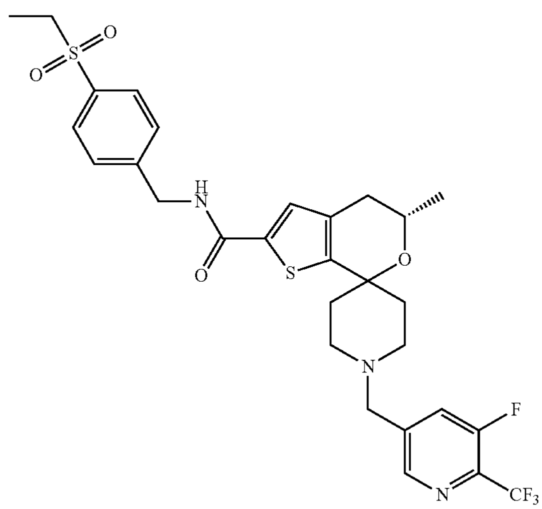 [SMILES: CCS(=O)(=O)c1ccc(CNC(=O)c2cc3c(s2)C2(CCN(Cc4cnc(C(F)(F)F)c(F)c4)CC2)O[C@@H](C)C3)cc1] | 626.2 (M + H) |
| 10* | (5'R)-N-[4-(Ethylsulfonyl)benzyl]-1-{[5-fluoro-6-(trifluoromethyl)pyridin-3-yl]methyl}-5'-methyl-4',5'-dihydrospiro[piperidine-4,7'-thieno[2,3-c]pyran]-2'-carboxamide | 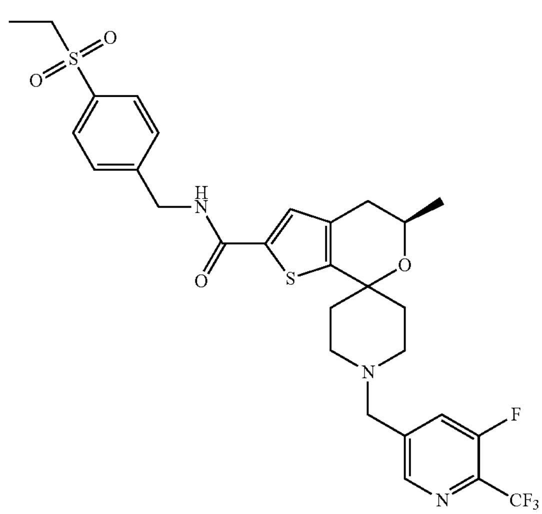 [SMILES: CCS(=O)(=O)c1ccc(CNC(=O)c2cc3c(s2)C2(CCN(Cc4cnc(C(F)(F)F)c(F)c4)CC2)O[C@H](C)C3)cc1] | 626.2 (M + H) |

TABLE 11-continued

| Ex No. | Chemical Name | Structure | ES/MS (m/z) (M + H) |
|---|---|---|---|
| 11* | (5'S)-N-[4-(Ethylsulfonyl)benzyl]-5'-methyl-1-{1-[4-methyl-2-(trifluoromethyl)pyrimidin-5-yl]ethyl}-4',5'-dihydrospiro[piperidine-4,7'-thieno[2,3-c]pyran]-2'-carboxamide isomer 1 | 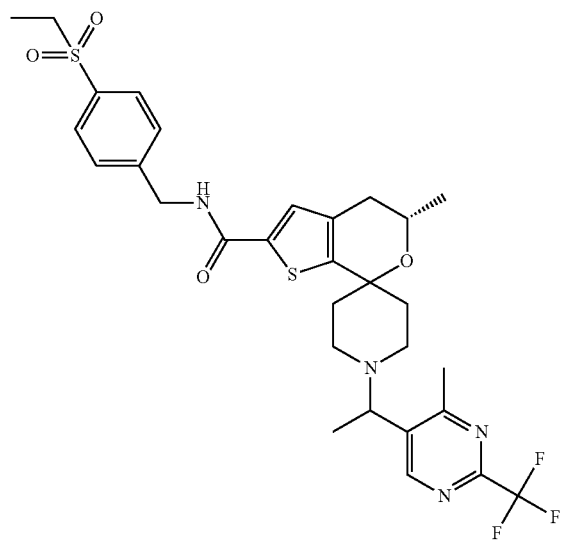 [SMILES: CCS(=O)(=O)c1ccc(CNC(=O)c2cc3c(s2)C2(CCN(C(C)c4cnc(C(F)(F)F)nc4C)CC2)O[C@@H](C)C3)cc1] | 637 (M + H) |
| 12* | (5'S)-N-{[5-(Ethylsulfonyl)pyridin-2-yl]methyl}-5'-methyl-1-{1-[4-methyl-2-(trifluoromethyl)pyrimidin-5-yl]ethyl}-4',5'-dihydrospiro[piperidine-4,7'-thieno[2,3-c]pyran]-2'-carboxamide isomer 2 | 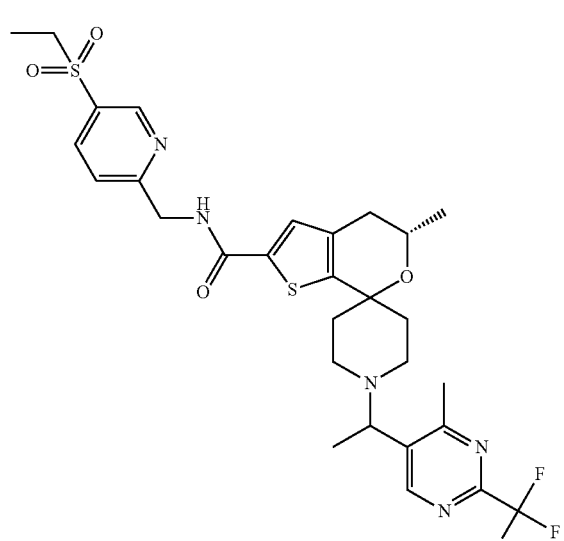 | 638 (M + H) |

*Add KI (1 equivalent) with the appropriate methanesulfonate.

Example 13

(5'R)—N-[4-(Ethylsulfonyl)benzyl]-5'-methyl-1-{(1S)-1-[2-(trifluoromethyl)pyrimidin-5-yl]ethyl}-4',5'-dihydrospiro[piperidine-4,7'-thieno[2,3-c]pyran]-2'-carboxamide

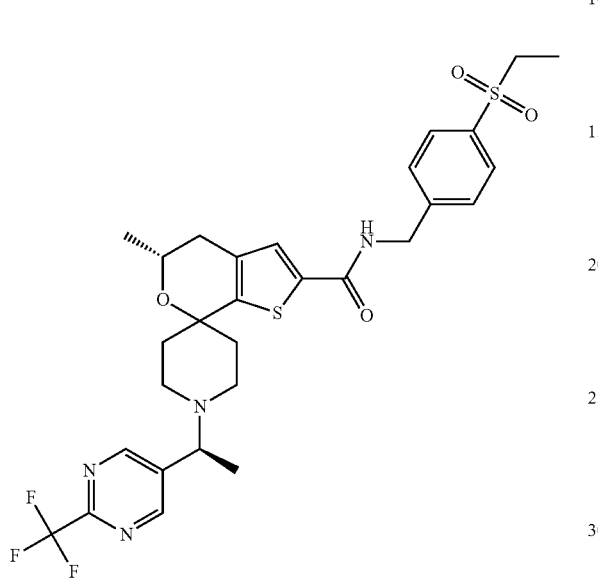

Example 14

(5'S)—N-[4-(Ethylsulfonyl)benzyl]-5'-methyl-1-{(1S)-1-[2-(trifluoromethyl)pyrimidin-5-yl]ethyl}-4',5'-dihydrospiro[piperidine-4,7'-thieno[2,3-c]pyran]-2'-carboxamide

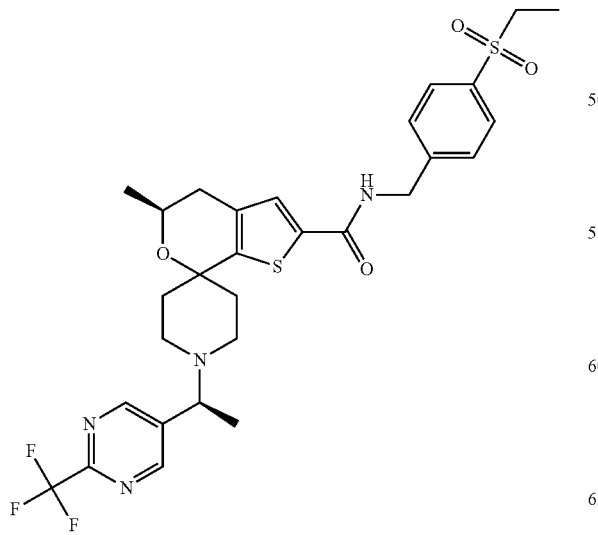

Example 15

(5'R)—N-[4-(Ethylsulfonyl)benzyl]-5'-methyl-1-{(1R)-1-[2-(trifluoromethyl)pyrimidin-5-yl]ethyl}-4',5'-dihydrospiro[piperidine-4,7'-thieno[2,3-c]pyran]-2'-carboxamide

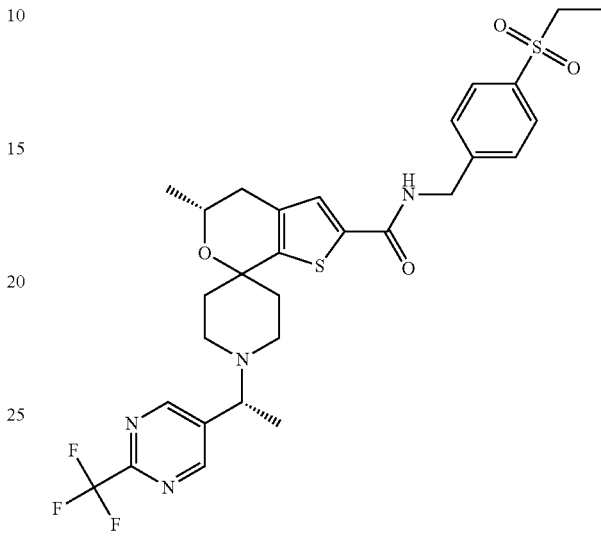

Example 16

(5'S)—N-[4-(Ethylsulfonyl)benzyl]-5'-methyl-1-{(1R)-1-[2-(trifluoromethyl)pyrimidin-5-yl]ethyl}-4',5'-dihydrospiro[piperidine-4,7'-thieno[2,3-c]pyran]-2'-carboxamide

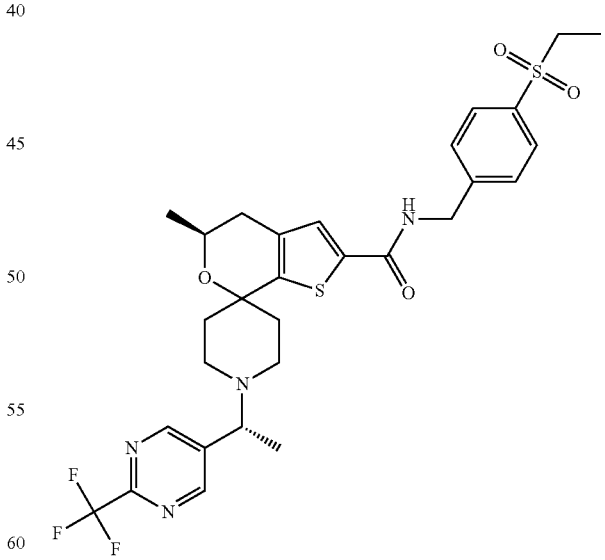

Suspend N-[4-(ethylsulfonyl)benzyl]-5'-methyl-4',5'-dihydrospiro[piperidine-4,7'-thieno[2,3-c]pyran]-2'-carboxamide hydrochloride (14.09 g, 26.44 mmol) and 5-(1-bromoethyl)-2-(trifluoromethyl)pyrimidine (8.767 g, 34.37 mmol) in ACN (5 mL/g, 55.2 g, 1340 mmol, 70.47 mL) and add DIPEA (27.7 mL, 158.6 mmol) then heat the reaction mixture for 75 minutes at 60° C. Concentrate the mixture to dryness, dilute with DCM (200 mL), wash with water (200 mL), and brine (200 mL). Dry with sodium sulfate, filter, and concentrate the residue under reduced pressure. Purify the residue by silica gel flash chromatography eluting with MeOH: DCM (0:100 to 5:95) to give the racemic mixture (11.1g). Separate the enantiomers with chiral chromatography by SFC [AD-H column (30×250 mm, 5μ´ng with 35% IPA (20 mM $NH_3$) at 280 mL/minute, injection of 8 mL (175 mg per injection) every 8 minutes, temperature=35° C., back pressure=100 bar, UV detection at 260 nm]. Freeze-dry in ACN/water (1:2) to obtain the title compounds. Analytical conditions: SFC (220 nm UV), column: AD-H 100×4.6 mm, 5μ, mobile phase: 27% IPA (1% of 2 M $NH_3$ in MeOH)/73% $CO_2$, isocratic, column temperature 35° C., flow rate=5 mL/minute, back pressure=100 bar]. The title compound of Example 13 (2.66 g, 15%, 100% ee, $R_t$=1.70 minutes), mass spectrum (m/z): 623 (M+H), the title compound of Example 14 (2.78 g, 16%, 98.64% ee, 97.3% de, $R_t$=2.10 minutes), mass spectrum (m/z): 623 (M+H) and the title compound of Example 15 (2.74 g, 16%, 98% ee, 96.5% de, $R_t$=2.60 minutes), mass spectrum (m/z): 623 (M+H). Repurify Example 16 with chiral chromatography by SFC using the same conditions to remove minor isomers and freeze-dry in ACN/water to obtain the title compound of Example 16 (2.60 g, 16%, 100% ee), $R_t$=4.02 minutes, mass spectrum (m/z): 623 (M+H).

Assign the absolute configuration of these materials via VCD. VCD-spectrometer=ChirallR-2X with DualPEM; 8.9 mg/100 μL, 4.6 mg/100 μL; resolution=$cm^{-1}$; PEM=1400 $cm^{-1}$; 72000 scans, 24 hours; $BaF_2$ cell, path length=100 μm. Force fields used in MolMec calculations=MMF94S, MMFF, SYBYL. Methodology and basis set for DFT calculations=SCRF-B3LYP/6-31G(d). Confidence level=99%.

Alternate Preparation of Example 14

(5'S)—N-[4-(Ethylsulfonyl)benzyl]-5'-methyl-1-{(1S)-1-[2-(trifluoromethyl)pyrimidin-5-yl]ethyl}-4',5'-dihydrospiro[piperidine-4,7'-thieno[2,3-c]pyran]-2'-carboxamide Alternate Preparation Example 16

(5'S)—N-[4-(Ethylsulfonyl)benzyl]-5'-methyl-1-{(1R)-1-[2-(trifluoromethyl)pyrimidin-5-yl]ethyl}-4',5'-dihydrospiro[piperidine-4,7'-thieno[2,3-c]pyran]-2'-carboxamide Suspend (5'S)—N-[4-(ethylsulfonyl)benzyl]-5'-methyl-4',5'-dihydrospiro[piperidine-4,7'-thieno[2,3-c]pyran]-2'-carboxamide hydrochloride (10.73 g, 22.11 mmol) and 5-(1-bromoethyl)-2-(trifluoromethyl)pyrimidine (6.85 g, 26.85 mmol) in ACN (100 mL) and add potassium carbonate (5.00 g, 36.17 mmol). Heat the reaction mixture to reflux for 2 hours. Cool the mix to ambient temperature, add potassium carbonate (10.00 g, 72.34 mmol), and stir for 18 hours. Add potassium carbonate (2.50 g, 18.08 mmol) and heat to reflux for 1 hour, then cool to ambient temperature. Filter the mixture and rinse with EtOAc, then concentrate the mixture under reduced pressure. Dilute the mixture with EtOAc (100 mL), wash with water (100 mL), and brine (100 mL). Dry with sodium sulfate, filter, and concentrate the residue under reduced pressure to yield the crude products (14.74 g). Separate the enantiomers with chiral chromatography by SFC [AD-H column (5×15 cm, with 27% IPA (20 mM $NH_3$) at 300 mL/minute, injection of 8 mL (175 mg per injection) every 8 minutes, temperature=35° C., back pressure=100 bar, UV detection at 280 nm]. Analytical conditions: SFC (220 nm UV), column: AD-H 100×4.6 mm, 5μ, mobile phase: 40% IPA/60% $CO_2$, isocratic. Dissolve the separated products in ACN (5 mL) then allow to crystallize at room temperature. Remove the excess solvent under a stream of N2 to give the title compound of Example 14 (5.35 g, 39%, >99% ee, >99% de, $R_t$=0.95 minutes), mass spectrum (m/z): 623 (M+H) and the title compound of Example 16 (5.49 g, 40%, >99% ee, >99% de, $R_t$=1.68 minutes), mass spectrum (m/z): 623 (M+H).

Example 17

N-[4-(Methylsulfonyl)benzyl]-1-[4-(trifluoromethyl)benzyl]-4',5'-dihydrospiro[piperidine-4,7'-thieno[2,3-c]pyran]-2'-carboxamide

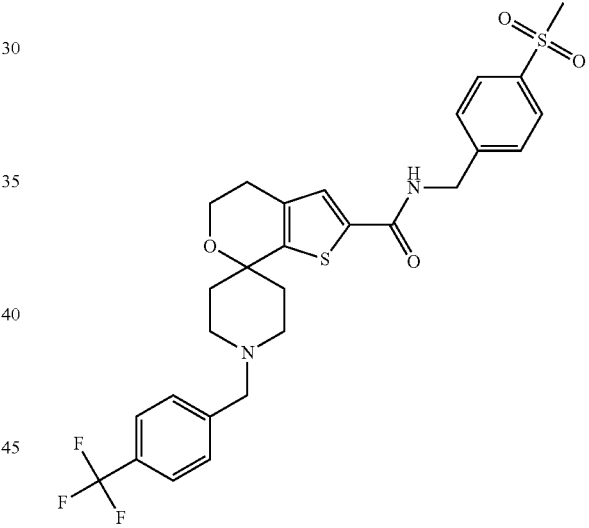

Suspend N-[4-(methylsulfonyl)benzyl]-4',5'-dihydrospiro[piperidine-4,7'-thieno[2,3-c]pyran]-2'-carboxamide hydrochloride (0.95 g, 2.08 mmol) and 4-trifluoromethylbenzyl bromide (0.55 g, 2.29 mmol) in ACN (42 mL/g, 40 mL) and add DIPEA (0.80 mL, 4.57 mmol) then stir at ambient temperature for 18 hours. Concentrate the mixture to dryness, dilute with EtOAc, wash with aqueous saturated sodium bicarbonate, and brine. Dry with sodium sulfate, filter, and concentrate the residue under reduced pressure. Purify the residue by silica gel flash chromatography eluting with a gradient of MeOH:DCM (0:100 to 5:95) and lyophilize to give the title compound (0.84 g, 70% yield) as a white solid. Mass spectrum (m/z): 579 (M+H).

Prepare the following compounds essentially by the method of Example 17 using the appropriate benzyl bromide or benzyl chloride starting material and stir at a temperature ranging from room temperature to about 75° C. and for 1-23 hours or longer if appropriate.

TABLE 12

| Ex No. | Chemical Name | Structure | ES/MS (m/z) (M + H) |
|---|---|---|---|
| 18 | N-[4-(Ethylsulfonyl)benzyl]-5'-methyl-1-{1-[6-(trifluoromethyl)pyridin-3-yl]ethyl}-4',5'-dihydrospiro[piperidine-4,7'-thieno[2,3-c]pyran]-2'-carboxamide | 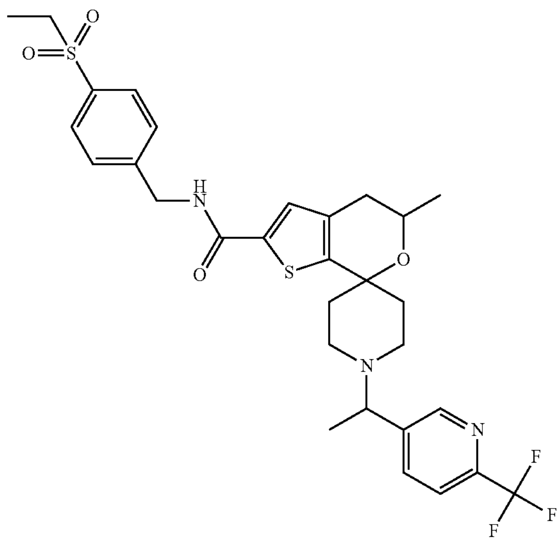 [SMILES: CCS(=O)(=O)c1ccc(CNC(=O)c2cc3c(s2)C2(CCN(C(C)c4ccc(C(F)(F)F)nc4)CC2)OC(C)C3)cc1] | 622.2 (M + H) |
| 19 | N-{[5-(Ethylsulfonyl)pyridin-2-yl]methyl}-5'-methyl-1-{1-[6-(trifluoromethyl)pyridin-3-yl]ethyl}-4',5'-dihydrospiro[piperidine-4,7'-thieno[2,3-c]pyran]-2'-carboxamide | 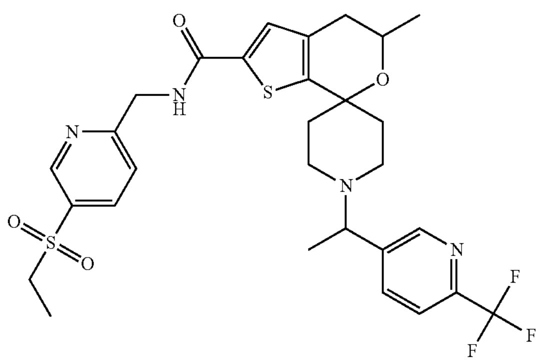 [SMILES: CCS(=O)(=O)c1ccc(CNC(=O)c2cc3c(s2)C2(CCN(C(C)c4ccc(C(F)(F)F)nc4)CC2)OC(C)C3)nc1] | 623.2 (M + H) |
| 20 | (5'S)-N-[4-(Ethylsulfonyl)benzyl]-5'-methyl-1-{1-[2-methyl-6-(trifluoromethyl)pyridin-3-yl]propyl}-4',5'-dihydrospiro[piperidine-4,7'-thieno[2,3-c]pyran]-2'-carboxamide | 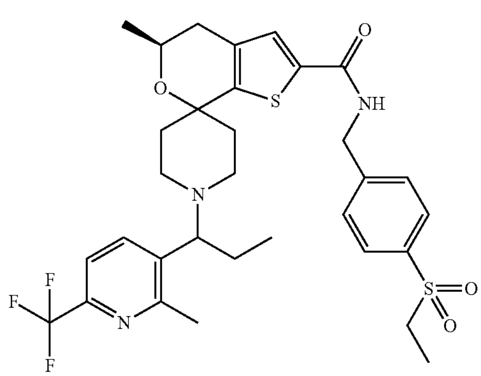 [SMILES: CCC(c1ccc(C(F)(F)F)nc1C)N1CCC2(CC1)O[C@@H](C)Cc1cc(C(=O)NCc3ccc(S(=O)(=O)CC)cc3)sc12] | 650.2 (M + H) |

TABLE 12-continued

| Ex No. | Chemical Name | Structure | ES/MS (m/z) (M + H) |
|---|---|---|---|
| 21 | (5'S)-N-[4-(Ethylsulfonyl)benzyl]-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide | 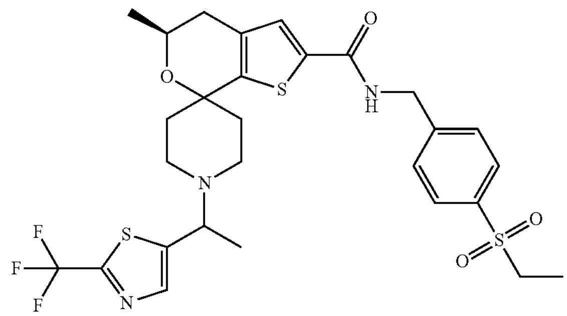 [SMILES: CCS(=O)(=O)c1ccc(CNC(=O)c2cc3c(s2)C2(CCN(C(C)c4cnc(C(F)(F)F)s4)CC2)O[C@@H](C)C3)cc1] | 628.2 (M + H) |
| 22 | (5'R)-N-[4-(Ethylsulfonyl)benzyl]-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide | 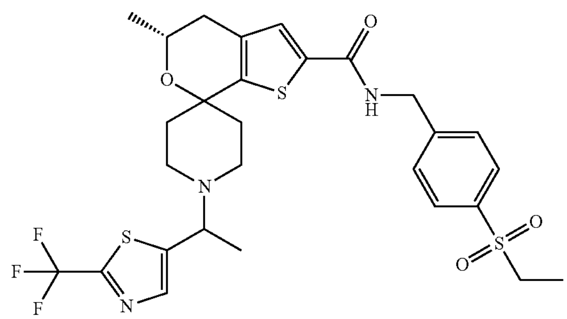 [SMILES: CCS(=O)(=O)c1ccc(CNC(=O)c2cc3c(s2)C2(CCN(C(C)c4cnc(C(F)(F)F)s4)CC2)O[C@H](C)C3)cc1] | 628.2 (M + H) |
| 23 | (5'S)-N-{[5-(Ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide | 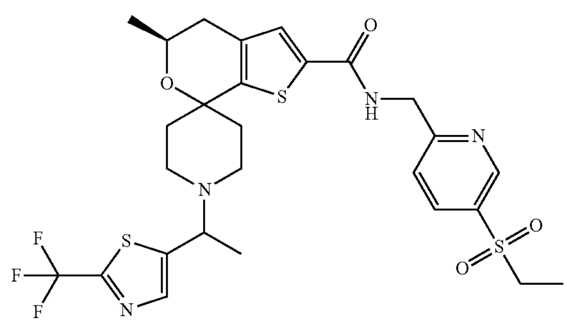 [SMILES: CCS(=O)(=O)c1ccc(CNC(=O)c2cc3c(s2)C2(CCN(C(C)c4cnc(C(F)(F)F)s4)CC2)O[C@@H](C)C3)nc1] | 629.2 (M + H) |
| 24 | (5'R)-N-{[5-(Ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide | 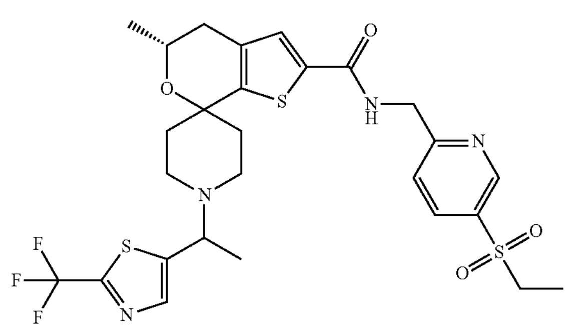 [SMILES: CCS(=O)(=O)c1ccc(CNC(=O)c2cc3c(s2)C2(CCN(C(C)c4cnc(C(F)(F)F)s4)CC2)O[C@H](C)C3)nc1] | 629.2 (M + H) |

TABLE 12-continued

| Ex No. | Chemical Name | Structure | ES/MS (m/z) (M + H) |
|---|---|---|---|
| 25 | (5'S)-N-{[5-(Ethylsulfonyl)pyridin-2-yl]methyl}-1-[2-fluoro-4-(1,2,4-oxadiazol-3-yl)benzyl]-5'-methyl-4',5'-dihydrospiro[piperidine-4,7'-thieno[2,3-c]pyran]-2'-carboxamide | 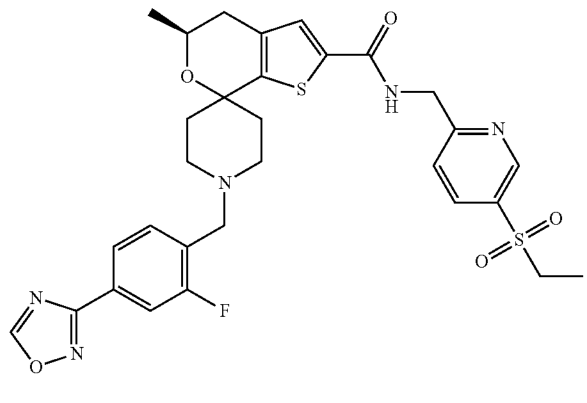 [SMILES: CCS(=O)(=O)c1ccc(CNC(=O)c2cc3c(s2)C2(CCN(Cc4ccc(-c5ncon5)cc4F)CC2)O[C@@H](C)C3)nc1] | 626.2 (M + H) |
| 26 | N-[4-(Ethylsulfonyl)benzyl]-1-{1-[2-(trifluoromethyl)pyrimidin-5-yl]ethyl}-4',5'-dihydrospiro[piperidine-4,7'-thieno[2,3-c]pyran]-2'-carboxamide | 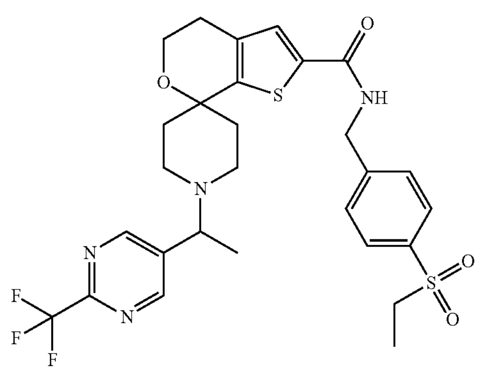 [SMILES: CCS(=O)(=O)c1ccc(CNC(=O)c2cc3c(s2)C2(CCN(C(C)c4cnc(C(F)(F)F)nc4)CC2)OCC3)cc1] | 609.2 (M + H) |
| 27 | 1-(4-Cyano-2,6-difluorobenzyl)-N-[4-(ethylsulfonyl)benzyl]-4',5'-dihydrospiro[piperidine-4,7'-thieno[2,3-c]pyran]-2'-carboxamide | 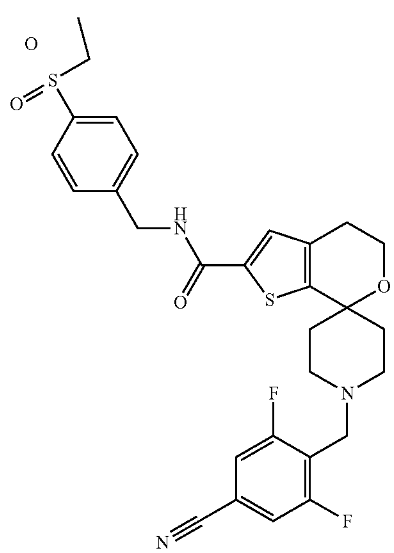 | 586.0 (M + H) |

TABLE 12-continued

| Ex No. | Chemical Name | Structure | ES/MS (m/z) (M + H) |
|---|---|---|---|
| 28 | 1-(4-Cyano-3-methoxybenzyl)-N-[4-(ethylsulfonyl)benzyl]-5'-methyl-4',5'-dihydrospiro[piperidine-4,7'-thieno[2,3-c]pyran]-2'-carboxamide | 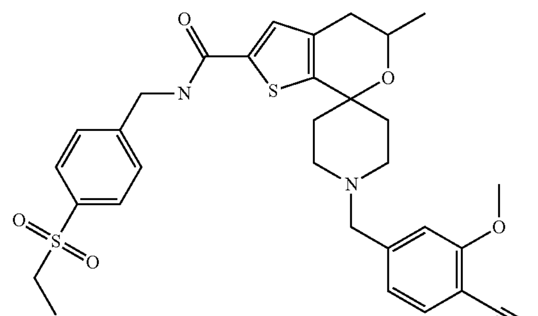 | 594.2 (M + H) |
| 29 | N-[4-(Ethylsulfonyl)benzyl]-1-[4-fluoro-3-(trifluoromethyl)benzyl]-4',5'-dihydrospiro[piperidine-4,7'-thieno[2,3-c]pyran]-2'-carboxamide | 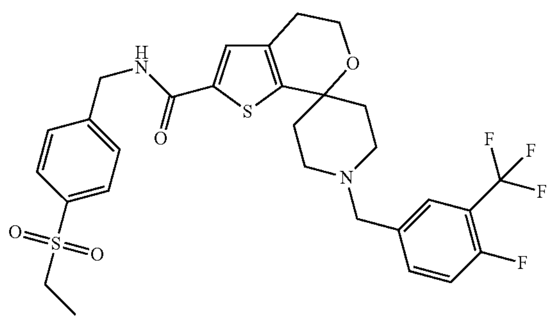 [SMILES: CCS(=O)(=O)c1ccc(CNC(=O)c2cc3c(s2)C2(CCN(Cc4ccc(F)c(C(F)(F)F)c4)CC2)OCC3)cc1] | 611.2 (M + H) |
| 30 | 1-(2,4-Dichlorobenzyl)-N-[4-(methylsulfonyl)benzyl]-4',5'-dihydrospiro[piperidine-4,7'-thieno[2,3-c]pyran]-2'-carboxamide | 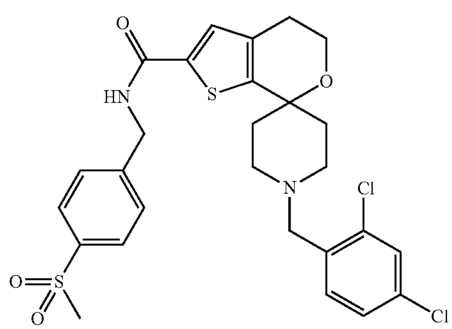 [SMILES: CS(=O)(=O)c1ccc(CNC(=O)c2cc3c(s2)C2(CCN(Cc4ccc(Cl)cc4Cl)CC2)OCC3)cc1] | 579.2, 581.2 (M + H) |
| 31 | 1-(4-Cyano-2,6-dimethylbenzyl)-N-[4-(ethylsulfonyl)benzyl]-4',5'-dihydrospiro[piperidine-4,7'-thieno[2,3-c]pyran]-2'-carboxamide | 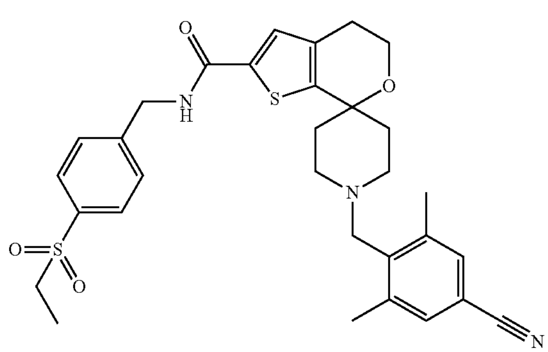 [SMILES: CCS(=O)(=O)c1ccc(CNC(=O)c2cc3c(s2)C2(CCN(Cc4c(C)cc(C#N)cc4C)CC2)OCC3)cc1] | 578.2 (M + H) |

TABLE 12-continued

| Ex No. | Chemical Name | Structure | ES/MS (m/z) (M + H) |
|---|---|---|---|
| 32 | 1-(4-Cyanobenzyl)-N-[4-(methylsulfonyl)benzyl]-4',5'-dihydrospiro[piperidine-4,7'-thieno[2,3-c]pyran]-2'-carboxamide | 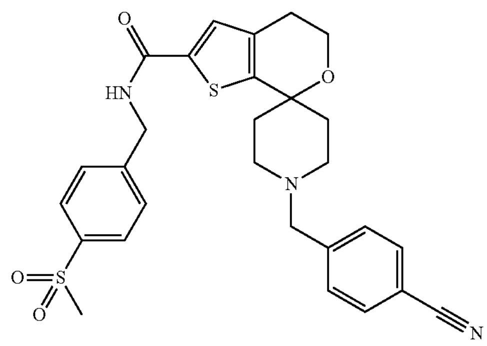 [SMILES: CS(=O)(=O)c1ccc(CNC(=O)c2cc3c(s2)C2(CCN(Cc4ccc(C#N)cc4)CC2)OCC3)cc1] | 536 (M + H) |
| 33 | 1-(4-Chlorobenzyl)-N-[4-(methylsulfonyl)benzyl]-4',5'-dihydrospiro[piperidine-4,7'-thieno[2,3-c]pyran]-2'-carboxamide | 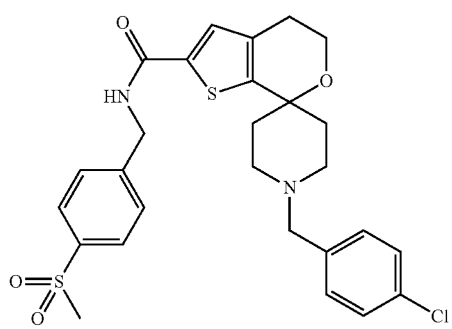 [SMILES: CS(=O)(=O)c1ccc(CNC(=O)c2cc3c(s2)C2(CCN(Cc4ccc(Cl)cc4)CC2)OCC3)cc1] | 545, 547 (M + H) |
| 34 | (5'S)-1-[1-(4-Cyano-3-fluorophenyl)ethyl]-N-[4-(ethylsulfonyl)benzyl]-5'-methyl-4',5'-dihydrospiro[piperidine-4,7'-thieno[2,3-c]pyran]-2'-carboxamide | 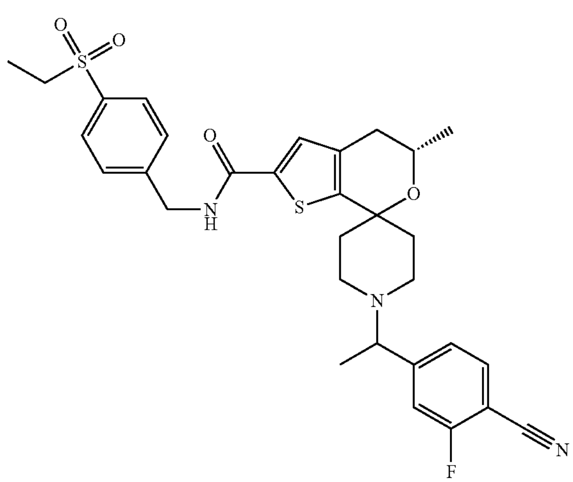 [SMILES: CCS(=O)(=O)c1ccc(CNC(=O)c2cc3c(s2)C2(CCN(C(C)c4ccc(C#N)c(F)c4)CC2)O[C@@H](C)C3)cc1] | 596.2 (M + H) |

TABLE 12-continued

| Ex No. | Chemical Name | Structure | ES/MS (m/z) (M + H) |
|---|---|---|---|
| 35 | 1-[1-(4-Cyanophenyl)ethyl]-N-{[5-(ethylsulfonyl)pyridin-2-yl]methyl}-4',5'-dihydrospiro[piperidine-4,7'-thieno[2,3-c]pyran]-2'-carboxamide | 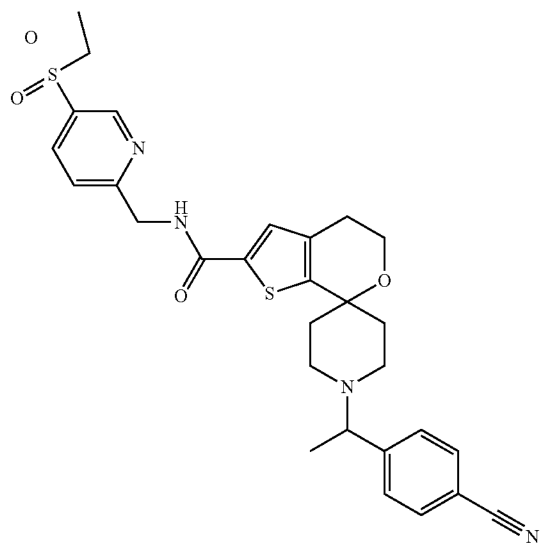 | 565.2 (M + H) |
| 36 | 1-[1-(4-Cyanophenyl)ethyl]-N-[4-(ethylsulfonyl)benzyl]-4',5'-dihydrospiro[piperidine-4,7'-thieno[2,3-c]pyran]-2'-carboxamide | 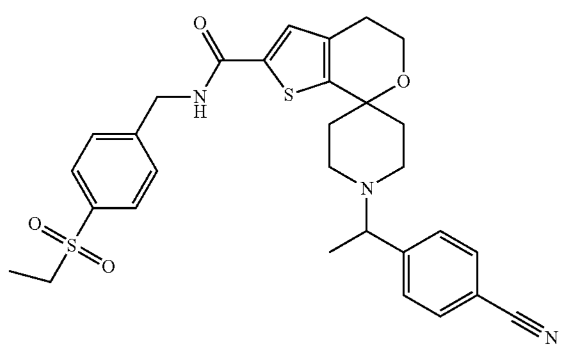 [SMILES: CCS(=O)(=O)c1ccc(CNC(=O)c2cc3c(s2)C2(CCN(C(C)c4ccc(C#N)cc4)CC2)OCC3)cc1] | 564.2 (M + H) |

Example 37

(5'R)—N-{[5-(Ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide isomer 1 and Example 38

(5'R)—N-{[5-(Ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide isomer 2

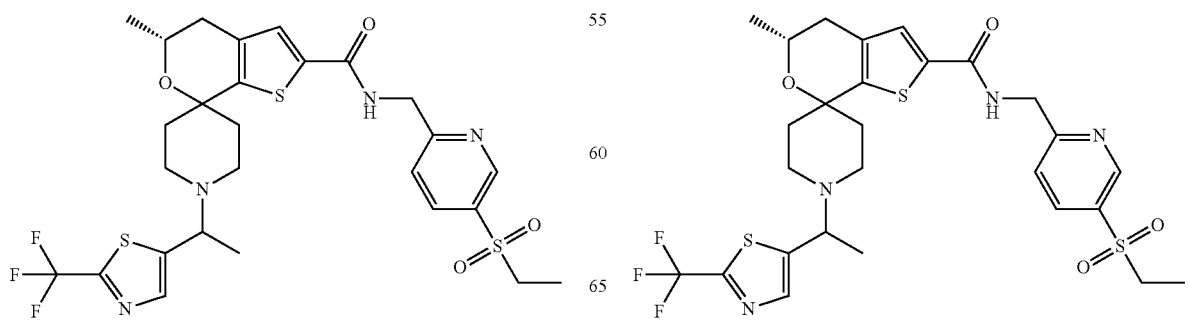

Solubilize (5'R)—N-{[5-(ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide (137 mg) in a mixture of MeOH (1.5 mL), DCM (0.2 mL) and rinse with MeOH (1 mL). Separate the isomers of (5'R)—N-{[5-(ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide with chiral chromatography by HPLC [Chiralpak IA column (30×250 mm) with 20% ACN: 80% IPA (w/0.2% IPAm) at 20 mL/min, 2.7 mL volume total, injection of 0.2 mL (appx 10.1 mg per injection), UV detection at 225 nm (monitored at 250 nm)]. Analytical conditions: 4/1 IPA(0.2% IPAm)/ACN 1.0 mL/min, Chiralpak column [IA (4.6×150 mm)] detection at 225 nm. Obtain Example 37, isomer 1 (47.78 mg, de>99%, $R_t$=3.22 minutes) and Example 38, isomer 2 (42 mg). Reprocess Example 38, isomer 2 using the same conditions to obtain Example 38, isomer 2 (26.23 mg, de 91.4%, $R_t$=4.24 minutes). Lyophilize to give the title compounds of Example 37, isomer 1 (43 mg, 30.7%). Mass spectrum (m/z): 629.2 (M+H) and Example 38, isomer 2 (23 mg, 16.4%). Mass spectrum (m/z): 629.2 (M+H) as off-white solids.

Purify the following compounds essentially by the method of Examples 37 and 38 using HPLC chiral chromatography or SFC chiral chromatography. A typical SFC system is column: Chiralpak AD-H, 20×150 mm; mobile phase: 40% EtOH (w/ 0.2% IPAm): 60% $CO_2$; flow rate: 80 mL/min; BPR set point: 100 bar; BPR temperature: 20° C.; column temperature: 40° C.; detection: 280 nm.

TABLE 13

| Ex No. | Chemical Name | Structure | ES/MS (m/z) (M + H) |
|---|---|---|---|
| 39 | (5'S)-N-[4-(Ethylsulfonyl)benzyl]-1-{1-[5-fluoro-6-(trifluoromethyl)pyridin-3-yl]ethyl}-5'-methyl-4',5'-dihydrospiro[piperidine-4,7'-thieno[2,3-c]pyran]-2'-carboxamide isomer 1 | 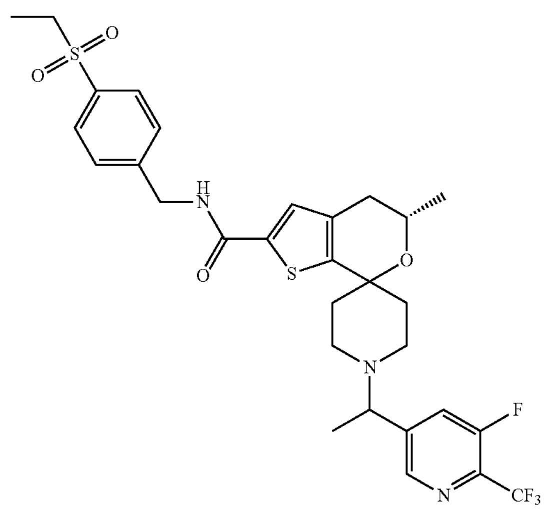 [SMILES: CCS(=O)(=O)c1ccc(CNC(=O)c2cc3c(s2)C2(CCN(C(C)c4cnc(C(F)(F)F)c(F)c4)CC2)O[C@@H](C)C3)cc1] | 640.2 (M + H) |
| 40 | (5'S)-N-[4-(Ethylsulfonyl)benzyl]-1-{1-[5-fluoro-6-(trifluoromethyl)pyridin-3-yl]ethyl}-5'-methyl-4',5'-dihydrospiro[piperidine-4,7'-thieno[2,3-c]pyran]-2'-carboxamide isomer 2 | 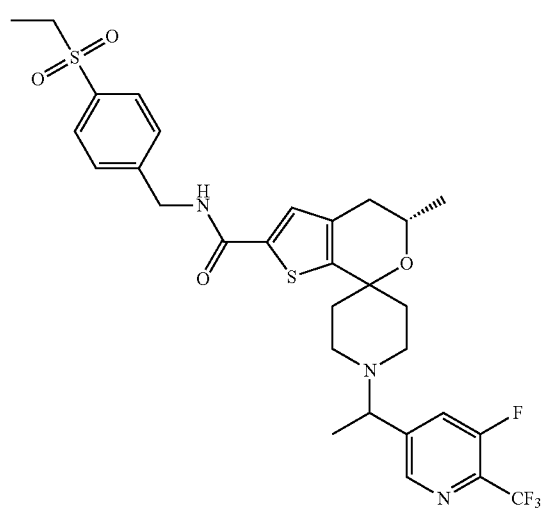 [SMILES: CCS(=O)(=O)c1ccc(CNC(=O)c2cc3c(s2)C2(CCN(C(C)c4cnc(C(F)(F)F)c(F)c4)CC2)O[C@@H](C)C3)cc1] | 640.2 (M + H) |

TABLE 13-continued

| Ex No. | Chemical Name | Structure | ES/MS (m/z) (M + H) |
|---|---|---|---|
| 41 | N-[4-(Ethylsulfonyl)benzyl]-5'-methyl-1-{1-[6-(trifluoromethyl)pyridin-3-yl]ethyl}-4',5'-dihydrospiro[piperidine-4,7'-thieno[2,3-c]pyran]-2'-carboxamide isomer 1 | 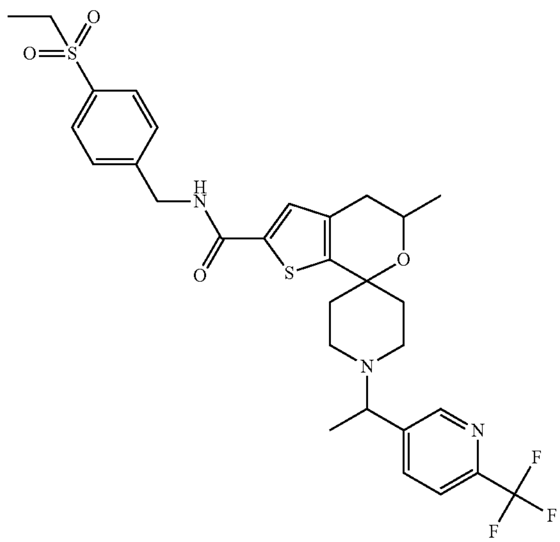 [SMILES: CCS(=O)(=O)c1ccc(CNC(=O)c2cc3c(s2)C2(CCN(C(C)c4ccc(C(F)(F)F)nc4)CC2)OC(C)C3)cc1] | 622.2 (M + H) |
| 42 | N-[4-(Ethylsulfonyl)benzyl]-5'-methyl-1-{1-[6-(trifluoromethyl)pyridin-3-yl]ethyl}-4',5'-dihydrospiro[piperidine-4,7'-thieno[2,3-c]pyran]-2'-carboxamide isomer 2 | 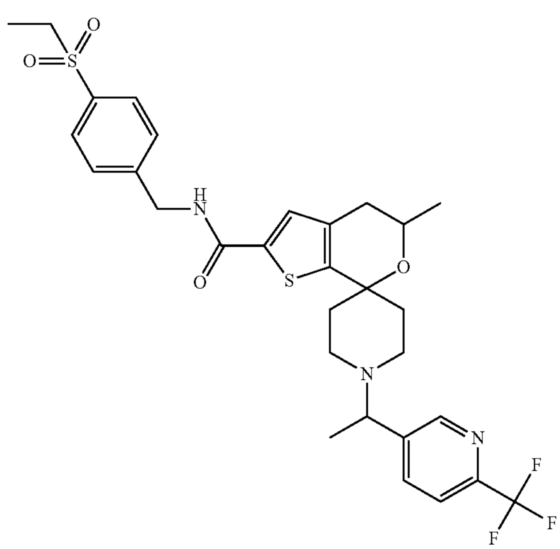 [SMILES: CCS(=O)(=O)c1ccc(CNC(=O)c2cc3c(s2)C2(CCN(C(C)c4ccc(C(F)(F)F)nc4)CC2)OC(C)C3)cc1] | 622.2 (M + H) |

TABLE 13-continued

| Ex No. | Chemical Name | Structure | ES/MS (m/z) (M + H) |
|---|---|---|---|
| 43 | N-[4-(Ethylsulfonyl)benzyl]-5'-methyl-1-{1-[6-(trifluoromethyl)pyridin-3-yl]ethyl}-4',5'-dihydrospiro[piperidine-4,7'-thieno[2,3-c]pyran]-2'-carboxamide isomer 3 | 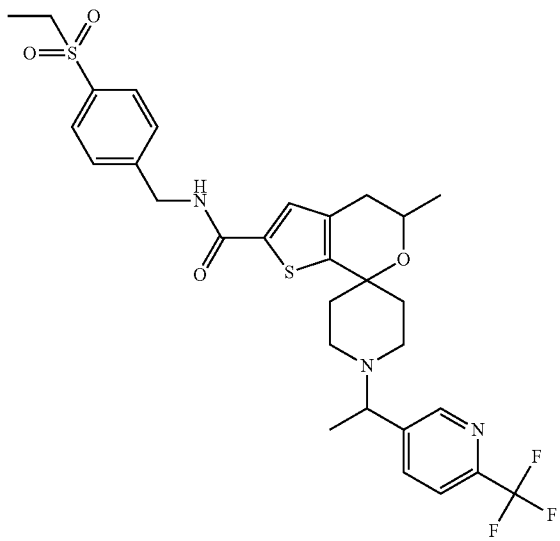 [SMILES: CCS(=O)(=O)c1ccc(CNC(=O)c2cc3c(s2)C2(CCN(C(C)c4ccc(C(F)(F)F)nc4)CC2)OC(C)C3)cc1] | 622.2 (M + H) |
| 44 | N-[4-(Ethylsulfonyl)benzyl]-5'-methyl-1-{1-[6-(trifluoromethyl)pyridin-3-yl]ethyl}-4',5'-dihydrospiro[piperidine-4,7'-thieno[2,3-c]pyran]-2'-carboxamide isomer 4 | 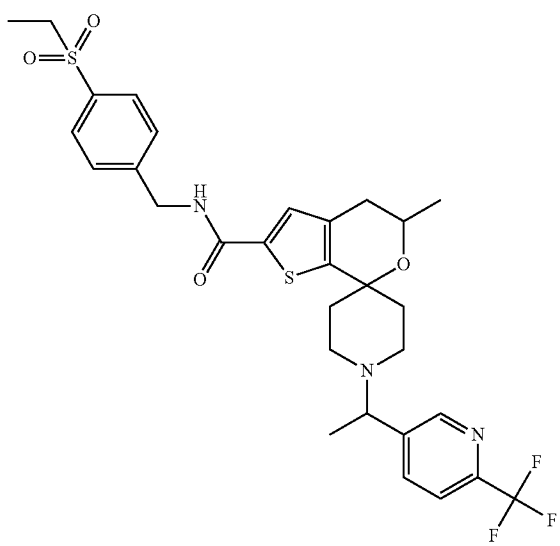 [SMILES: CCS(=O)(=O)c1ccc(CNC(=O)c2cc3c(s2)C2(CCN(C(C)c4ccc(C(F)(F)F)nc4)CC2)OC(C)C3)cc1] | 622.2 (M + H) |
| 45 | N-{[5-(Ethylsulfonyl)pyridin-2-yl]methyl}-5'-methyl-1-{1-[6-(trifluoromethyl)pyridin-3-yl]ethyl}-4',5'-dihydrospiro[piperidine-4,7'-thieno[2,3-c]pyran]-2'-carboxamide isomer 1 | 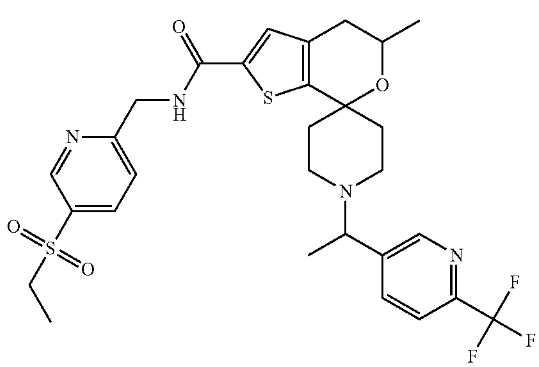 [SMILES: CCS(=O)(=O)c1ccc(CNC(=O)c2cc3c(s2)C2(CCN(C(C)c4ccc(C(F)(F)F)nc4)CC2)OC(C)C3)nc1] | 623.2 (M + H) |

TABLE 13-continued

| Ex No. | Chemical Name | Structure | ES/MS (m/z) (M + H) |
|---|---|---|---|
| 46 | N-{[5-(Ethylsulfonyl)pyridin-2-yl]methyl}-5'-methyl-1-{1-[6-(trifluoromethyl)pyridin-3-yl]ethyl}-4',5'-dihydrospiro[piperidine-4,7'-thieno[2,3-c]pyran]-2'-carboxamide isomer 2 | 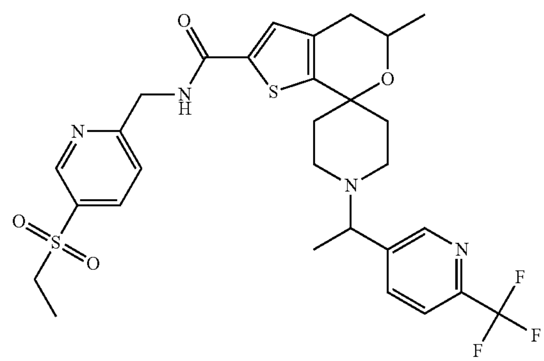 [SMILES: CCS(=O)(=O)c1ccc(CNC(=O)c2cc3c(s2)C2(CCN(C(C)c4ccc(C(F)(F)F)nc4)CC2)OC(C)C3)nc1] | 623.2 (M + H) |
| 47 | N-{[5-(Ethylsulfonyl)pyridin-2-yl]methyl}-5'-methyl-1-{1-[6-(trifluoromethyl)pyridin-3-yl]ethyl}-4',5'-dihydrospiro[piperidine-4,7'-thieno[2,3-c]pyran]-2'-carboxamide isomer 4 | 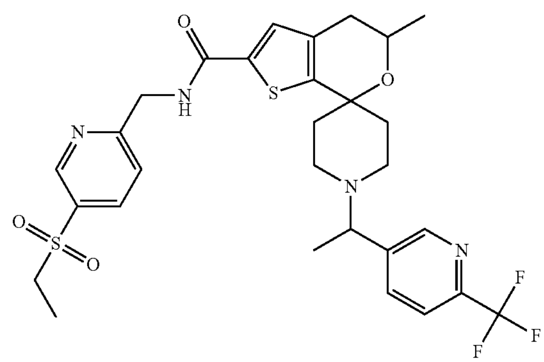 [SMILES: CCS(=O)(=O)c1ccc(CNC(=O)c2cc3c(s2)C2(CCN(C(C)c4ccc(C(F)(F)F)nc4)CC2)OC(C)C3)nc1] | 623.2 (M + H) |
| 48 | (5'S)-N-[4-(Ethylsulfonyl)benzyl]-5'-methyl-1-{1-[2-methyl-6-(trifluoromethyl)pyridin-3-yl]propyl}-4',5'-dihydrospiro[piperidine-4,7'-thieno[2,3-c]pyran]-2'-carboxamide isomer 1 | 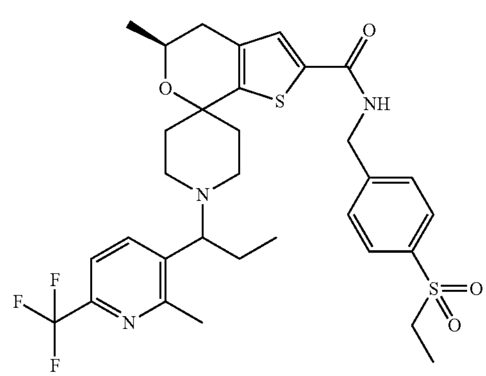 [SMILES: CCC(c1ccc(C(F)(F)F)nc1C)N1CCC2(CC1)O[C@@H](C)Cc1cc(C(=O)NCc3ccc(S(=O)(=O)CC)cc3)sc12] | 650.2 (M + H) |
| 49 | (5'S)-N-[4-(Ethylsulfonyl)benzyl]-5'-methyl-1-{1-[2-methyl-6-(trifluoromethyl)pyridin-3-yl]propyl}-4',5'-dihydrospiro[piperidine-4,7'-thieno[2,3-c]pyran]-2'-carboxamide isomer 2 | 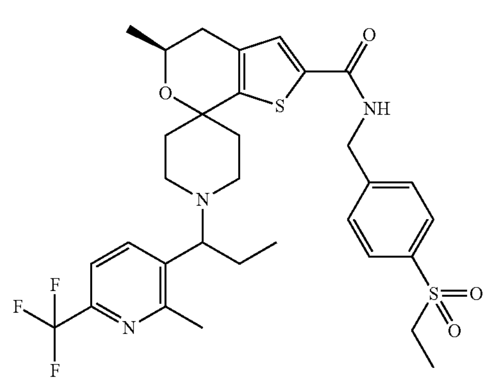 [SMILES: CCC(c1ccc(C(F)(F)F)nc1C)N1CCC2(CC1)O[C@@H](C)Cc1cc(C(=O)NCc3ccc(S(=O)(=O)CC)cc3)sc12] | 650.2 (M + H) |

TABLE 13-continued

| Ex No. | Chemical Name | Structure | ES/MS (m/z) (M + H) |
|---|---|---|---|
| 50 | (5'S)-N-[4-(Ethylsulfonyl)benzyl]-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide isomer 1 | 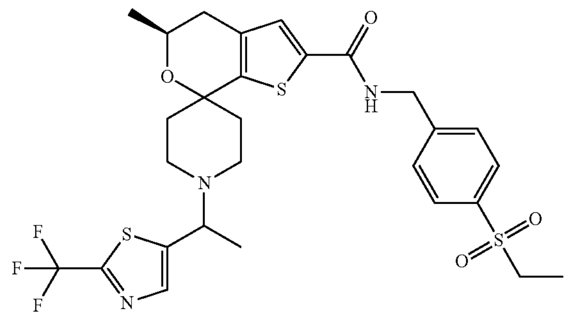 [SMILES: CCS(=O)(=O)c1ccc(CNC(=O)c2cc3c(s2)C2(CCN(C(C)c4cnc(C(F)(F)F)s4)CC2)O[C@@H](C)C3)cc1] | 628.2 (M + H) |
| 51 | (5'S)-N-[4-(Ethylsulfonyl)benzyl]-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide isomer 2 | 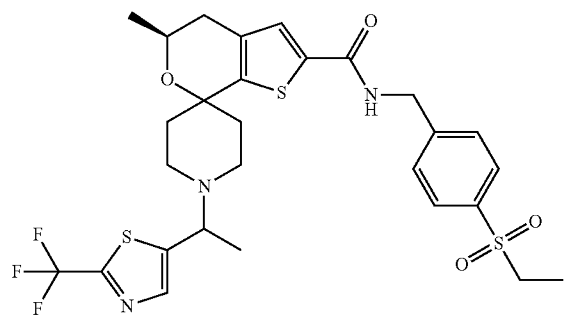 [SMILES: CCS(=O)(=O)c1ccc(CNC(=O)c2cc3c(s2)C2(CCN(C(C)c4cnc(C(F)(F)F)s4)CC2)O[C@@H](C)C3)cc1] | 628.2 (M + H) |
| 52 | (5'R)-N-[4-(Ethylsulfonyl)benzyl]-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide isomer 1 | 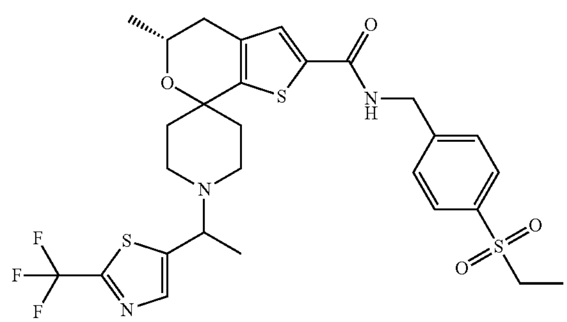 [SMILES: CCS(=O)(=O)c1ccc(CNC(=O)c2cc3c(s2)C2(CCN(C(C)c4cnc(C(F)(F)F)s4)CC2)O[C@H](C)C3)cc1] | 628.2 (M + H) |
| 53 | (5'R)-N-[4-(Ethylsulfonyl)benzyl]-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide isomer 2 | 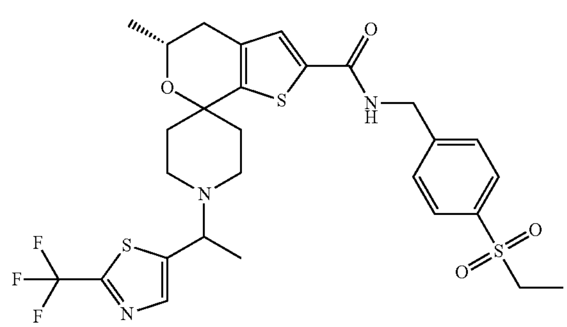 [SMILES: CCS(=O)(=O)c1ccc(CNC(=O)c2cc3c(s2)C2(CCN(C(C)c4cnc(C(F)(F)F)s4)CC2)O[C@H](C)C3)cc1] | 628.2 (M + H) |

TABLE 13-continued

| Ex No. | Chemical Name | Structure | ES/MS (m/z) (M + H) |
|---|---|---|---|
| 54 | (5'S)-N-{[5-(Ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide isomer 1 | 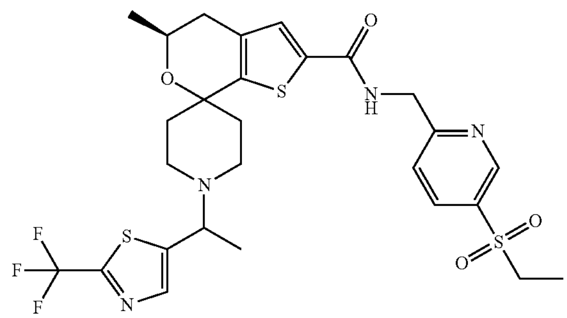 [SMILES: CCS(=O)(=O)c1ccc(CNC(=O)c2cc3c(s2)C2(CCN(C(C)c4cnc(C(F)(F)F)s4)CC2)O[C@@H](C)C3)nc1] | 629.2 (M + H) |
| 55 | (5'S)-N-{[5-(Ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide isomer 2 | 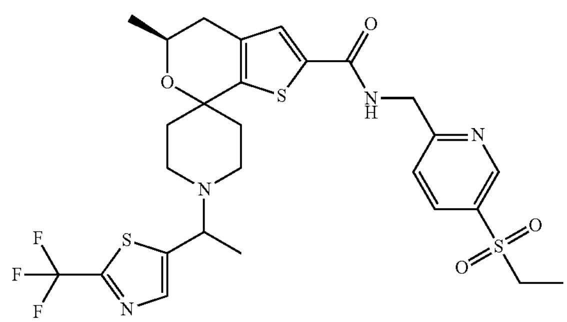 [SMILES: CCS(=O)(=O)c1ccc(CNC(=O)c2cc3c(s2)C2(CCN(C(C)c4cnc(C(F)(F)F)s4)CC2)O[C@@H](C)C3)nc1] | 629.2 (M + H) |
| 56 | N-[4-(Ethylsulfonyl)benzyl]-1-{1-[2-(trifluoromethyl)pyrimidin-5-yl]ethyl}-4',5'-dihydrospiro[piperidine-4,7'-thieno[2,3-c]pyran]-2'-carboxamide isomer 1 | 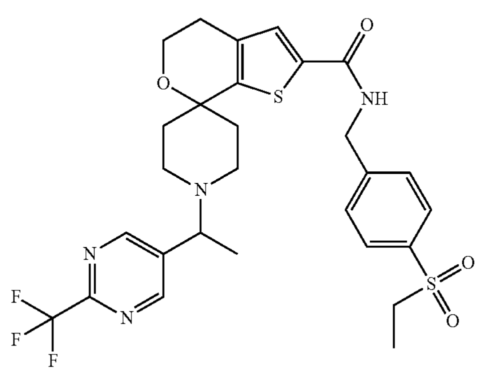 [SMILES: CCS(=O)(=O)c1ccc(CNC(=O)c2cc3c(s2)C2(CCN(C(C)c4cnc(C(F)(F)F)nc4)CC2)OCC3)cc1] | 609.2 (M + H) |
| 57 | N-[4-(Ethylsulfonyl)benzyl]-1-{1-[2-(trifluoromethyl)pyrimidin-5-yl]ethyl}-4',5'-dihydrospiro[piperidine-4,7'-thieno[2,3-c]pyran]-2'-carboxamide isomer 2 | 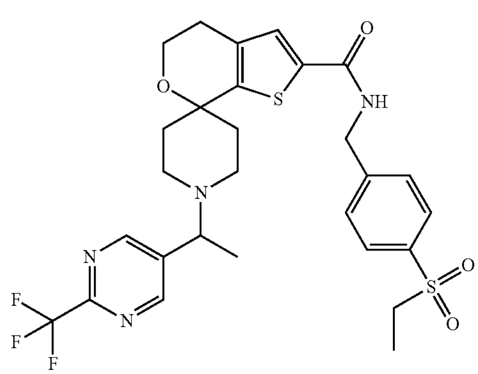 [SMILES: CCS(=O)(=O)c1ccc(CNC(=O)c2cc3c(s2)C2(CCN(C(C)c4cnc(C(F)(F)F)nc4)CC2)OCC3)cc1] | 609.2 (M + H) |

TABLE 13-continued

| Ex No. | Chemical Name | Structure | ES/MS (m/z) (M + H) |
|---|---|---|---|
| 58 | 1-(4-Cyano-3-methoxybenzyl)-N-[4-(ethylsulfonyl)benzyl]-5'-methyl-4',5'-dihydrospiro[piperidine-4,7'-thieno[2,3-c]pyran]-2'-carboxamide isomer 1 | 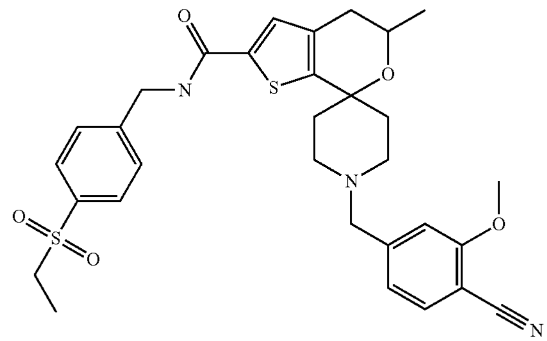 [SMILES: CCS(=O)(=O)c1ccc(CNC(=O)c2cc3c(s2)C2(CCN(Cc4ccc(C#N)c(OC)c4)CC2)OC(C)C3)cc1] | 594.2 (M + H) |
| 59 | 1-(4-Cyano-3-methoxybenzyl)-N-[4-(ethyslulfonyl)benzyl]-5'-methyl-4',5'-dihydrospiro[piperidine-4,7'-thieno[2,3-c]pyran]-2'-carboxamide isomer 2 | 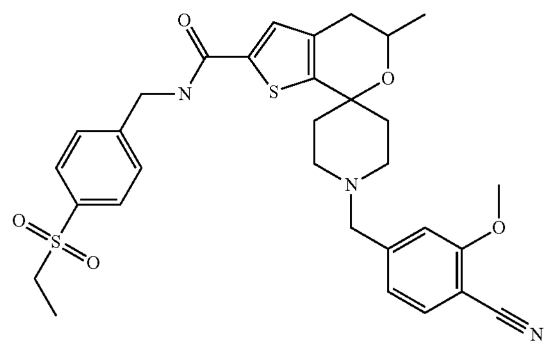 [SMILES: CCS(=O)(=O)c1ccc(CNC(=O)c2cc3c(s2)C2(CCN(Cc4ccc(C#N)c(OC)c4)CC2)OC(C)C3)cc1] | 594.2 (M + H) |
| 60 | (5'S)-N-{[5-(Ethylsulfonyl)pyridin-2-yl]methyl}-5'-methyl-1-{1-[2-methyl-6-(trifluoromethyl)pyridin-3-yl]propyl}-4',5'-dihydrospiro[piperidine-4,7'-thieno[2,3-c]pyran]-2'-carboxamide isomer 1 | 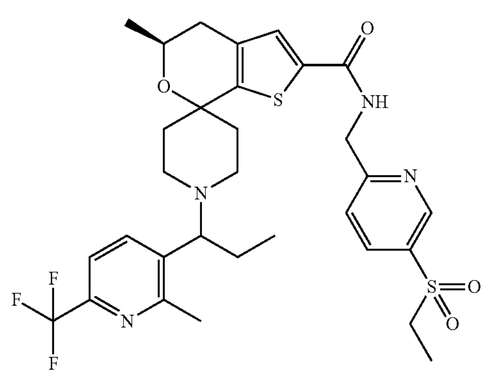 [SMILES: CCC(c1ccc(C(F)(F)F)nc1C)N1CCC2(CC1)O[C@@H](C)Cc1cc(C(=O)NCc3ccc(S(=O)(=O)CC)cn3)sc12] | 651.2 (M + H) |
| 61 | N-[4-(Ethylsulfonyl)benzyl]-1-{1-[4-(trifluoromethyl)phenyl]ethyl}-4',5'-dihydrospiro[piperidine-4,7'-thieno[2,3-c]pyran]-2'-carboxamide isomer 1 | 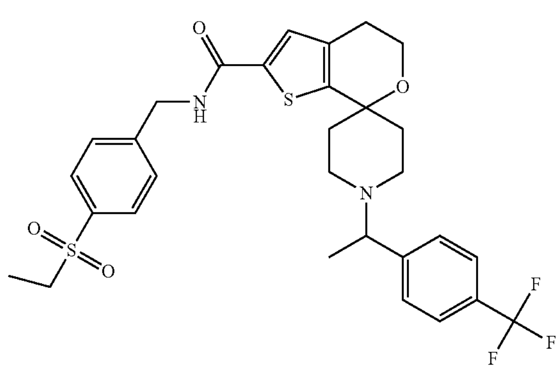 [SMILES: CCS(=O)(=O)c1ccc(CNC(=O)c2cc3c(s2)C2(CCN(C(C)c4ccc(C(F)(F)F)cc4)CC2)OCC3)cc1] | 607.2 (M + H) |

TABLE 13-continued

| Ex No. | Chemical Name | Structure | ES/MS (m/z) (M + H) |
|---|---|---|---|
| 62 | 1-[1-(4-Cyanophenyl)ethyl]-N-{[5-(ethyslulfonyl)pyridin-2-yl]methyl}-4',5'-dihydrospiro[piperidine-4,7'-thieno[2,3-c]pyran]-2'-carboxamide isomer 2 | 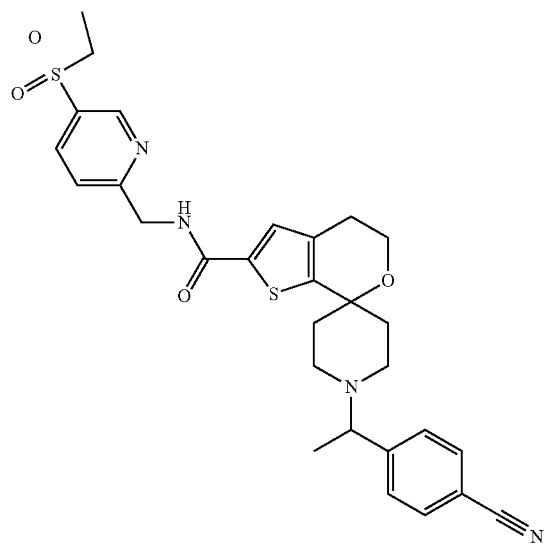 | 565.2 (M + H) |
| 63 | 1-[(1S)-1-(4-Cyanophenyl)ethyl]-N-[4-(methylsulfonyl)benzyl]-4',5'-dihydrospiro[piperidine-4,7'-thieno[2,3-c]pyran]-2'-carboxamide | 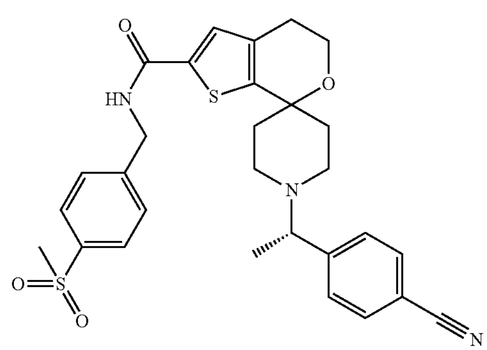 [SMILES: C[C@@H](c1ccc(C#N)cc1)N1CCC2(CC1)OCCc1cc(C(=O)NCc3ccc(S(C)(=O)=O)cc3)sc12] | 550.2 (M + H) |
| 64 | 1-[(1S)-1-(4-Cyanophenyl)ethyl]-N-[4-(ethylsulfonyl)benzyl]-4',5'-dihydrospiro[piperidine-4,7'-thieno[2,3-c]pyran]-2'-carboxamide | 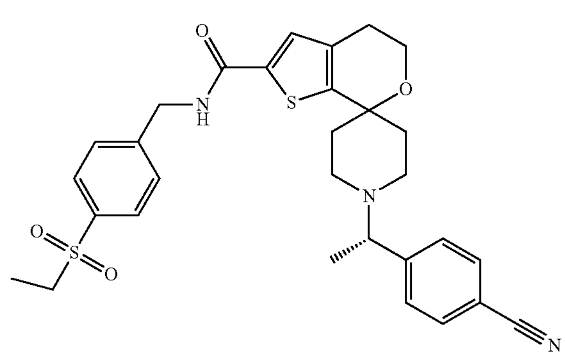 | 564.2 (M + H) |

TABLE 13-continued

| Ex No. | Chemical Name | Structure | ES/MS (m/z) (M + H) |
|---|---|---|---|
| 65 | 1-[(1R)-1-(4-Cyanophenyl)ethyl]-N-[4-(ethylsulfonyl)benzyl]-4',5'-dihydrospiro[piperidine-4,7'-thieno[2,3-c]pyran]-2'-carboxamide | 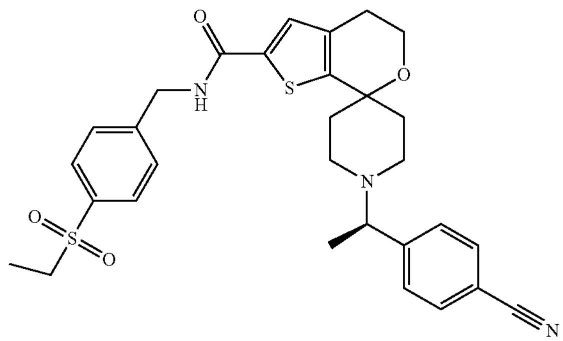 [SMILES: CCS(=O)(=O)c1ccc(CNC(=O)c2cc3c(s2)C2(CCN([C@H](C)c4ccc(C#N)cc4)CC2)OCC3)cc1] | 564.2 (M + H) |
| 66 | (5'S)-N-[4-(Ethylsulfonyl)benzyl]-5'-methyl-1-{1-[4-methyl-2-(trifluoromethyl)pyrimidin-5-yl]ethyl}-4',5'-dihydrospiro[piperidine-4,7'-thieno[2,3-c]pyran]-2'-carboxamide isomer 1 | 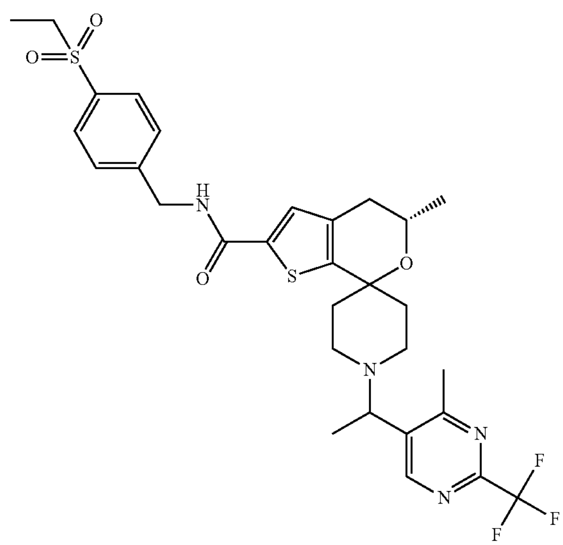 [SMILES: CCS(=O)(=O)c1ccc(CNC(=O)c2cc3c(s2)C2(CCN(C(C)c4cnc(C(F)(F)F)nc4C)CC2)O[C@@H](C)C3)cc1] | 637 (M + H) |
| 67 | (5'S)-N-[4-(Ethylsulfonyl)benzyl]-5'-methyl-1-{1-[4-methyl-2-(trifluoromethyl)pyrimidin-5-yl]ethyl}-4',5'-dihydrospiro[piperidine-4,7'-thieno[2,3-c]pyran]-2'-carboxamide isomer 2 | 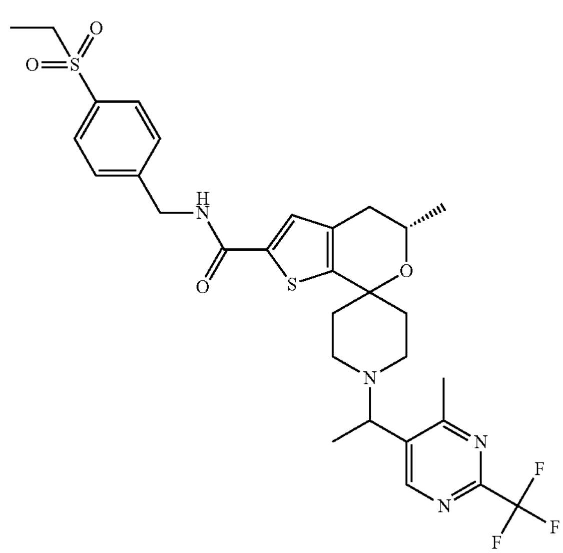 [SMILES: CCS(=O)(=O)c1ccc(CNC(=O)c2cc3c(s2)C2(CCN(C(C)c4cnc(C(F)(F)F)nc4C)CC2)O[C@@H](C)C3)cc1] | 637 (M + H) |

TABLE 13-continued

| Ex No. | Chemical Name | Structure | ES/MS (m/z) (M + H) |
|---|---|---|---|
| 68 | (5'S)-N-{[5-(Ethylsulfonyl)pyridin-2-yl]methyl}-5'-methyl-1-{1-[4-methyl-2-(trifluoromethyl)pyrimidin-5-yl]methyl}-4',5'-dihydrospiro[piperidine-4,7'-thieno[2,3-c]pyran]-2'-carboxamide isomer 1 | 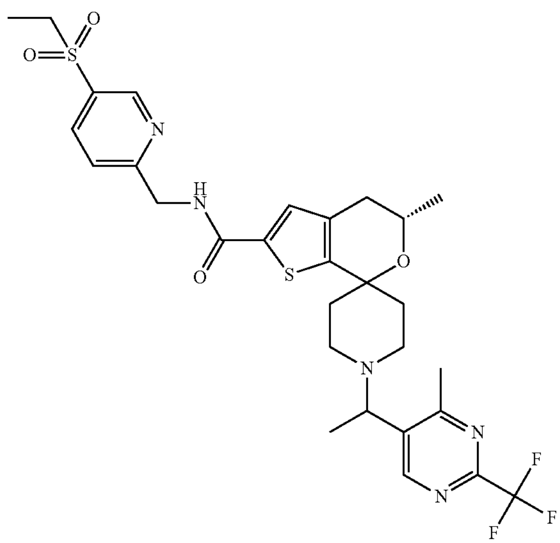 [SMILES: CCS(=O)(=O)c1ccc(CNC(=O)c2cc3c(s2)C2(CCN(C(C)c4cnc(C(F)(F)F)nc4C)CC2)O[C@@H](C)C3)nc1] | 638 (M + H) |
| 69 | (5'S)-N-{[5-(Ethylsulfonyl)pyridin-2-yl]methyl}-5'-methyl-1-{1-[4-methyl-2-(trifluoromethyl)pyrimidin-5-yl]ethyl}-4',5'-dihydrospiro[piperidine-4,7'-thieno[2,3-c]pyran]-2'-carboxamide isomer 2 | 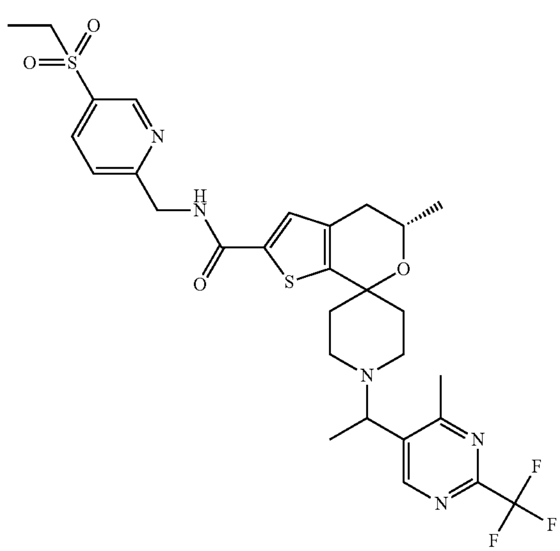 [SMILES: CCS(=O)(=O)c1ccc(CNC(=O)c2cc3c(s2)C2(CCN(C(C)c4cnc(C(F)(F)F)nc4C)CC2)O[C@@H](C)C3)nc1] | 638 (M + H) |

Example 70

1-(2,4-Dichlorobenzyl)-N-[4-(ethylsulfonyl)benzyl]-4',5'-dihydrospiro[piperidine-4,7'-thieno[2,3-c]pyran]-2'-carboxamide

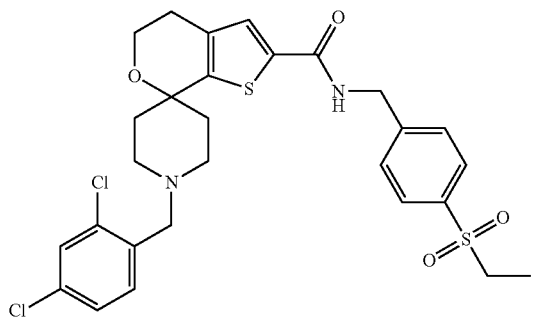 [SMILES: CCS(=O)(=O)c1ccc(CNC(=O)c2cc3c(s2)C2(CCN(Cc4ccc(Cl)cc4Cl)CC2)OCC3)cc1]

Combine 1'-[(2,4-dichlorophenyl)methyl]spiro[4,5-dihydrothieno[2,3-c]pyran-7,4'-piperidine]-2-carboxylic acid (600 mg, 1.455 mmol), (4-ethylsulfonylphenyl)methanamine hydrochloride (0.377 g, 1.60 mmol), HBTU (686 mg, 1.75 mmol), TEA (1 mL, 7.17 mmol) and DCM (15 mL) and stir for 4 hours. Quench the reaction with water and extract with EtOAc (3×). Combine the organic extracts, dry over magnesium sulfate, filter, and concentrate under reduced pressure to give a colorless residue. Add acetonitrile to the residue and sonicate. Filter the residue and dry in a vacuum oven at 50° C. overnight to give the title compound (627 mg, 72.6%). Mass spectrum (m/z): 593.2/595.2 (M+H).

Example 71

1-(3-Bromo-2,4-difluorobenzyl)-N-[4-(methylsulfonyl)benzyl]-4',5'-dihydrospiro[piperidine-4,7'-thieno[2,3-c]pyran]-2'-carboxamide

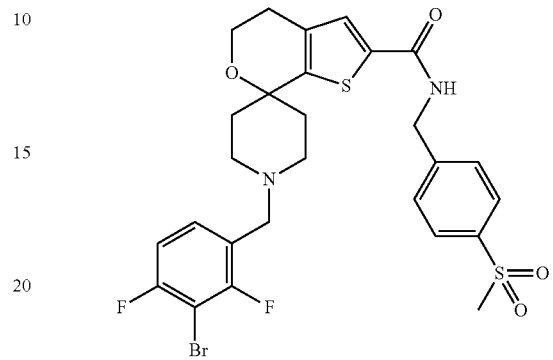

Dissolve N-[4-(methylsulfonyl)benzyl]-4',5'-dihydrospiro[piperidine-4,7'-thieno[2,3-c]pyran]-2'-carboxamide hydrochloride (0.30 g, 0.66 mmol) and 3-bromo-2,4-difluoro-benzaldehyde (0.43 g, 1.97 mmol) in DCM (0.05M, 13 mL) and add DIPEA (0.34 mL, 1.97 mmol) followed by sodium triacetoxyborohydride (0.69 g, 3.28 mmol) then seal the vessel and heat at 40° C. for 18 hours. Cool to ambient temperature and add water. Extract the aqueous layer with DCM (3×) and combine the organic extracts. Concentrate the material under reduced pressure and purify the residue by rotary silica gel chromatography eluting with 2 M ammonia in MeOH:DCM (3:97-5:95) to give the title compound (0.368 g, 90%) as a white foam. Mass spectrum (m/z): 627 (M+H).

Prepare the following compounds essentially by the method of Example 71. The reaction time can vary from about 3 hours to overnight.

TABLE 14

| Ex No. | Chemical Name | Structure | ES/MS (m/z) (M + H) |
|---|---|---|---|
| 72 | (5'S)-N-{[5-(Ethylsulfonyl)pyridin-2-yl]methyl}-5'-methyl-1-{[5-(trifluoromethyl)-1,3-thiazol-2-yl]methyl}-4',5'-dihydrospiro[piperidine-4,7'-thieno[2,3-c]pyran]-2'-carboxamide | 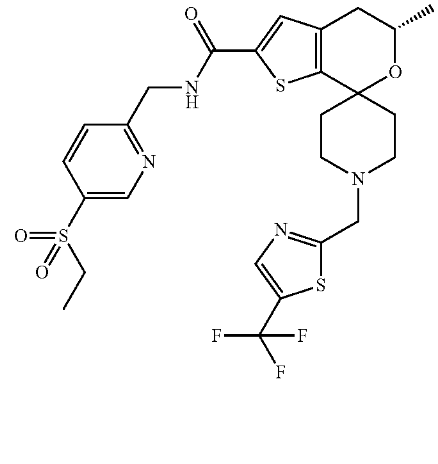 [SMILES: CCS(=O)(=O)c1ccc(CNC(=O)c2cc3c(s2)C2(CCN(Cc4ncc(C(F)(F)F)s4)CC2)O[C@@H](C)C3)nc1] | 615.1 (M + H) |

TABLE 14-continued

| Ex No. | Chemical Name | Structure | ES/MS (m/z) (M + H) |
|---|---|---|---|
| 73 | (5'S)-N-[4-(Ethylsulfonyl)benzyl]-5'-methyl-1-{[5-(trifluoromethyl)-1,3-thiazol-2-yl]methyl}-4',5'-dihydrospiro[piperidine-4,7'-thieno[2,3-c]pyran]-2'-carboxamide | 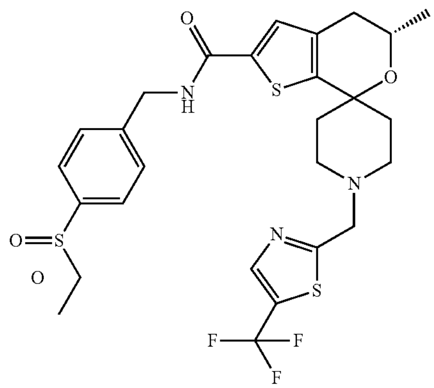 | 614.0 (M + H) |
| 74 | (5'S)-N-{[5-(Ethylsulfonyl)pyridin-2-yl]methyl}-5'-methyl-1-{[2-(trifluoromethyl)-1,3-thiazol-5-yl]methyl}-4',5'-dihydrospiro[piperidine-4,7'-thieno[2,3-c]pyran]-2'-carboxamide | 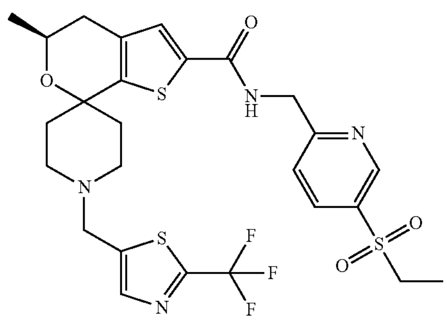 [SMILES: CCS(=O)(=O)c1ccc(CNC(=O)c2cc3c(s2)C2(CCN(Cc4cnc(C(F)(F)F)s4)CC2)O[C@@H](C)C3)nc1] | 615.2 (M + H) |

Example 75

1-(4-Cyano-3-methylbenzyl)-N-[4-(ethylsulfonyl)benzyl]-4',5'-dihydrospiro[piperidine-4,7'-thieno[2,3-c]pyran]-2'-carboxamide

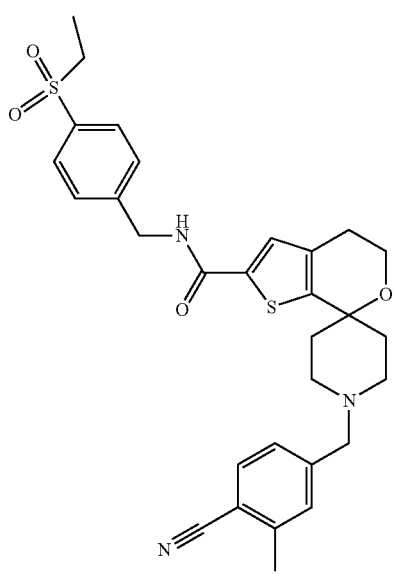 [SMILES: CCS(=O)(=O)c1ccc(CNC(=O)c2cc3c(s2)C2(CCN(Cc4ccc(C#N)c(C)c4)CC2)OCC3)cc1]

In a microwave vial, dissolve N-[4-(ethylsulfonyl)benzyl]-4',5'-dihydrospiro[piperidine-4,7'-thieno[2,3-c]pyran]-2'-carboxamide hydrochloride (0.25 g, 0.53 mmol) and 4-formyl-2-methyl-benzonitrile (0.12 g, 0.83 mmol) in DMF (8 mL) and water (2 mL). Seal the vessel and heat in a microwave to 100° C. for 5 minutes. Cool to ambient temperature and add to a solution of sodium triacetoxyborohydride (0.23 g, 1.06 mmol) in DMF (5 mL). Stir the reaction 12 hours and extract with DCM. Concentrate the organic layer under a stream of nitrogen and purify by silica gel flash chromatography using EtOAc/hexanes to give the title compound (0.14 g, 47%) as a white foam. Mass spectrum (m/z): 564 (M+H).

Example 76

1-[1-(4-Cyanophenyl)ethyl]-N-{[5-(ethylsulfonyl)pyridin-2-yl]methyl}-4'-methyl-4',5'-dihydrospiro[piperidine-4,7'-thieno[2,3-c]pyran]-2'-carboxamide

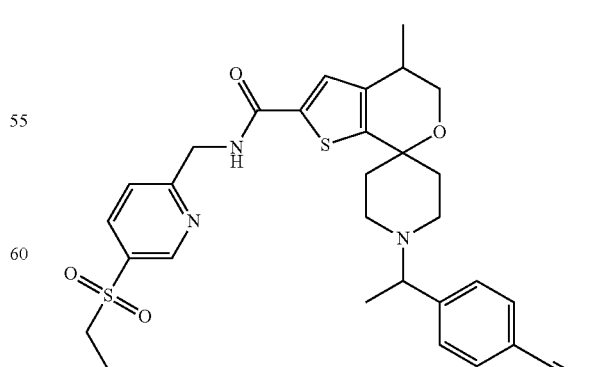

Example 77

(4'S)-1-[(1S)-1-(4-Cyanophenyl)ethyl]-N-{[5-(ethylsulfonyl)pyridin-2-yl]methyl}-4'-methyl-4',5'-dihydrospiro[piperidine-4,7'-thieno[2,3-c]pyran]-2'-carboxamide

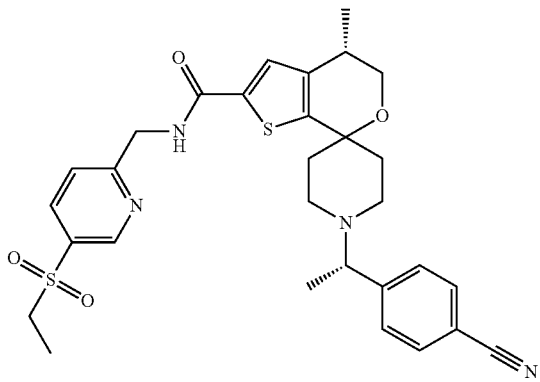 [SMILES: CCS(=O)(=O)c1ccc(CNC(=O)c2cc3c(s2)C2(CCN([C@@H](C)c4ccc(C#N)cc4)CC2)OC[C@H]3C)nc1]

Example 78

1-[1-(4-Cyanophenyl)ethyl]-N-{[5-(ethylsulfonyl)pyridin-2-yl]methyl}-4'-methyl-4',5'-dihydrospiro[piperidine-4,7'-thieno[2,3-c]pyran]-2'-carboxamide isomer 4

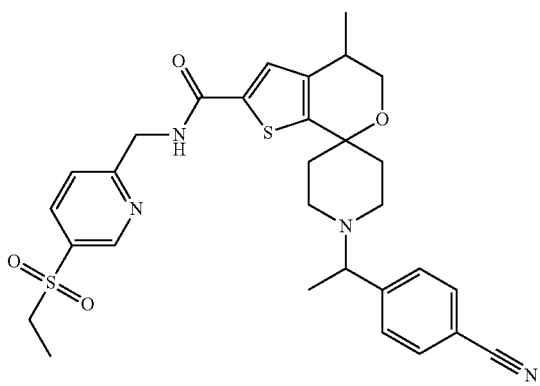 [SMILES: CCS(=O)(=O)c1ccc(CNC(=O)c2cc3c(s2)C2(CCN(C(C)c4ccc(C#N)cc4)CC2)OCC3C)nc1]

Suspend N-[(5-ethylsulfonyl-2-pyridyl)methyl]-4-methyl-spiro[4,5-dihydrothieno[2,3-c]pyran-7,4'-piperidine]-2-carboxamide;hydrochloride (1.02 g, 1.57 mmol) and 4-(1-bromoethyl)benzonitrile (0.439 g, 1.98 mmol) in dry ACN (11 mL) and add DIPEA (2.75 mL, 15.7 mmol) then heat the reaction mixture at 60° C. for 2.5 hours. Add excess 4-(1-bromoethyl)benzonitrile (0.226 g, 1.02 mmol) and heat at 50° C. overnight. Concentrate to dryness and purify the residue using an SCX cartridge and eluting with MeOH (150 mL) followed by 2 N NH$_3$ in MeOH (150 mL). Further purify with silica gel flash chromatography eluting with MeOH/DCM (0:100 to 10:90) to give the title compound of Example 76 (0.898 mg, 91%) as an orange foam. Separate the isomers with chiral chromatography by SFC, AD-H column (30×250 mm, 5μ) with 60% IPA (20 mM NH$_3$) at 100 mL/minute, injection of 2 mL every 8 minutes, temperature=35° C., back pressure=100 bar, UV detection at 260 nm] to obtain Example 78, isomer 4 and an impure mixture of Example 77. Reprocess Example 77 with chiral chromatography by SFC, OD-H column (21.2×250 mm, 5μ) with 35% MeOH (20 mM NH$_3$) at 70 mL/minute, injection of 2.4 mL every 384 seconds, temperature=35° C., back pressure=100 bar, UV detection at 260 nm. Freeze-dry in ACN/water (1:2) to obtain the title compound of Example 77. Analytical conditions: SFC (220 nm UV), column: AD-H 100×4.6 mm, 5μ, mobile phase: 40% IPA (1% of 2 M NH$_3$ in MeOH)/73% CO$_2$, isocratic, column temperature 35° C., flow rate=5 mL/minute, back pressure=100 bar. The title compound of Example 77 (0.144 g, 18%, R$_t$=2.66 minutes), mass spectrum (m/z): 579 (M+H), and the title compound of Example 78, (0.173 g, 20%, 100% ee, R$_t$=6.58 minutes), mass spectrum (m/z): 579 (M+H).

Alternate Preparation Example 77

(4'S)-1-[(1S)-1-(4-Cyanophenyl)ethyl]-N-{[5-(ethylsulfonyl)pyridin-2-yl]methyl}-4'-methyl-4',5'-dihydrospiro[piperidine-4,7'-thieno[2,3-c]pyran]-2'-carboxamide

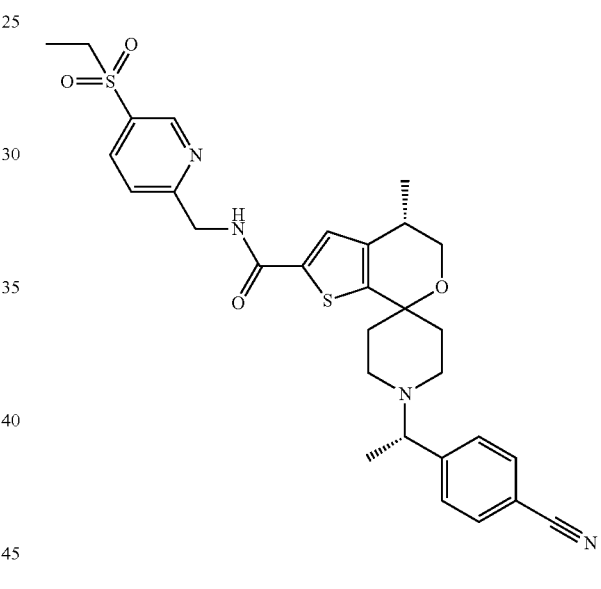

Add (4'S)—N-{[5-(ethylsulfonyl)pyridin-2-yl]methyl}-4'-methyl-4',5'-dihydrospiro[piperidine-4,7'-thieno[2,3-c]pyran]-2'-carboxamide (1.28 g, 2.672 mmol) to a suspension of [(1R)-1-(4-cyanophenyl)ethyl] methanesulfonate (1.34 g, 4.94 mmol) and potassium carbonate (1.48 g, 10.69 mmol) in ACN (12.8 mL) and stir at room temperature. Add excess potassium carbonate (0.369 g, 2.67 mmol) after approximately 22 hours and maintain stirring for over 24 hours. Dilute with MeOH, filter the inorganic and concentrate to dryness. Purify the residue by ion exchange chromatography and by flash chromatography on silica (DCM/MeOH: 0:100 to 5:95). Freeze-dry the residue to obtain the title compound (649.75 mg, 42%). Dissolve the remaining residue in DCM, remove the solvent and freeze dry to obtain a second batch of the title compound with a combined yield (810.13 mg, 52%). Analytical conditions: SFC (220 nm UV), column: OD-H 100×4.6 mm, 5μ, mobile phase: 27% MeOH (1% of 2 M NH$_3$ in MeOH)/73% CO$_2$, isocratic, column temperature 35° C., flow rate=5 mL/minute, back pressure=100 bar], 100% ee, R$_t$=3.86 minutes. Mass spectrum (m/z): 579 (M+H), 601 (M+Na).

Example 79

(5'S)—N-[4-(Ethylsulfonyl)benzyl]-1-{1-[3-fluoro-4-(1,2,4-oxadiazol-3-yl)phenyl]ethyl}-5'-methyl-4',5'-dihydrospiro[piperidine-4,7'-thieno [2,3-c]pyran]-2'-carboxamide

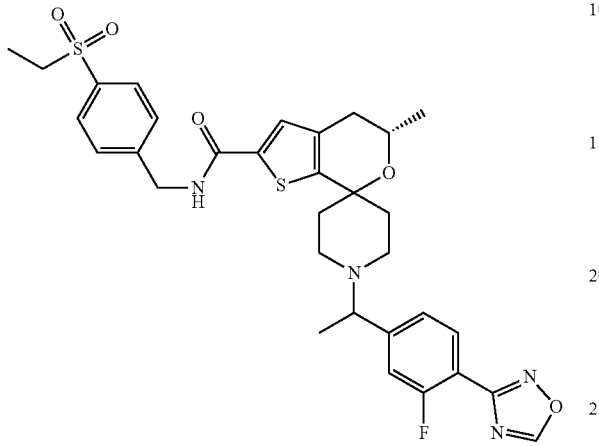

In a screw cap vial containing (5S)—N-[(4-ethylsulfonylphenyl)methyl]-1'-[1-[3-fluoro-4-[(E)-N'-hydroxycarbamimidoyl]phenyl]ethyl]-5-methyl-spiro[4,5-dihydrothieno[2,3-c]pyran-7,4'-piperidine]-2-carboxamide (0.24 g, 0.39 mmol) and trimethyl orthoformate (0.95 g, 9.0 mmol) add boron trifluoride diethyl etherate (0.005 g, 0.039 mmol), then seal the vial and heat to 100° C. overnight. Cool to ambient temperature and purify the resulting residue by silica gel flash chromatography eluting with MeOH (3%)/EtOAc (50-80%)/hexanes to give the title compound (0.11 g, 44%). Mass spectrum (m/z): 639 (M+1).

Example 80

(5'S)—N-[4-(Ethylsulfonyl)benzyl]-1-{ 1-[3-fluoro-4-(1,2,4-oxadiazol-3-yl)phenyl]ethyl}-5'-methyl-4',5'-dihydrospiro[piperidine-4,7'-thieno[2,3-c]pyran]-2'-carboxamide, isomer 1

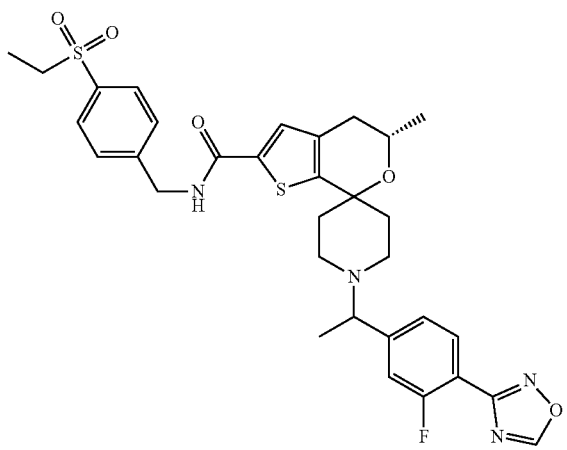 [SMILES: CCS(=O)(=O)c1ccc(CNC(=O)c2cc3c(s2)C2(CCN(C(C)c4ccc(-c5ncon5)c(F)c4)CC2)O[C@@H](C)C3)cc1]

Example 81

(5'S)—N-[4-(Ethylsulfonyl)benzyl]-1-{1-[3-fluoro-4-(1,2,4-oxadiazol-3-yl)phenyl]ethyl}-5'-methyl-4',5'-dihydrospiro[piperidine-4,7'-thieno [2,3-c]pyran]-2'-carboxamide, isomer 2

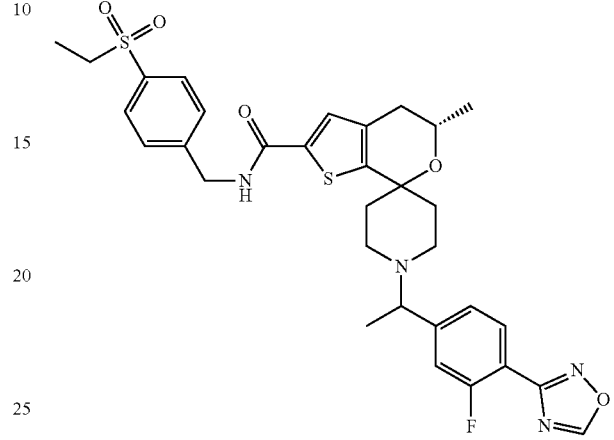

Separate the enantiomers of (5'S)—N-[4-(ethylsulfonyl)benzyl]-1-{1-[3-fluoro-4-(1,2,4-oxadiazol-3-yl)phenyl]ethyl}-5'-methyl-4',5'-dihydrospiro[piperidine-4,7'-thieno [2,3-c]pyran]-2'-carboxamide, Example 67, with chiral chromatography: Chiralpak IA column (30×250 mm, with 40% ACN/60% EtOH with 20 mM $NH_3$ at 30 mL/minute, injection of 0.3 mL (70 mg per injection). Analytical conditions: Chiralpac IA (4.6×150 mm, 225 nm), eluting with 3/2 EtOH/ACN 0.2% IPAm, flow rate 1.0 mL/minute and isolate the title compound of Example 80 (39 mg, 37%, $R_t$=2.35, 100% de), mass spectrum (m/z): 639 (M+1) and Example 81 (33 mg, 31%, $R_t$=4.25, >99% de), mass spectrum (m/z): 639 (M+1).

Biological Assays

RORα, β, and γ Binding Inhibitors

His-tagged human RAR-related orphan receptor alpha (hRORα), human RAR-related orphan receptor beta (hRORβ), and human RAR-related orphan receptor gamma (hRORγ) are used for receptor-ligand competition binding assays to determine $K_i$ values. Typical procedures are provided below.

Receptor competition binding assays are run in a buffer made up of DPBS (1 L) (Hyclone #SH30028.03), 2.2 g BSA Fraction v (Roche #9048-46-8), 100 mL glycerol (Fischer #56-81-5) and 40 mL DMSO (reagent grade). The final wells contain 20 μg/mL aprotinin and 20 μg/mL leupeptin and 10 μM Pefabloc. Typically, receptor binding assays include radio-labeled ligands, such as 7 nM [$^3$H]-25-hydroxycholesterol for alpha binding, 20 nM [$^3$H]-3-[[4-[[3-(2,6-dichlorophenyl)-5-isopropyl-isoxazol-4-yl]methoxy]-N,2-dimethyl-anilino]methyl]benzoic acid for beta binding, and 6 nM [3H]-25-hydroxycholesterol for gamma binding, and 0.5 μg RORα receptor, 0.03 μg RORβ receptor, or 0.13 μg RORγ receptor per well. Assays are typically run in 96-well format. Competing test compounds are added at various concentrations ranging from about 0.4 nM to 25 μM. Non-specific binding is determined in the presence of 250 nM 25-hydroxycholesterol for RORα and RORγ binding, 250 nM 3-[[4-[[3-(2,6-dichlorophenyl)-5-isopropyl-isoxazol-4-yl]methoxy]-N,2-dimethyl-anilino]methyl]benzoic acid for RORβ binding. The sample, label and receptor solutions are combined in a 96 well assay plate (Costar 3632) and incubated overnight at room temperature, then 25 μl beads (Amersham YSi (2-5 micron) copper His-tag Spa Beads, #RPNQ0096) for a final bead concentration of 1 mg/well is added to each reaction. Plates are mixed for 30 minutes on an orbital shaker at room temperature. After an incubation of 4 hours, plates are read in a Wallac MICROBETA® counter.

The data are used to calculate an estimated $IC_{50}$ using a four parameter logistic fit. The Kd for [$^3$H]-25-hydroxycholesterol for RORa and RORg, and [$^3$H]-3-[[4-[[3-(2,6-dichlorophenyl)-5-isopropyl-isoxazol-4-yl]methoxy]-N,2-dimethyl-anilino]methyl]benzoic acid for RORb binding, is determined by saturation binding. The $IC_{50}$ values for compounds are converted to Ki using the Cheng-Prushoff equation.

The results of the following exemplified compounds are shown in Table 15 below.

TABLE 15

| Example # | RORa Ki (nM) | RORb Ki (nM) | RORg Ki (nM) |
|---|---|---|---|
| 16 | 3111 ± 828, n = 4 | >12,500 | 5.885 ± 3.406, n = 5 |
| 25 | 1048 ± 2588, n = 2 | 1144 ± 103, n = 2 | 6.04 ± 1.19, n = 2 |
| 42 | >20,400 | >12,500 | 4.42 ± 2.70, n = 3 |
| 46 | >20,400 | 4840 | 10.8 ± 6.3, n = 2 |
| 55 | 19340 | >12500 | 3.27 ± 1.09, n = 2 |
| 64 | 3271 ± 4105, n = 2 | >22730 | 15.77 ± 7.43, n = 9 |
| 66 | 698.5 ± 130.4, n = 2 | 151.0 ± 107.1, n = 2 | |
| 69 | 9532 | 4473 | |

Mean ± standard deviation

These results demonstrate that the compounds of Table 15 are selective for RORγ versus RORα and RORβ.

HEK293 RORg GAL4 Receptor-Reporter Assay

As an indicator of inverse agonist activity, an RAR-related orphan receptor gamma (RORg) receptor-reporter assay (RORg-GAL4/pGL4.31) is performed in HEK293 cells. HEK293 cells are co-transfected using Fugene™ reagent. A reporter plasmid containing a GAL4 binding domain and a minimal adenoviral promoter upstream of a firefly luciferase gene is co-transfected with a plasmid constitutively expressing a human RORg ligand binding domain fused to yeast GAL4 DNA binding domain. Cells are transfected in T150 cm$^2$ flasks in MEM media without FBS. After 18 hours incubation, transfected cells are trypsinized, plated in 96-well microtiter plates in 3:1 DMEM-F12 media containing 10% FBS, incubated for 4 hours and then exposed to various concentrations of test compounds ranging from about 0.05 nM to 10 μM. After 18 hours of incubations with compounds, cells are lysed and luciferase activity is quantified using standard techniques. Data is fit to a 4 parameter-fit logistics to determine $IC_{50}$ values.

The results of the following exemplified compounds are shown in Table 16 below.

TABLE 16

| Example # | $hIC_{50}$ (nM) |
|---|---|
| 16 | 10.92 ± 12.64, n = 6 |
| 25 | 16.2 ± 9.7, n = 4 |

TABLE 16-continued

| Example # | $hIC_{50}$ (nM) |
|---|---|
| 42 | 19.9 ± 10.7, n = 2 |
| 46 | 144 ± 34, n = 2 |
| 55 | 40.9 ± 41.8, n = 2 |
| 64 | 17.09 + 9.14, n = 5 |
| 66 | 31.4 ± 11.2, n = 2 |
| 69 | 15.4 ± 13.4, n = 2 |

Mean ± standard deviation

These results demonstrate that the compounds of Table 16 are inverse agonists for human RORg receptor.

PBMC IL-17 Secretion ELISA and Cell TiterGlo Viabiltiy Assay

PBMC's are isolated from whole blood buffy coats by first combining fresh buffy coats with equal volumes of phosphate buffered saline. Thirty five mL of PBS/buffy coat solution are then gently overlaid onto 15 mL of Ficoll in 50 mL conical tubes. Following centrifugation for 30 minutes at 500×g (with slow acceleration and deceleration) the top layer of plasma is discarded and the layer of cells along the Ficoll interface is collected and pooled. Each 250 mL tube is filled to the top with room temperature RPMI-1640 media. Tubes are spun for 10 minutes at 500×G (with slow acceleration and deceleration), the media is removed by aspiration, and the wash step is repeated. Cells are resuspended in ice cold Recovery Cell Culture Freezing Medium from Life Technologies (Catalog number 12648-010) on ice. The cell concentration is adjusted to 66.7 million cells/mL. Cell are slow frozen at −1° C./minute in vials with 100 million cells and stored in liquid nitrogen.

Stimulation of IL-17 Secretion and Compound Addition

PBMC are brought out of thaw by resuspending with 1 mL of complete media (RPMI-1640 containing 30 mM HEPES, 100 units/mL penicillin, 100 μg/mL streptomycin, 3.25 mM L-Glutamine, 0.2 μM beta-mercaptoethanol, and 10% FBS) followed by the drop wise addition of 2 mL, 4 mL, 8 mL, and 16 mL of complete media with gentle swirling. Cells are spun down for 5 minutes and the cell pellet is resuspended in complete media. Clumps of cells are broken up by running the cell solution through a 23 gauge syringe needle and a 40 μM cell strainer. One hundred thousand cells per well are added to 384 well polystyrene tissue culture treated flat bottomed plates in a total of 30 μL. Stimulation cocktail containing anti-human CD3 antibody, anti-human CD28 antibody, IL-23 and compounds prepared in complete media are added to the cells simultaneously in a total volume of 30 μL. The final concentration of added stimulants is 160 ng/mL, 500 ng/mL, and 5 ng/mL for anti-CD3 antibody, anti-CD28 antibody, and IL-23 respectively and 0.3% for DMSO. Plates are sealed with AERASEAL® sealing film and incubated for 48 hours at 37° C., 95% humidity, and 5% $CO_2$.

Following the incubation period, the plates are spun at 200×g for five minutes. Supernatants are diluted 1:1 with equal volume 1% BSA/PBS and tested for IL-17 with a human IL-17 ELISA kit from R&D system (catalog #D317E) according to the protocol provided with the kit with one exception—the colorimetric substrate OPD (o-phenylenediamine dihydrochloride, Sigma Cat #P6912) is used instead of the substrate supplied in the kit. Absorbance at 492 nm is measured with the Envision multi-label plate reader. A492 values are converted to concentration of IL-17 based on the IL-17 standard curve as shown below: pg/mL IL-17=EC50*[[(Top-Bottom)/(A492-Bottom)]-1](1/-Hill). $IC_{50}$'s for inhibition of IL-17 secretion is calculated based on converted values using a standard 4-parameter fit with maximum inhibition determined from the average values of wells with no added stimulants nor compounds and minimum inhibition from the average values of wells with stimulants alone and no added compound.

Equal volumes of Cell TITERGLO® cell viability testing reagent (Promega Cat #G7573) are added to the cells remaining in the plates, and following a fifteen minute incubation with gentle shaking at room temperature luminescence is measured with the Envision multi-label plate reader. Percent cell death is calculated by setting 100% activity (cell death) to zero luminescence units and minimum activity (max number of viable cells) as the average luminescence units of wells containing stimulants alone and no added compound. $IC_{50}$'s are calculated using a standard four parameter fit.

The results of the following exemplified compounds are shown in Table 17 below.

TABLE 17

| Example # | hPBMC IL-17 ELISA ($EC_{50}$, nM) | Cell TiterGlo Viability ($EC_{50}$, µM) |
|---|---|---|
| 16 | 10.6 ± 6.5, n = 20 | >1.0 |
| 25 | 30.8 ± 25.7, n = 6 | >1.0 |
| 42 | 8.3 ± 3.8, n = 6 | >1.0 |
| 46 | 24.5 ± 11.9, n = 6 | >1.0 |
| 55 | 12.6 ± 8.1, n = 6 | >1.0 |
| 64 | 21.7 ± 11.3, n = 9 | >3.0 |
| 66 | 13.3 ± 4.7, n = 5 | >1.0 |
| 69 | 30.0 ± 18.5, n = 5 | >1.0 |

Mean ± standard deviation

These results show that the compounds of Table 17 inhibit anti-CD3/anti-CD28/IL-23 stimulated IL-17 secretion in PBMC's without measurable cytotoxic effect.

Glucose-6-Phosphate Isomerase (GPI) Induced Arthritis Model

The GPI induced arthritis model is adapted from K. Iwanami et al *Arthritis Rheumatism* 58, 754-763, 2008 and D. Schubert et al. *J Immunology* 172, 4503-4509, 2004. Mice (8-9 week old male DBA/1 mice) (Harlan) are randomly assigned into treatment groups based on body weights collected on the day of immunization (day 0). On the day of immunization (day 0), a 1:1 (v:v) mixture of recombinant human GPI (diluted to 4 mg/mL in PBS, Gibco) and complete Freund's adjuvant (CFA, Sigma) is mixed on a high speed homogenizer (Omni) for 40 minutes in a cold room. A final concentration of 2 mg/mL GPI is achieved in the emulsion. Mice are injected at the base of the tail (2 sites of injection, subcutaneously, 100 µL each site) with the GPI emulsion. Test compounds are dosed orally starting on the same day as immunization (day 0). Starting on day 0, each paw is scored for severity of joint swelling based on a 0 to 3 scoring system (See K. Iwanami et al *Arthritis Rheumatism* 58, 754-763, 2008. The clinical score represents the total score of all 4 paws (maximum score=12). Clinical scores are assessed on days 0, 2, 4, 7, 8, 9, 10, 11, 12, 14, 16, 18, and 21.

The AUC is calculated by a trapezoid method for clinical score over time from the day of immunization (day 0) to day 21. Test p-values were derived from Student's t-test.

Example 55 (100 mg/Kg) and vehicle (1% HEC, 0.25% Polysorbate 80, and 0.05% Antifoam in purified water) treatments (n=8/group) are initiated on day 0 and administered orally once daily. Example 55 reduces severity of paw swelling and maintains lower mean clinical scores through the course of disease compared to the vehicle group. This effect results in 94% reduction in clinical score AUC, a cumulative measure of paw swelling over time, that is statistically significant compared to the vehicle group as shown in Table 18.

TABLE 18

| Treatment | Clinical Score AUC (mean ± SEM) |
|---|---|
| Vehicle | 79.57 ± 8.71 |
| Example 55 | 7.50 ± 2.08* |

Values are shown as mean ± SEM.
*p < 0.05 vs. Vehicle (Student's t-test). SEM = standard error of the mean

We claim:
1. A compound of formula

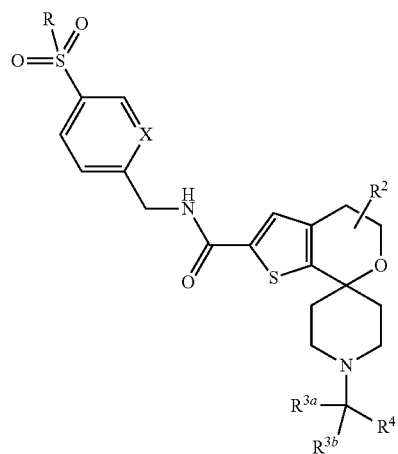

wherein
n is 0, 1, or 2;
X is independently —N— or —CH—;
$R^1$ is —$C_{1-3}$ alkyl;
$R^2$ is —H or —$CH_3$;
$R^{3a}$ and $R^{3b}$ are independently —H, —$CH_3$, or —$CH_2CH_3$;
$R^4$ is

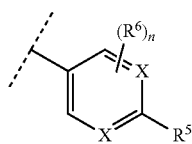

or thiazolyl optionally substituted with —$CF_3$;
$R^5$ is halo, —CN, —$CF_3$, oxadiazolyl, or oxadiazolyl optionally substituted with $CH_3$,
$R_6$ is —OMe, halo, —$CH_3$, or —$CF_3$;

provided that when n is 0, X is —N—, —R¹ is —CH₂CH₃, R² is —CH₃ in the position adjacent to the —O—, R³ᵃ and R³ᵇ are —H and —CH₃, then R⁵ cannot be —CF₃;
or a pharmaceutically acceptable salt thereof.

2. The compound of claim 1 of the formula

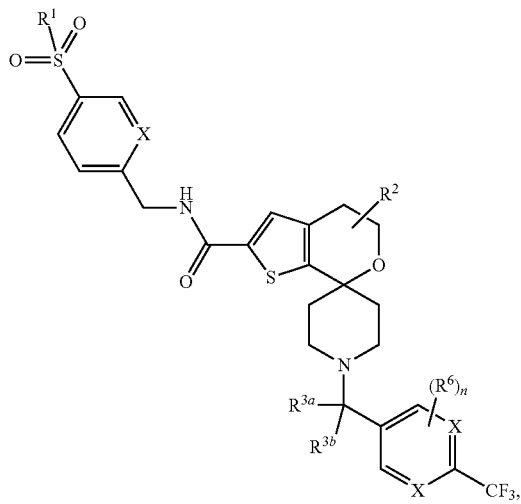

wherein
n is 0 or 1;
X is independently —N— or —CH—;
R¹ is —C₁₋₃ alkyl;
R² is —H or —CH₃;
R³ᵃ and R³ᵇ are independently —H, —CH₃, or —CH₂CH₃;
R₆ is halo, or —CH₃;
provided that when n is 0, X is —N—, —R¹ is —CH₂CH₃, R² is —CH₃ in the position adjacent to the —O— then R³ᵃ and R³ᵇ cannot be —H and —CH₃;
or a pharmaceutically acceptable salt thereof.

3. The compound of claim 1 of the formula

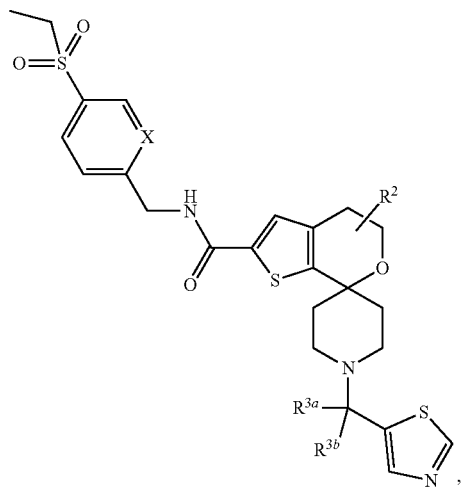

wherein
X is —N— or —CH—;
R² is —H or —CH₃;
R³ᵃ and R³ᵇ are independently —H or —CH₃;
or a pharmaceutically acceptable salt thereof.

4. The compound of claim 1 that is (5'S)—N-[4-(ethylsulfonyl)benzyl]-5'-methyl-1-{(1R)-1-[2-(trifluoromethyl)pyrimidin-5-yl]ethyl}-4',5'-dihydrospiro[piperidine-4,7'-thieno[2,3-c]pyran]-2'-carboxamide:

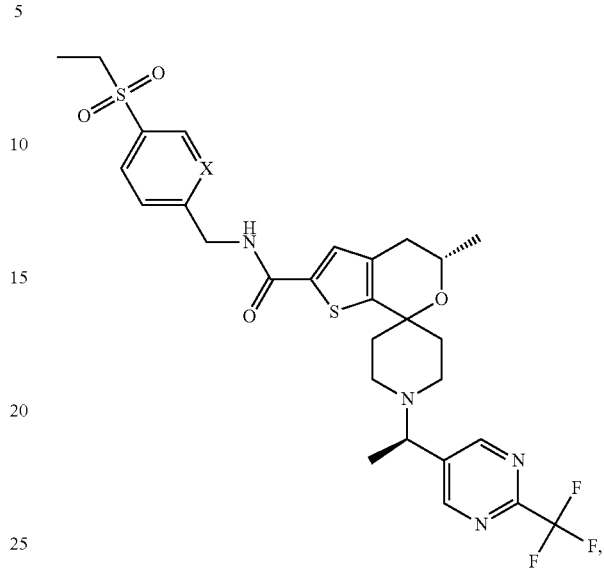

or a pharmaceutically acceptable salt thereof.

5. The compound of claim 1 that is (5'S)—N-{[5-(ethylsulfonyl)pyridin-2-yl]methyl}-5'-methyl-1-{1-[2-(trifluoromethyl)-1,3-thiazol-5-yl]ethyl}-4',5'-dihydrospiro[piperidine-4,7'-thieno[2,3-c]pyran]-2'-carboxamide:

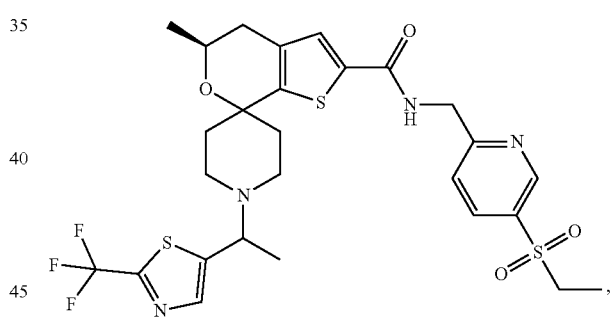

or a pharmaceutically acceptable salt thereof.

6. A pharmaceutical composition comprising a compound of claim 1, or a pharmaceutically acceptable salt thereof, in combination with one or more pharmaceutically acceptable carriers, diluents, or excipients.

7. The pharmaceutical composition according to claim 6 comprising one or more other therapeutic agents.

8. A method of treating psoriasis comprising administering a compound of claim 1, or a pharmaceutically acceptable salt thereof, to a patient in need thereof.

9. A method of treating seronegative spondylarthropathies comprising administering a compound of claim 1, or a pharmaceutically acceptable salt thereof, to a patient in need thereof.

10. The method according to claim 9 for treating axial spondyloarthritis, ankylosing spondylitis, or psoriatic arthritis.

11. The compound according to claim 1 wherein R¹ is ethyl.

12. The compound according to claim 1 wherein $R^1$ is methyl.

13. The compound according to claim 11 wherein $R^2$ is —$CH_3$.

14. The compound according to claim 12 wherein $R^2$ is —$CH_3$.

15. The compound according to claim 13 wherein $R^{3a}$ and $R^{3b}$ are —H and —H.

16. The compound according to claim 14 wherein $R^{3a}$ and $R^{3b}$ are —H and —$CH_3$.

* * * * *